(12) United States Patent
Cuttitta et al.

(10) Patent No.: US 7,622,272 B2
(45) Date of Patent: Nov. 24, 2009

(54) FUNCTIONAL ROLE OF ADRENOMEDULLIN (AM) AND THE GENE-RELATED PRODUCT (PAMP) IN HUMAN PATHOLOGY AND PHYSIOLOGY

(75) Inventors: Frank Cuttitta, Adamstown, MD (US); Alfredo Martinez, La Rioja (ES)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 75 days.

(21) Appl. No.: 11/517,599

(22) Filed: Sep. 5, 2006

(65) Prior Publication Data

US 2007/0004630 A1 Jan. 4, 2007

Related U.S. Application Data

(60) Continuation of application No. 09/931,700, filed on Aug. 16, 2001, now Pat. No. 7,101,548, which is a division of application No. 09/011,922, filed as application No. PCT/US96/13286 on Aug. 16, 1996, now Pat. No. 6,320,022.

(60) Provisional application No. 60/013,172, filed on Mar. 12, 1996, provisional application No. 60/002,936, filed on Aug. 30, 1995, provisional application No. 60/002,514, filed on Aug. 18, 1995.

(51) Int. Cl.
| | |
|---|---|
| G01N 33/53 | (2006.01) |
| A01N 37/18 | (2006.01) |
| A61K 38/00 | (2006.01) |
| C07K 2/00 | (2006.01) |
| C07K 4/00 | (2006.01) |
| C07K 14/00 | (2006.01) |
| C07K 5/00 | (2006.01) |
| C07K 16/00 | (2006.01) |

(52) U.S. Cl. .................. 435/7.8; 530/300; 530/324; 514/2

(58) Field of Classification Search .................. None
See application file for complete search history.

(56) References Cited

U.S. PATENT DOCUMENTS 5,639,855 A * 6/1997 Kitamura et al. ............ 530/324
5,910,416 A    6/1999 Kitamura et al.

FOREIGN PATENT DOCUMENTS

| EP | 0622458 A2 | 11/1994 |
| JP | 07-196693 | 8/1995 |
| WO | WO 93/17715 | 9/1993 |
| WO | WO 94/25482 | 11/1994 |

OTHER PUBLICATIONS

Wheeler. Preventive vaccines for cervical cancer. Salud Publica de Mexico, 1997. vol. 39, pp. 1-9.*

Efferson, Kawano, Tsdua, Palese, Garcia-Sastre, and Ioannides. Stimulation of human T cells by an influenza A vector expressing a CTL epitope from the HER2/neu protooncogene results in higher numbers of antigen-specific TCRhi cells than stimulation with peptide. Anticancer Research, 2005. vol. 25, pp. 715-724.*

Bachman, Wolint, Schwarz, and Oxenius. Recall proliferation potential of memory CD8+ T cells and antiviral protection. Journal of Immunology, 2005. vol. 175, pp. 4677-4685.*

Ahren et al., "Adrenomedullin is localized to the gut and stimulates insulin-secretion in the rat," *Diabetologia*, 38:108A, 1995 (Abstract).

Curti "Physical barriers to drug delivery in tumors," *Crit. Rev. in Oncology/Hematology*, 14(1):29-39, 1993.

Cuttitta et al., "Bombesin-like peptides can function as autocrine growth factors in human small-cell lung cancer," *Nature* 316(6031):823-826, 1985.

Dermer, *Bio/Technology*, 12:20, 1994.

Drexler et al., "Recent results on the biology of Hodgkin and Reed-Sternberg cells. II. Continuous cell lines," *Leuk Lymphoma*, 9:1-25, 1993.

Embleton et al., *Immunol. Ser.*, 23:181-207, 1984.

Freshney, "Culture of Animal Cells, A Manual of Basic Technique," *Alan R. Liss, Inc.*, 1983, New York, p. 4.

Gura T., "Systems for identifying new drugs are often faulty," *Science*, 278(5340):1041-1042, 1997.

Hartwell et al., "Integrating genetic approaches into the discovery of anticancer drugs," *Science*, 278(5340):1064-1068, 1997.

Hird et al., *Genes and Cancer*, Carney et al., Ed., John Wiley and Sons, LTS, 1990 pp. 83-89.

Hsu, "Tissue Culture Methods and Applications," *Kruse and Patterson, Eds.*, Academic Press, New York, see abstract, p. 764, 1973.

Imai et al., "Hormonal regulation of rat adrenomedullin gene in vasculature," *Endocrinology*, 136[4]:1544-1548, 1995.

Ishikawa et al., "Adrenomedullin Antagonist Suppresses in Vivo Growth of Human Pancreatic Cancer Cells in SCID Mice by Suppressing Angiogenesis," *Oncogene* 22:1238-1242, 2003.

(Continued)

*Primary Examiner*—David J. Blanchard
*Assistant Examiner*—Anne M. Gussow
(74) *Attorney, Agent, or Firm*—Klarquist Sparkman, LLP

(57) ABSTRACT

The methods of the present invention demonstrate that adrenomedullin (AM) is expressed in human cancer cell lines of diverse origin and functions as a universal autocrine growth factor driving neoplastic proliferation. The present invention provides for AM peptides and AM antibodies useful in therapeutic, pharmacologic and physiologic compositions. The present invention additionally provides for methods of diagnosis, treatment and prevention of disease utilizing compositions comprising the AM peptides and antibodies of the present invention. The methods of the present invention also provide for experimental models for use in identifying the role of AM in pancreatic physiology. The methods pertaining to rat isolated islets have show that AM inhibits insulin secretion in a dose-dependent manner. The monoclonal antibody MoAb-G6, which neutralizes AM bioactivity, was show by the methods of the present invention to increase insulin release fivefold, an effect that was reversed by the addition of synthetic AM.

5 Claims, 26 Drawing Sheets

OTHER PUBLICATIONS

RK Jain, "Barriers to drug delivery in solid tumors," *Sci. Am.*, 271(1):58-65, 1994.
Kamoi et al., "Adrenomedullin inhibits the secretion of cytokine-induced neutrophil chemoattractant, a member of the interleukin-8 family, from rat alveolar macrophages," *Biochem. Biophys. Res. Commun.*, 211[3]:1031-1035, 1995.
Kanazawa et al., "Adrenomedullin, a newly discovered hypotensive peptide, is a potent bronchodilator," *Biochem. Biophys. Res. Commun.*, 205[1]:251-254, 1994.
Kimmel et al., *J. Neurosurg*, 66:1611-171, 1987.
Kitamura et al., "Adrenomedullin: A novel hypotensive peptide isolated from human pheochromocytoma," *Biochem. Biophys. Res. Commun.*, 192[2]:553-560, 1993.
Kobayashi et al., "Adrenomedullin stimulates the cell cycle progression and the expression of c-fos messenger RNA in vascular smooth muscle cells in primary culture," *Circulation*, 92:I-694, 1995 (Abstract #3335).
Martínez et al., "Adrenomedullin, a new hypotensive peptide, is expressed in normal lung and in primary tumors," *Proc. Amer. Assoc. Canc. Res.*, 36:265, 1995 (Abstract #1580).
Martínez et al., "Expression of adrenomedullin in normal human lung and in primary tumors," *Endocrinology* 136[9]:4099-4105, 1995.
Martínez et al., "Regulation of Insulin Secretion and Blood Glucose Metabolism by Adrenomedullin," *Endocrinology* 137(6):2626-2632, 1996.
Martínez et al., "Is Adrenomedullin a Causal Agent in Some Cases of Type 2 Diabetes?" *Peptides* 20:1471-1478, 1999.
Michibata et al., "Production and action of adrenomedullin (AM) in cultured mesangial cells revealed by a specific monoclonal antibody to AM," *J. Amer. Soc. Nephrol.*, 6:741, 1995 (Abstract #1856).
Miller et al., "Expression of adrenomedullin mRNA in normal human tissues and cancer cell lines as expressed by RT-PCR and immunoblot," *Proc. Amer. Assoc. Canc. Res.*, 36:261, 1995 (Abstract #1554).
Ouafik et al., "Neutralization of Adrenomedullin Inhibits the Growth of Human Glioblastoma Cell Lines in Vitro and Suppresses Tumor Xenograft Growth in Vivo," *American Journal of Pathology* 160(4):1279-1292, 2002.
Parkes et al., "ACTH-suppressive and vasodilator actions of adrenomedullin in conscious sheep," *J. Neuroendo.*, 7:923-929, 1995.
Ruggeri et al., "CEP-7055: A Novel, Orally Active Pan Inhibitor of Vascular Endothelial Growth Factor Receptor Tyrosine Kinases with Potent Antiangiogenic Activity and Antitumor Efficacy in Preclinical Models," *Cancer Research* 63:5978-5991, 2003.
Samson et al., "A novel vasoactive peptide, adrenomedullin, inhibits pituitary adrenocorticotropin release," *Endocrinology*, 136[5]:2349-2352, 1995.
Sato et al., "Adrenomedullin induces expression of c-fos and AP-1 activity in rat vascular smooth muscle cells and cardiomyocytes," *Biochem. Biophys. Res. Commun.*, 217[1]:211-216, 1995.
Satoh et al., "Adrenomedullin in human brain, adrenal-glands and tumor-tissues of pheochromocytoma, ganglioneuroblastoma and neuroblastoma," *J. Clin. Endocrinol. Metabol.*, 80[5]:1750-1752, 1995.
Schlom, "Molecular Foundations of Oncology," *Broder Ed., Williams and Williams*, Baltimore, pp. 95-134, 1991.
Slamon et al., *Cancer Cells*, 7:371-384, 1989.
Sugo et al., "Production and secretion of adrenomedullin from vascular smooth muscle cells: Augmented production by tumor necrosis factor-α.," *Biochem. Biophys. Res. Commun.*, 203[1]:719-726, 1994.
Sugo, et al., "Interleukin-1, tumor-necrosis-factor and lipopolysaccharides additively stimulates production of adrenomedullin in vascular smooth muscle cells," *Biochem. Biophys. Res. Commun.*, 207[1]:25-32, 1995.
Yamaguchi et al., "Effect of adrenomedullin on aldosterone secretion by dispersed rat adrenal zona glomerulosa cells," *Life. Scie.*, 56[6]: 379-387, 1995.
Zellner et al., "Disparity in expression of protein kinase C alpha in human glioma versus glioma-derived primary cell lines: therapeutic implications," *Clin. Can. Res.*, 4:1797-1802, 1998.
Eguchi et al., "Structure-Activity Relationship of Adrenomedullin, a Novel Vasodilatory Peptide, in Cultured Rat Vascular Smooth Muscle Cells," *Endocrinology*, 135(6):2454-2458, 1994.
Ishimitsu et al., "Genomic Structure of Human Adrenomedullin Gene," *Biochem and Biophy Resrch Comm.*, 203(1):631-639, 1994.

* cited by examiner

Gene
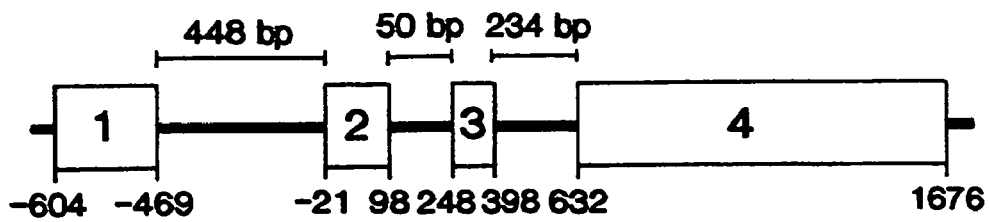
Message
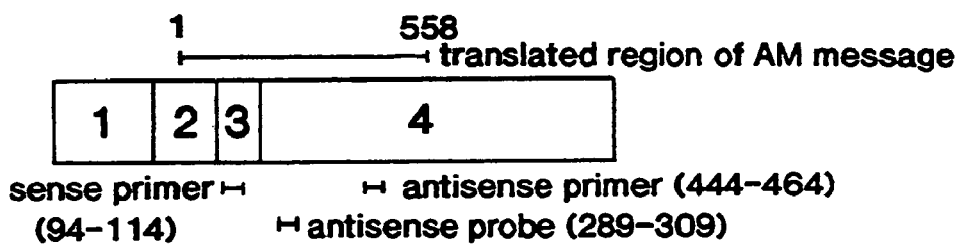
Preprohormone
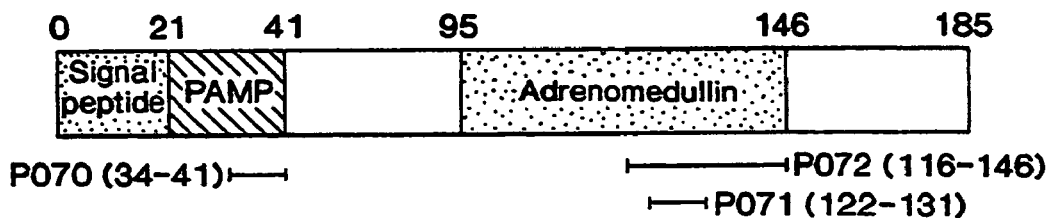
FIG. 1

HISTAMINE RELEASE FROM RAT MAST CELLS

| Peptide | $HR_{50}$ [M][1] | Rats |
|---|---|---|
| | ($\bar{x} \pm SD$) | (n) |
| AM | $7.9 \pm 3.9 \times 10^{-6}$ | 5 |
| PO71 | $> 10^{-3}$ | 1 |
| PO72 | $> 10^{-4}$ | 1 |
| $AM_{1-12}$ | $> 10^{-4}$ | 1 |
| PAMP | $4.7 \pm 2.3 \times 10^{-7}$ | 5 |
| PO70 | $2.6 \times 10^{-6}$ | 1 |
| Controls | | |
| LHRH | $1.7 \times 10^{-4}$ | 2 |
| NalArg | $1.5 \pm 53 \times 10^{-7}$ | 5 |

$HR_{50}$ = molar concentration of peptide required to release 50% of total histamine from rat peritoneal mast cells.

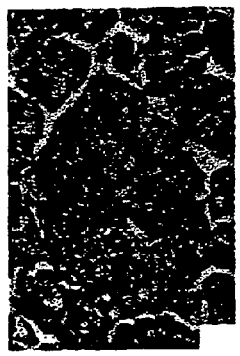
FIG. 17A
FIG. 17B
FIG. 17C
FIG. 17D
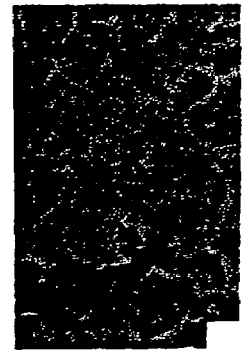
FIG. 17E
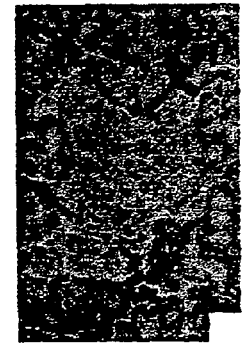
FIG. 17F
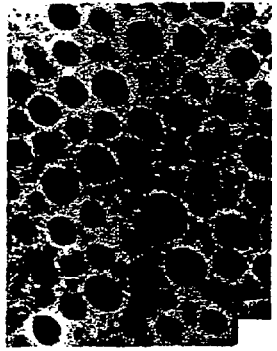
FIG. 17G
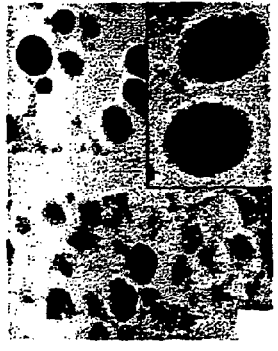
FIG. 17H 292 bp -

292 bp -

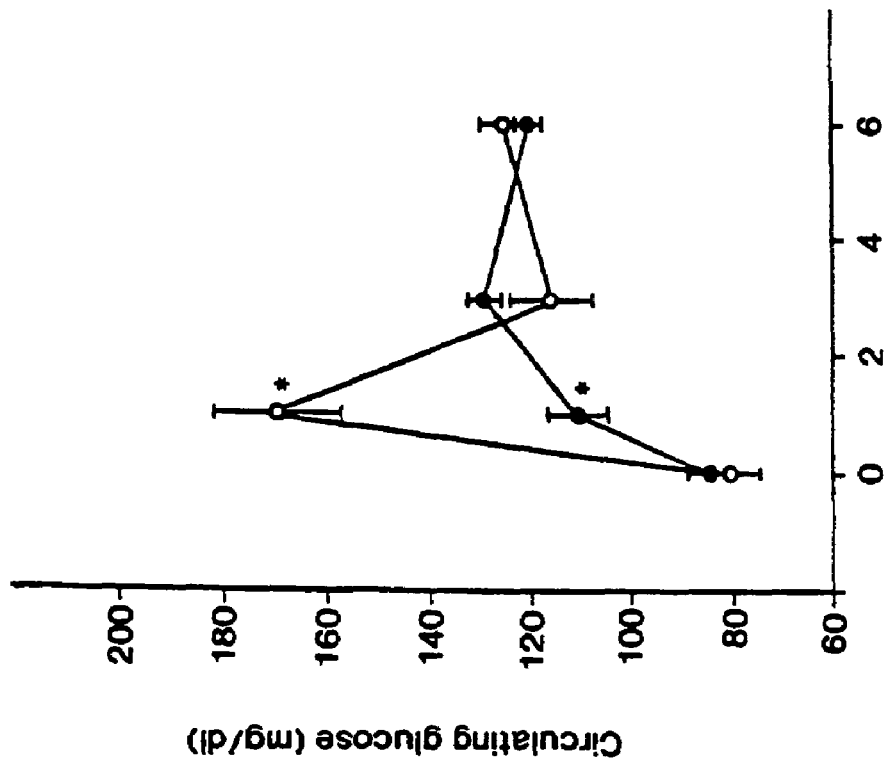
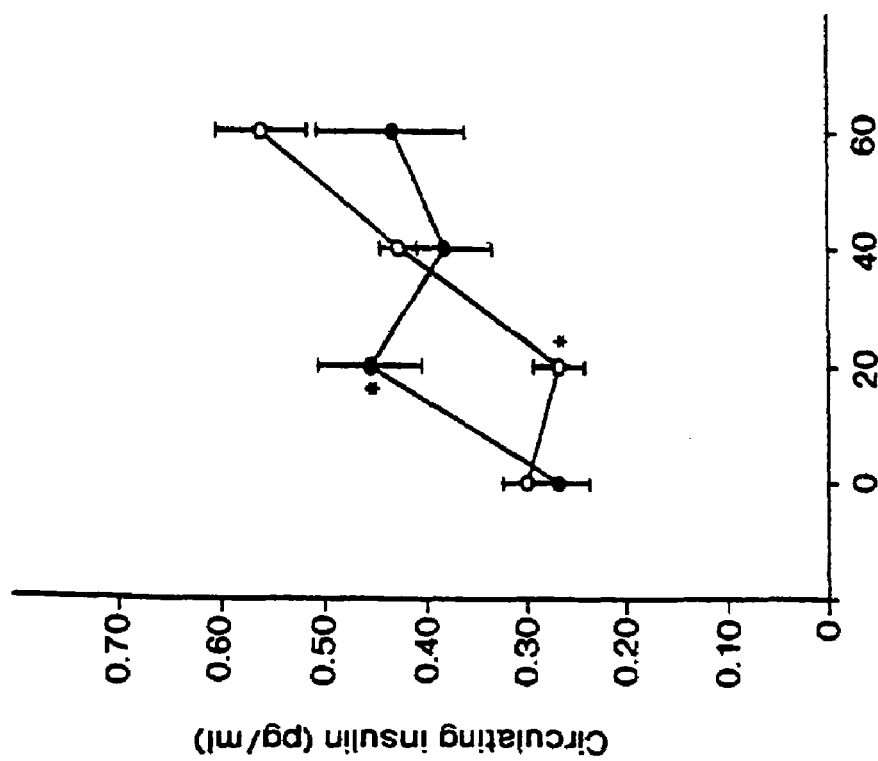
FIG. 20A
FIG. 20B

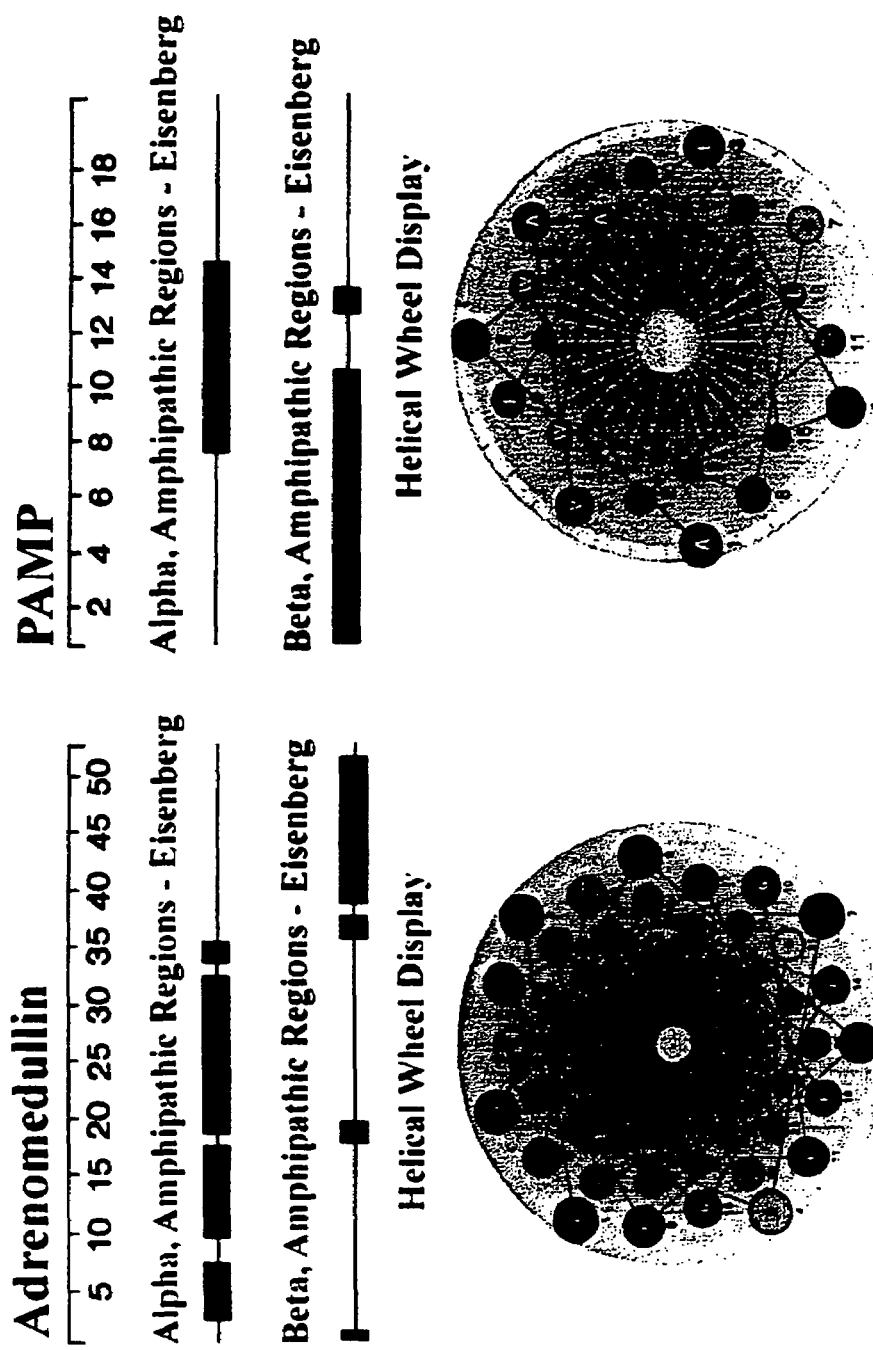

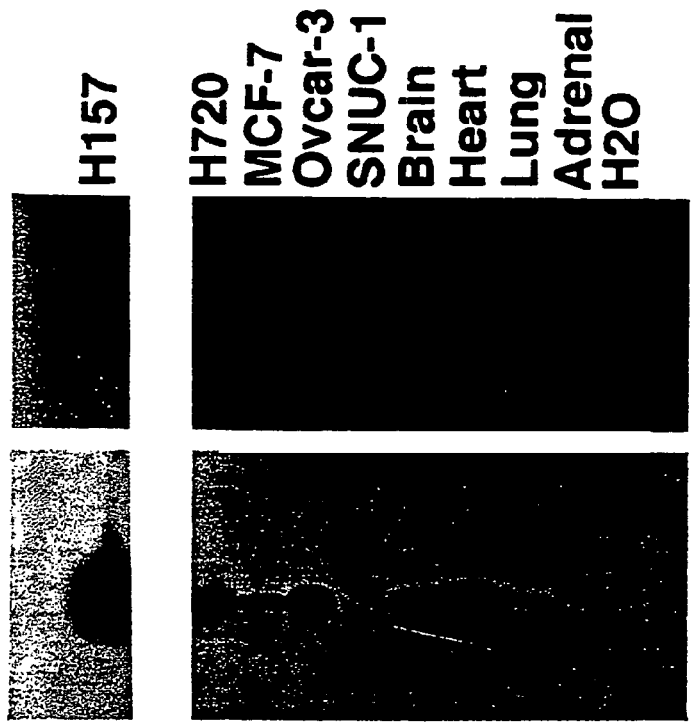
FIG. 26A
- 410 bp
FIG. 26B
- 471 bp
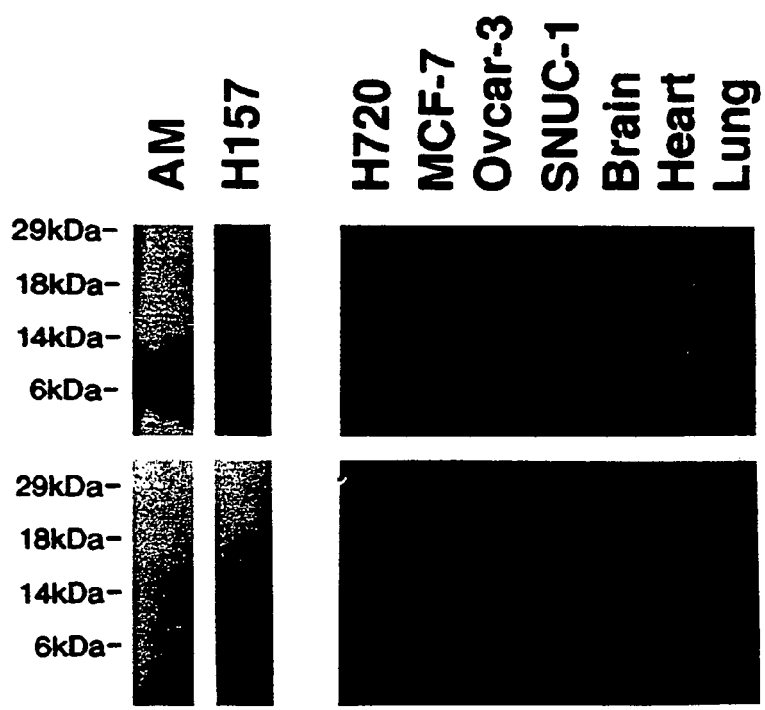
FIG. 26C
FIG. 26D

```
                          SEQUENCE LISTING

<160> NUMBER OF SEQ ID NOS: 17

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Peptide,
      P070, YY-PreproAM (amino acids 34-41)

<400> SEQUENCE: 1

Tyr Tyr Trp Asn Lys Trp Ala Leu Ser Arg
 1               5                  10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Peptide,
      P071, YGG-PreproAM (amino acids 122-131)

<400> SEQUENCE: 2

Tyr Gly Gly His Gln Ile Tyr Gln Phe Thr Asp Lys Asp
 1               5                  10

<210> SEQ ID NO 3
<211> LENGTH: 31
<212> TYPE: PRT
<213> ORGANISM: Artificial Sequence
<220> FEATURE:
<223> OTHER INFORMATION: Description of Artificial Sequence: Peptide,
```

-continued

P072, PreproAM (amino acids 116-146)

<400> SEQUENCE: 3

Thr Val Gln Lys Leu Ala His Gln Ile Tyr Gln Phe Thr Asp Lys Asp
 1               5                  10                  15

Lys Asp Asn Val Ala Pro Arg Ser Lys Ile Ser Pro Gln Gly Tyr
            20                  25                  30

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Nucleic
      Acid, sense primer, AM, (nucleotides 94-114)

<400> SEQUENCE: 4
aagaagtgga ataagtgggc t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Nucleic
      Acid, antisense primer, AM, (nucleotide 444-464)

<400> SEQUENCE: 5
tggcttagaa gacaccagag t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Nucleic
      Acid, antisense probe, AM, (nucleotides 289-309)

<400> SEQUENCE: 6
ctggaagttg ttcatgctct g                                              21

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Peptide,
      PAMP-20, Proadrenomedullin N-terminal 20 amino
      acids

<400> SEQUENCE: 7

Ala Arg Leu Asp Val Ala Ser Glu Phe Arg Lys Lys Trp Asn Lys Trp
 1               5                  10                  15

Ala Leu Ser Arg
            20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Nucleic
      Acid, sense primer, AM, (nucleotides 250-270)

<400> SEQUENCE: 8
aagaagtgga ataagtgggc t                                              21

-continued

```
<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Nucleic
      Acid, antisense primer, AM, (nucleotides 640-660)

<400> SEQUENCE: 9
tggcttagaa gacaccagag t                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Nucleic
      Acid, Nested Antisense probe, AM, (nucleotides 541-561)

<400> SEQUENCE: 10
gacgttgtcc ttgtccttat c                                              21

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Nucleic
      Acid, AM-R amplification sense primer (nucleotides 476-497)

<400> SEQUENCE: 11
agcgccacca gcaccgaata cg                                             22

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Nucleic
      Acid, AM-R amplification antisense primer (nucleotides 923-946)

<400> SEQUENCE: 12
agaggatggg gttggcgaca cagt                                           24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Nucleic
      Acid, AM-R antisense probe (nucleotides 788-811)

<400> SEQUENCE: 13
ggtagggcag ccagcagatg acaa                                           24

<210> SEQ ID NO 14
<211> LENGTH: 31
<212> TYPE: PRT
<213> ORGANISM: Artificial Sequence
<220> FEATURE:
<223> OTHER INFORMATION: Description of Artificial Sequence: Peptide,
      Synthetic homolog of AM (P072), Structural amino
      acid sequence representing two-thirds of the
      intact AM peptide

<400> SEQUENCE: 14
```

```
Thr Val Gln Lys Leu Ala His Gln Ile Tyr Gln Phe Thr Asp Lys Asp
 1               5                  10                  15

Lys Asp Asn Val Ala Pro Arg Ser Lys Ile Ser Pro Gln Gly Tyr
            20                  25                  30

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Nucleic
      Acid, Sense primer, AM, (nucleotides 250-270); Recognizes the most
      conserved regions of the AM gene

<400> SEQUENCE: 15
aagaagtgga ataagtgggc t                                              21

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Nucleic
      Acid, Antisense primer, AM, (nucleotides 523-542); Recognizes the
      most conserved regions of the AM gene

<400> SEQUENCE: 16
tgtgaactgg tagatctggt                                                20

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Nucleic
      acid probe, AM, (nucleotides 430-450); Detects the AM gene via
      Southern Blot

<400> SEQUENCE: 17
tctggcggta gcgcttgact c                                              21
```

FUNCTIONAL ROLE OF ADRENOMEDULLIN (AM) AND THE GENE-RELATED PRODUCT (PAMP) IN HUMAN PATHOLOGY AND PHYSIOLOGY

CROSS REFERENCE TO RELATED APPLICATIONS

This is a continuation of U.S. patent application Ser. No. 09/931,700, filed Aug. 16, 2001, now U.S. Pat. No. 7,101,548 which is a divisional of U.S. patent application Ser. No. 09/011,922, filed Feb. 17, 1998, now U.S. Pat. No. 6,320,022, issued on Nov. 20, 2001, which is a 371 U.S. National Stage of PCT/U596/13286, filed Aug. 16, 1996, which was published in English under PCT Article 2(2), which in turn claims the benefit of U.S. Provisional Application 60/013,172, filed Mar. 12, 1996, U.S. Provisional Application 60/002,936, filed Aug. 30, 1995, and U.S. Provisional 60/002,514 filed Aug. 18, 1995. These applications are incorporated herein in their entirety.

BACKGROUND OF THE INVENTION

Adrenomedullin (AM) is a recently identified hypotensive peptide initially isolated from human pheochromocytoma (K. Kitamura, et al., *Biochem. Biophys. Res. Commun.* 192, 553 (1993)). AM is generated from a 185 amino acid preprohormone through consecutive enzymatic cleavage and amidation. This process culminates in the liberation of a 52 amino acid bioactive peptide (T. Ishimitsu et al., *Biochem. Biophys. Res. Commun.* 203, 631 (1994)). AM and its gene-related peptide, PAMP, are the two known bioactive products generated from the post-translational enzymatic processing of the 185 amino acid-preproAM molecule (K. Kitamura, et al., *Biochem. Biophys. Res. Commun.* 192, 553 (1993); K. Kitamura, et al., *Biochem. Biophys. Res. Commun.* 194, 720 (1993); Kitamura, et al. *FEBS Lett.* 351, 35-37 (1994)).

The complete genomic infrastructure for human AM has recently been reported (Ishimitsu, et al., *Biochem Biophys Res Commun* 203:631-639 (1994)). The porcine (Kitamura, et al., *FEBS Lett* 338:306-310 (1994)) and rat (Sakata, et al., *Biochem Biophys Res Commun* 195:921-927 (1993)) AM complementary DNAs have also been cloned/sequenced and demonstrate high homology to the human counterpart. Human cDNA of AM has been cloned and mRNA expression identified in the adrenal glands, lung, kidney, and heart (K. Kitamura, et al., *Biochem. Biophys. Res. Commun.* 194, 720 (1993)). A high degree of base sequence homology has been found between AM mRNAs isolated from other mammalian species, including rat and porcine (J. Sakata, et al., *Biochem. Biophys. Res. Commun.* 195, 921 (1993); and K. Kitamura, et al., *FEBS Lett.* 338, 306 (1994)).

Data from several publications have demonstrated a wide range of tissues that express AM. Using RIA and Northern blot techniques, high levels of AM have been found in human plasma, adrenal medulla, heart atrium, lung, and kidney (Kitamura, et al., *Biochem Biophys Res Commun* 194:720-725 (1993); Kitamura, et al., *FEBS Lett* 341:288-290 (1994)), but, to date, the cell source of AM in these organs has not been identified.

Although both AM and PAMP are amidated peptides, they have been shown to mediate their vasodilatory effects through distinctly different receptor systems (T. Shimosawa, et al., *J. Clin. Invest.* 96, 1672 (1995)). AM stimulates adenyl cyclase activity, which elevates cAMP levels in smooth muscle cells. AM is structurally related to calcitonin gene-related peptide (CGRP), and its vasodilatory effect is inhibited by the CGRP antagonist, $CGRP_{8-37}$ (Y. Ishiyama, et al., *Eur. J. Pharmacol.* 241, 271 (1993); Ishizaka, et al., *Biochem. Biophys. Res. Commun.* 200, 642 (1994); J. A. Santago, et al., *Life Sci.* 55, 85 (1994); D. Y. Cheng, et al., *Life Sci.* 55, 251 (1994); H. Lippton, et al., *J. Appl. Physiol.* 76, 2154 (1994); Y. Shimekake, et al., *J. Biol. Chem.* 270, 4412 (1995)). Conversely, the fact that PAMP has no amino acid sequence homology to CGRP and its biological effects are not blocked by CGRP8-37 suggests the involvement of a separate receptor system (T. Shimosawa, et al., *J. Clin. Invest.* 96, 1672 (1995)). AM has also been implicated as an important regulator of renal function having natriuretic and diuretic action (T. Ebara, et al., *Eur. J. Pharmacol.* 263, 69 (1994); M. Jougasaki, et al., *Amer. J. Physiol.* 37, F657 (1995)). AM is also reported to be a potent bronchodilator, a regulator of certain central brain actions (vasopressor and antidipsogenic peptide), and a suppressor of aldosterone and adrenocorticotropin release (H. Kanazawa, et al., *Biochem. Biophys. Res. Commun.* 205, 251 (1994); H. Takahashi, et al., *Am. J. Hypertens.* 7, 478 (1994); T. A. Murphy and W. K. Samson, *Endocrinology* 136, 2459 (1995); T. Yamaguchi, K. Baba, Y. Doi, K. Yano, *Life Sci.* 56, 379 (1995); W. K. Samson, T. Murphy, D. A. Schell, *Endocrinology* 136, 2349 (1995)). Finally, AM has been shown to be expressed in a variety of human tumors of both neural and pulmonary lineage including ganglioblastoma/neuroblastoma (F. Satoh, et al., *J. Clin. Endocrinol. Metabol.* 80, 1750 (1995)), small cell lung cancer, adenocarcinoma, bronchoalveolar carcinoma, squamous cell carcinoma, and lung carcinoids (Martínez, et al., *Endocrinology* 136, 4099 (1995)). In an attempt to further study the distribution of AM in human tumors and determine its role in these malignant disorders, we used molecular, biochemical and in vitro techniques to analyze 59 human cancer cell lines from solid tumors and hemopoietic lineage.

AM's role as a vasodilatory agent has been extensively studied (C. Nuki et al., *Biochem. Biophys. Res. Commun.* 196, 245 (1993); Q. Hao et al., *Life Sci.* 54, 265 (1994); D. Y. Cheng et al., *Life Sci.*, 55, 251 (1994); C. J. Feng, B. Kang, A. D. Kaye, P. J. Kadowitz, B. D. Nossaman, *Life Sci.*, 433 (1994)). It acts through specific receptors in the plasma membrane to activate adenylate cyclase activity and modulate $Ca^{2+}$ flux in the target cells (S. Eguchi et al., *Endocrinology* 135, 2454 (1994); Y. Shimekake et al., *J. Biol. Chem.* 270, 4412 (1995)). These signal transduction pathways are involved in numerous physiological processes, including the regulation of hormone secretion. It is well established that regulation of intracellular cAMP modulates hormone release in the pancreas (Y. Korman, S. J. Bhathena, N. R. Voyles, H. K. Oie, L. Recant, *Diabetes* 34, 717 (1985); C. B. Wollheim, *Diabetes* 29, 74 (1980)). Since AM has been reported to influence the secretion rate of several hormones, including catecholamine (F. Kato et al., *J. Neurochem.* 64, 459 (1995)), adrenocorticotropin (W. K. Samson, T. Murphy, D. A. Schell, *Endocrinology* 136, 2349 (1995)), and aldosterone (T. Yamaguchi, K. Baba, Y. Doi, K. Yano, *Life Sci.* 56, 379 (1995)), we investigated the potential role of AM in regulating endocrine physiology of the pancreas.

Accordingly, due to the numerous therapeutic and diagnostic applications of AM peptides, there is an enormous medical and health requirement for potent, stable and selective AM peptides for therapeutic uses in the prevention, diagnosis, and treatment of AM related disease and conditions.

SUMMARY OF THE INVENTION

The present invention provides novel adrenomedullin (AM) peptides and AM antibodies useful in therapeutic, pharmacologic and physiologic compositions. In addition, the present invention provides methods of diagnosis, treatment and prevention of disease utilizing compositions comprising the novel AM peptides and antibodies. In particular, the therapeutic, diagnostic and preventative objects of the invention are described below.

It is an object of the present invention to provide methods for the prevention and treatment of cancers, in particular, adrenal, nervous system, lung, colon, ovarian, and breast cancers, by contacting the cancerous cells with an effective amount of AM peptides or antibodies of the present invention to inhibit the growth of cells. The AM peptides and antibodies of the present invention may also be used for the treatment of chondrosarcoma.

A further object of this invention is to provide AM peptides and antibodies for use as generic targets for intervention strategies to disrupt neoplastic transformation.

It is also an object of this invention to provide methods for diagnosing or monitoring diseases by measuring the levels of AM in a sample, wherein the presence or absence of AM indicates the existence of, or predisposition to, a disease. Examples of diseases which may be diagnosed or monitored by the methods of the present invention include, but are not limited to, diabetes, renal diseases, such as severe uremia; bone diseases, such as neoplastic disease; skin diseases; and blood related diseases, such as leukemia.

Another object of the present invention is to provide a method of preventing or treating type II diabetes using the peptides and antibodies of the present invention. Specifically, the AM peptides and antibodies of the present invention may be used to regulate insulin secretion and blood glucose metabolism.

Another object of the present invention is to provide AM peptides and antibodies for use in conditions related to pregnancy. In particular, a method for diagnosis and treatment of preeclampsia utilizing the AM peptides and antibodies of this invention is described. Further, AM peptides and antibodies may be used to promote fetal growth.

An additional object of the present invention is to provide methods of regulating activity in areas of the central nervous system by administering to a subject an effective amount of AM peptides or antibodies for the regulation of neurotransmission or neuron growth. A non-limiting example of a disease affecting the regulation of neurotransmission or neuron growth that may be treated by the AM peptides and antibodies of the present invention is Alzheimer's disease.

It is also an object of the present invention to provide a method of lessening or inhibiting the allergic response due to the degranulation of mast cells by administering antibodies to AM in an amount effective to lessen or inhibit the degranulation of mast cells.

It is also an object of the present invention to provide a method of treating bacterial and fungal infections by administering to a subject an amount of the novel peptides of the present invention effective to inhibit bacterial or fungal growth or prevent the infection.

Another object of the present invention is to provide a method of facilitating the healing of chaffed skin, skin lesions, wound repair, and surgical incisions by applying to the surface of the skin of a subject an amount of one or more of the novel AM peptides of the present invention effective to facilitate healing.

An additional object of the present invention is to provide means of promoting organ and bone development using the AM peptides and antibodies of the claimed invention.

The present invention further provides for pharmaceutical compositions comprising the novel AM peptides and antibodies of the present invention, and for pharmacological, therapeutic and diagnostic uses for the novel AM peptides and antibodies and pharmacological compositions comprising the same.

These and other objects of the present invention will become apparent in light of the accompanying disclosure and annexed figures.

BRIEF DESCRIPTION OF THE DRAWINGS

FIG. 1 sets forth a schematic drawing showing the structures of the human AM gene, mRNA, and preprohormone containing the two biologically active molecules, AM and pro-AM peptide (PAMP). The positions of the oligonucleotides and peptides synthesized are shown. Numbers in the gene and mRNA indicate base pairs from the initiation codon. Numbers in the protein correspond to amino acids. Data are modified from the report of Ishimitsu, et al., *Biochem Biophys Res Commun* 203:631-639 (1994).

FIG. 2 sets forth a titration curve for rabbit anti-PO72 immunogen (bleed 2343) binding to solid phase test peptides. A measurable antibody interaction was observed in AM, PO72, PO71, NPY, and CGRP. All other target peptides (PO70, gastrin-releasing peptide, glucagon-like peptide 1, vasoactive intestinal peptide, arginine vasopressin, GRF, cholecystokinin, gastrin, oxytocin, calcitonin, αMSH, and BSA) showed negligible binding.

FIGS. 4A-4D set forth a cross-section (magnification ×450) of a bronchiolus showing immunoreactivity to the anti-AM antiserum in the epithelium (FIG. 4A) and labeling of the AM mRNA after in situ RT-PCR (FIG. 4C). Absorption controls (FIG. 4B) and omission of the RT (FIG. 4D) confirmed the specificity of the staining.

FIGS. 5A-5D set forth photographs of a section through the adventitia layer of a bronchus showing a small nervous ganglion where the perykaria of the neurons and some nerves are immunostained (FIG. 5A), whereas a serial section treated with preabsorbed antiserum was negative (FIG. 5B). (Magnification ×450). Another ganglion appears labeled, at lower magnification (×120), after application of the in situ RT-PCR technique (FIG. 5C). Arrows point to blood vessels whose endothelial layers are clearly positive. Omission of primers in the PCR mixture gave negative staining (FIG. 5D).

FIGS. 6A and 6B set forth photographs of the detail of chondrocytes immunostained with anti-AM (FIG. 6A) and with the antiserum preabsorbed with PO72 (FIG. 6B). (Magnification ×700).

FIGS. 7A and 7B set forth photographs of alveolar macrophages labeled for AM mRNA after in situ RT-PCR (FIG. 7A) and negative control without reverse transcriptase (FIG. 7B). (Magnification ×450).

FIGS. 9A and 9B set forth photographs of cell line H820 (bronchioalveolar carcinoma) showing a cytoplasmic distribution of AM mRNA, as revealed by in situ RT-PCR (FIG. 9A), and a serial section demonstrating that the staining disappears when the reverse transcription step is omitted (FIG. 9B). (Magnification ×550)

FIGS. 10A and 10B set forth photographs of serial sections of an adenocarcinoma showing AM mRNA in the tumor cells by in situ RT-PCR (FIG. 10A) and immunocytochemistry (FIG. 10B). (Magnification ×550)

FIG. 11: FIG. 11 sets forth a chart indicating histamine release from rat mast cells.

FIGS. 12A and 12B indicate the effect of anti-AM MoAb on the growth of human tumor cell lines.

FIG. 13 sets forth a characterization of the monoclonal antibody MoAb-G6 showing binding to AM (○) and to two PO72 molecules: an in-house peptide (●) and a Peninsula peptide product (□). All other peptides: PO70, GRP, GLP1, VIP, AVP, GRF, CCK, amylin, gastrin, oxytocin, αMSH, pancreatic polypeptide, peptide YY, Taa-HoTH (Tabanus atratus Hypotrehalosemic Hormone), and BSA, showed negligible binding. Solid-phase assays were conducted using previously described methods (Cuttitta, et al., *Nature* 316, 823 (1985)).

FIGS. 14A and 14B show a representative sample of human tumor cell lines (H157, H720, MCF-7, OVCAR-3, SNUC-1) and normal human tissues (brain, lung, heart, adrenal) screened for AM mRNA and its translated protein. FIG. 14A is a Southern blot analysis and FIG. 14B is the ethidium bromide 1% agarose gel which demonstrates the predicted 410 bp product for AM mRNA as evaluated by RT-PCR analysis. FIG. 14C sets forth a Western blot analysis showing immunoreactive species of 18, 14, and 6 kDa when using a rabbit antiserum to AM. FIG. 14D is the antibody absorption control, which eliminated specific autoradio graphic band formation.

FIGS. 15A-15C set forth HPLC profile (FIG. 15A), solid phase plate assay (FIG. 15B), and Western blot analyses (FIGS. 15C-1 and C-2) of H720 conditioned medium (CM). FIG. 15A illustrates the fractionation of 5 L of H720 CM compared with the elution time of synthetic AM at 89.4 mm (arrow).

FIG. 16A shows the inhibitory effects of MoAb-G6 (●) compared with no effect from its mouse myeloma isotypic control, IgAκ (Sigma)(○). FIG. 16B shows that the effects of MoAb-G6 were overcome by the addition of synthetic AM (○) compared with the addition of AM alone (●). FIG. 16C indicates that cyclic AMP is activated with the addition of synthetic AM. FIG. 16D shows that specific receptor binding is higher for AM (○) than for PAMP (□) or PO72 (●). MTT (Carney, et al., *Proc. Natl. Acad Sci.* U.S.A. 79, 3185 (1981)) and receptor binding/cAMP assay techniques (T. W. Moody, et al., *Proc. Natl. Acad. Sci* U.S.A. 90, 4345 (1993)) are described elsewhere.

FIGS. 17A-17H: FIGS. 17A-17H set forth the distribution of adrenomedullin (AM) in the pancreas as shown by immunocytochemistry. FIG. 17A shows a rat pancreas with mild immunoreactivity throughout the entire islet of Langerhans and strongly stained cells in the periphery. FIG. 17B sets forth Hamster pancreas which displays a similar pattern. FIG. 17C sets forth dog pancreas containing numerous immunoreactive cells scattered throughout the parenchyma. FIG. 17D depicts the immunoreactivity in ductal systems of guinea pig pancreas. FIG. 17E shows serial sections of hamster pancreas immunostained for AM and FIG. 17F shows pancreatic polypeptide colocalization of both immunoreactivities (arrows). FIG. 17G sets forth double immunogold staining by electron microscopy showing colocalization of AM (small gold particles, 10 nm) and pancreatic polypeptide (large gold particles, 20 nm) in the cell situated to the left. FIG. 17H shows detail of a D-cell showing some immunoreactivity for AM (large particles) in the somatostatin-containing (small particles) secretory granules.

(FIG. 18A) Increasing concentration of AM reduces insulin secretion in the presence (○) or absence (●) of MoAb-G6 antibody. Note dramatic increase in insulin secretion mediated by the antibody. (FIG. 18B)

FIG. 19A shows a Southern blot for AM in six cell lines expressing insulin and in human adrenal and pancreas mRNA. FIG. 19B shows the same gel as seen by UV before transfer.

FIGS. 20A and 20B: Glucose tolerance tests were performed on Sprague-Dawley rats (250 to 300 g) in the presence (○) or absence (●) of AM. Circulating glucose is shown between 0 and 60 minutes (FIG. 20A) and between 0 and 6 hours (FIG. 20B) after feeding.

FIG. 21 sets forth in panels A-I the localization of AM mRNA and immunoreactivity in various organs of different species. Panel A shows mRNA for AM detected by in situ RT-PCR in the epithelial cells of the rat trachea. Panel B sets forth guinea pig trachea displaying a strong immunoreactivity to the AM antibody, specially in the apical region. Panel C depicts a *Xenopus* respiratory tract, with intense immunostaining in the supranuclear region. Panel D shows *Xenopus* integument with AM immunoreactivity concentrated in the unicellular glands of the epidermis (two of which appear in this figure). The dark spot to the left is a chromatophore. Panel E shows skin of a 16-day old mouse embryo. An intense immunoreactivity to AM is observed in the epidermis and in the subjacent developing muscles. Panel F sets forth a hamster uterus showing immunostaining for AM in both the lining epithelium and the glands. Panel G shows a small salivary gland found in the hamster tongue. Discrete secretory cells store the AM-like material. Panel H shows rat duodenum with intensely immunostained Brunner's glands. Panel I shows a section of cat colon containing an AM-positive endocrine cell.

FIG. 22 indicates the effect of AM and PAMP on the inhibition of growth of *E. coli*. AM demonstrated higher growth inhibitory activity than albumin (Alb) (negative control) (*, p=0.03), PO70 (¶, p=0.04), PO71 (¶, p=0.006), and PO72 (¶, p=0.03). Magainin (M) exerted greater inhibitory activity against *E. coli* than did AM (* ¶ § †, p=0.03) and PAMP (§ †, p=0.009). Data were compiled from 14 experiments.

FIGS. 23A and 23B set forth the antimicrobial activity of AM and PAMP. Inhibition of growth is shown at 6 hours (FIG. 23A) and 24 hours (FIG. 23B).

FIG. 24 indicates the effect of AM on the germination of *C. albicans*.

FIG. 25: FIG. 25 sets forth the distribution of amphipathic regions for AM and PAMP as calculated for a-helix/b-sheet angle parameters (Eisenberg), and the helical wheel projection display for AM (FIG. 25A) and PAMP (FIG. 25B) (DNASTAR).

FIGS. 26A-26D: FIG. 26 sets forth a representative sample of human tumor cell lines and normal human tissues screened for AM and AM-R. Southern blot analysis demonstrates the predicted 410 bp product for AM (A) and a 471 bp product for AM-R mRNA (B) after RT-PCR amplification. (C) Western blot analysis of cell extracts shows immunoreactive species of 18, 14, and 6 kDa when using a rabbit antiserum to AM. In addition, there is a 22 kDa immunoreactive entity that may be attributed to post-translational processing. (D) The absorption control was negative.

FIG. 27 sets forth the immunohistochemical and in situ RT-PCR analysis of human cancer cell lines for AM. (A) Immunohistochemical analysis for AM in SCLC H774 and (B) ovarian carcinoma cell line NIH: Ovcar-3. Note the peripheral distribution of AM immunoreactivity in H774 colonies. (C) In situ RT-PCR for AM mRNA in carcinoid cell line H720 and (D) negative control in a serial section where primers were substituted by water in the PCR mixture.

FIG. 28 sets forth the growth effects of AM. A representative human tumor cell line, MCF-7, was used to show the growth effects, receptor binding and cAMP variation by AM under serum-free, hormone-free conditions. (A) Inhibitory effects of MoAb-G6 (●) compared with no effect from its mouse myeloma isotypic control, IgA$_K$ (○). (B) Effects of MoAb-G6 were overcome by the addition of synthetic AM (○) compared with the addition of AM alone (●).

DETAILED DESCRIPTION OP THE INVENTION

Figure 2:
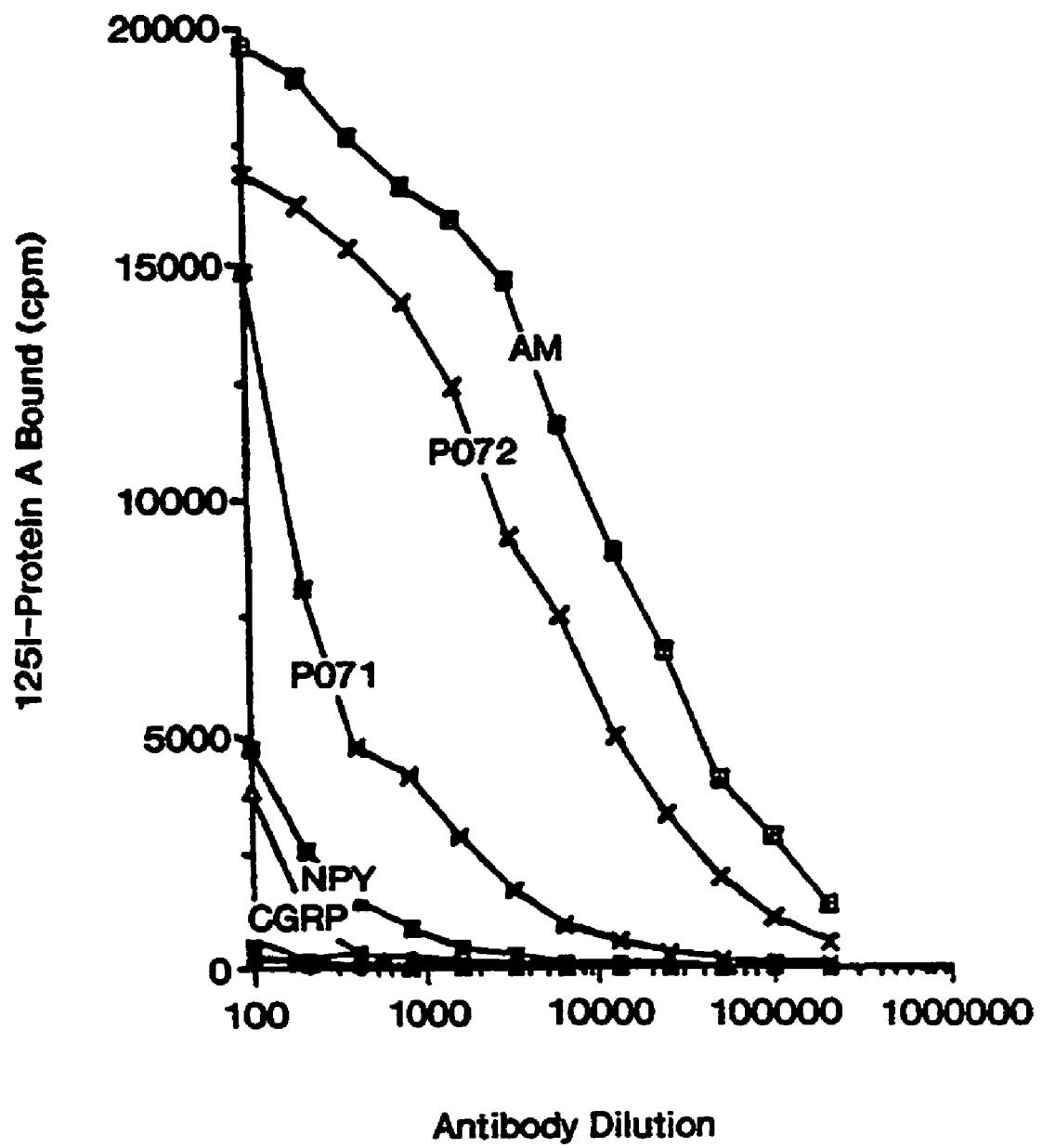
FIG. 2.

The present invention generally provides novel adrenomedullin (AM) peptides and AM antibodies, pharmaceutical compositions comprising said peptides and antibodies, and their use as pharmaceutically active agents.

Specifically, the present invention relates to the following novel AM peptides:

| | |
|---|---|
| PO70 (YY-PreproAM$_{34-41}$) | Y-Y-W-N-K-W-A-L-S-R-NH$_2$ (SEQ. ID. NO. 1) |
| PO71 (YGG-PreproAM$_{122-131}$) | Y-G-G-H-Q-I-Y-Q-F-T-D-K-D-NH$_2$ (SEQ. ID. NO. 2) |
| PO72 (PreproAM$_{116-146}$) | T-V-Q-K-L-A-H-Q-I-Y-Q-F-T-D-K-D-K-D-N-V-A-P-R-S-K-I-S-P-Q-G-Y-NH$_2$ (SEQ. ID. NO. 3) |
| Sense primer (AM 94-114) | 5'-AAG-AAG-TGG-AAT-AAG-TGG GCT-3' (SEQ. ID. NO. 4) |
| Antisense primer) (AM 444-464) | 5'-TGG-CTT-AGA-AGA-CAC-CAG-AGT-3' (SEQ. ID. NO. 5) |
| Antisense probe (AM 289-309) | 5'-CTG-GAA-GTT-GTT-CAT-GCT-CTG-3' (SEQ. ID. NO. 6) |
| Proadrenomedullin N-terminal 20 peptide (PAMP-20) | A-R-L-D-V-A-S-E-F-R-K-K-W-N-K-W-A-L-S-R-NH$_2$ (SEQ. ID. NO. 7) |

These peptides and others may be used to generate antibodies, whether polyclonal or monoclonal, which can then be used to prepare antibody containing compositions used in the methods of the present invention. The antibodies are prepared via techniques well known to those having ordinary skill in the art. In particular, monoclonal antibodies to peptide PO72 are particularly useful in the practice of the present invention.

The AM peptides and antibodies of the present invention are useful in a variety of therapeutic and diagnostic settings. These are described with more specificity below.

(1) Expression of Adrenomedullin in Normal Human Lung and Pulmonary Tumors

Studies were carried out to localize the expression sites for AM in lung, as a first step to identification of novel functions for the AM peptide. The localization of AM in the endothelium of the blood vessels would be expected to be due to the involvement of the AM peptide in blood pressure regulation (Nuki, et al., *Biochem Biophys Res Commun* 196:245-251 (1993); Ishiyama, et al., *Eur J Pharmacol* 241:271-273 (1993); Perret, et al., *Life Sci* 53:PL377-PL379 (1993); Lippton, et al., *Life Sci* 54:PL409-PL412 (1994); Santiago, et al., *Eur J. Pharmacol* 272:115-118 (1995); Lippton, et al., *J Appl Physiol* 76:2154-2156 (1994); Sugo, et al., *Biochem Biophys Res Commun* 201:1160-1166 (1994)), and the expression of AM in smooth muscle cells has been previously reported (Sugo, et al., *Biochem Biophys Res Commun* 203:719-726 (1994)). The expression of AM in various pulmonary cell types implicates potential new roles for this molecule.

The abundant presence of AM at the apical interface of columnar epithelium with external environment suggests that AM could be secreted to the pulmonary lumen. Usually the functions of the ciliated cells of the bronchial epithelium are supposed to be restricted to the mechanical transport of the mucous layer through ciliary beat, but other regulatory peptides, such as endothelins, have been described in this cell type (Giaid, et al., *Am J Respir Cell Mol Biol* 4:50-56 (1990)). The expression of AM in the lining epithelium and macrophages points to a possible protective action against pathogens, similar to that observed for other peptides, such as the magainins present in the airway epithelium (Diamond, et al., *Proc Natl Acad Sci USA* 90:4596-4600 (1993)) or the tracheal antimicrobial peptide (Diamond, et al., *Proc Natl Acad Sci USA* 88:3952-3956 (1991)).

The distribution of AM in normal lung described herein colocalizes with the pattern previously reported for the peptide-amidating enzymes (Saldise, et al., *J. Histochem. Cytochem.* 1996). In this reference, it was postulated the potential existence of yet unknown amidated peptides concomitantly expressed at the same sites of enzyme production. The studies herein suggest that AM may be one of those predicted peptides. It has been demonstrated that amidation is important for AM activity; the amidated form of AM has 50 times greater affinity for the receptor than the nonamidated form (Eguchi, et al., *Endocrinology* 135:2454-2458 (1994)).

To characterize the functions of AM in normal tissues, the distribution of AM was studied in normal and malignant lung using immunocytochemical techniques to localize the peptide in in situ reverse transcriptase-polymerase chain reaction (RT-PCR) to study the expression of its messenger RNA (mRNA) in formalin-fixed paraffin-embedded specimens.

(2) Human AM/AM-R mRNA Expression in Normal and Malignant Cells

Figure 14A:
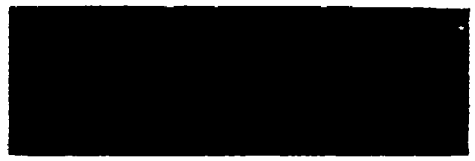
FIGS. 14A, 14B, 14C and 14D.
Figure 14B:
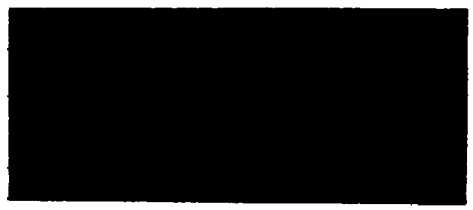

RT-PCR was used to evaluate AM ligand and receptor mRNA in a variety of cancer cell lines of diverse origin and normal human tissues (Table 3, FIGS. 14A and 14B). Sense and antisense primers were derived from published human cDNA sequence (Kitamura, K., et al., Biochem. Biophys. Res. Commun. 194, 720 (1993)) based on computer analysis from the primer select DNAstar program. The resulting 410 bp and 471 bp RT-PCR products for AM and AM-R mRNA were confirmed by Southern blotting with antisense nested probes. Cloned product for normal human adrenal gland and H720 was further verified as an authentic fragment of the AM message by nucleotide sequencing, showing homology for more than 200 bp in either direction using sequencing primers at the Sp6 and T7 promoter regions. The majority of neoplastic cell lines tested (55/58, 95%) were shown to express AM message (see FIGS. 14A and 14B, and Table 3). FIGS. 14A and 14B show a representative sample of human tumor cell lines (H157, H720, MCF-7, OVCAR-3, SNUC-1) and normal human tissues (brain, lung, heart, adrenal) screened for AM mRNA and its translated protein. MoAb-G6 was absorbed with the addition of 10 µg/mL of synthetic homolog PO72.

AM mRNA was not found in the following cancer cell lines: H69c (SCLC), H23 (adenocarcinoma) and H460 (large cell carcinoma). The fact that certain tissues do not express AM by Northern blot evaluation does not preclude its presence as demonstrated by RT-PCR (Table 4). For example, a heterogenous tissue, such as brain, showed AM expression by RT-PCR, but not by Northern analysis. Though less extensively studied, similar data were observed for AM-R mRNA ($^{27}/_{36}$, 75%), (Table 3) showing colocalization of ligand and receptor message in normal tissue and in 75% of the neoplastic cell lines (FIGS. 14A-14D and FIGS. 26A-26B). The data demonstrates AM-R mRNA, by RT-PCR, in the following normal tissues: brain, heart, lung and adrenal gland (FIG. 26B).

AM has been shown to induce cAMP production in the target cells (Ishizaka, et al., *Biochem Biophys Res Commun* 200:642-646 (1994)). It has been previously observed that most of the peptide hormones able to induce cAMP synthesis act as modulators of cell growth (Ishizuka, et al., *Cancer Res* 54:2129-2135 (1994); Moody, et al., *Proc Natl Acad Sci USA* 90:4345-4349 (1993)); thus, AM could also function as a growth regulator of tumor proliferation. In addition, blood supply is a critical factor for the successful implantation of tumor cells at distant metastatic sites, and many neoplasms induce angiogenesis (Weinstat-Saslow, et al., *FASEB J* 8:401-407 (1994)). An alternative or synergistic survival method might be the production and secretion of vasodilatory substances such as AM to enhance the availability of nutrient factors to the tumor bed.

The regional distribution of AM, a regulatory peptide present in the airway epithelium and in tumors historically classified as nonendocrine, and the colocalization with one of the posttranslational processing enzymes required for synthesis of the active peptide, led us to reconsider the concept of "endocrine." As new regulatory peptides are discovered, new cell types enter the arena of endocrinology. Similar trends have previously occurred with the gastrointestinal system (Bloom, et al., *Adv Clin Chem* 21:177-244 (1980)) and endothelial cells (Vane, et al., *J Physiol Pharmacol* 43:195-207 (1992)). AM expression challenges our notions of restricted expression of neuroendocrine features and highlights the pluripotency of the airway epithelium.

(3) Production and Secretion of AM Peptide by Human Tumor Cell Lines

Select cancer cell lines, as shown in FIG. 26, were adapted to grow under R0 conditions and the resulting whole cell lysates from such lines were examined for AM immunoreactivity by Western blot analysis using a previously characterized rabbit antiserum (Martinez, A., et al., *Endocrinology* 136:4099-4105 (1995)). FIG. 26C illustrates the electrophoretic profile of AM-like immunoreactive peptides identified.

Figure 15A:
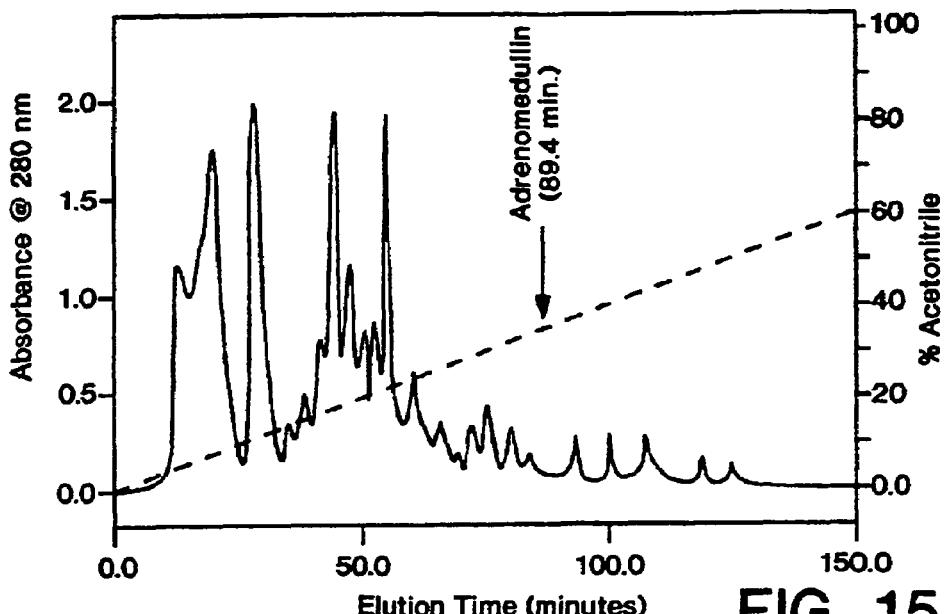
FIGS. 15A, 15B and 15C.
Figure 15B:
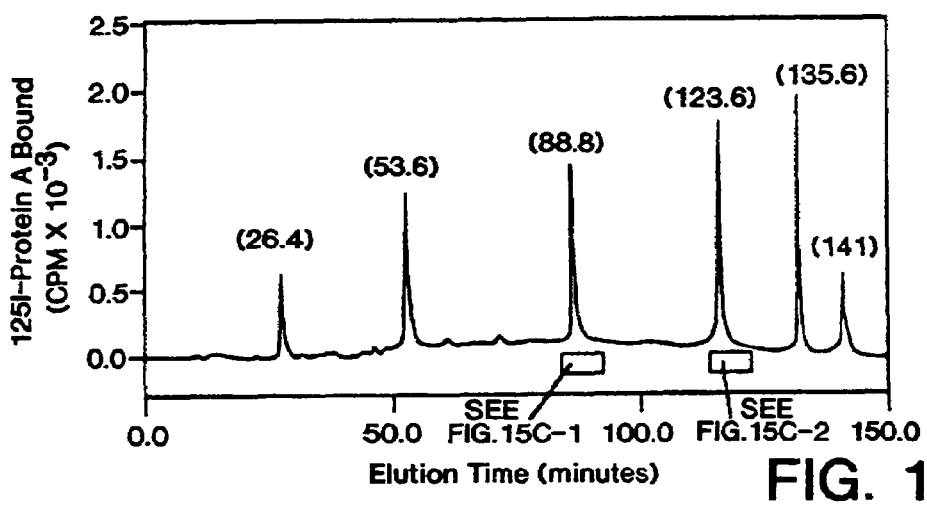
Figures 1, 2, 15C:
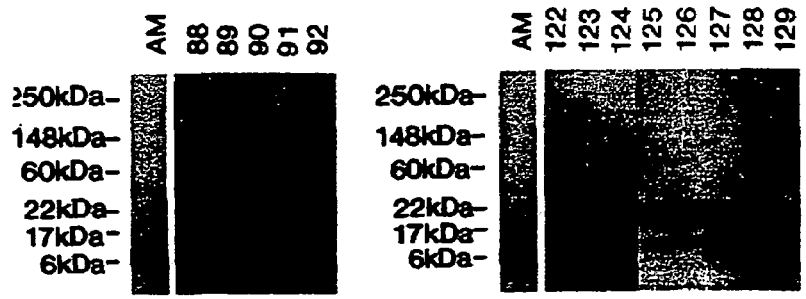
FIG. 1.
Figure 16A:
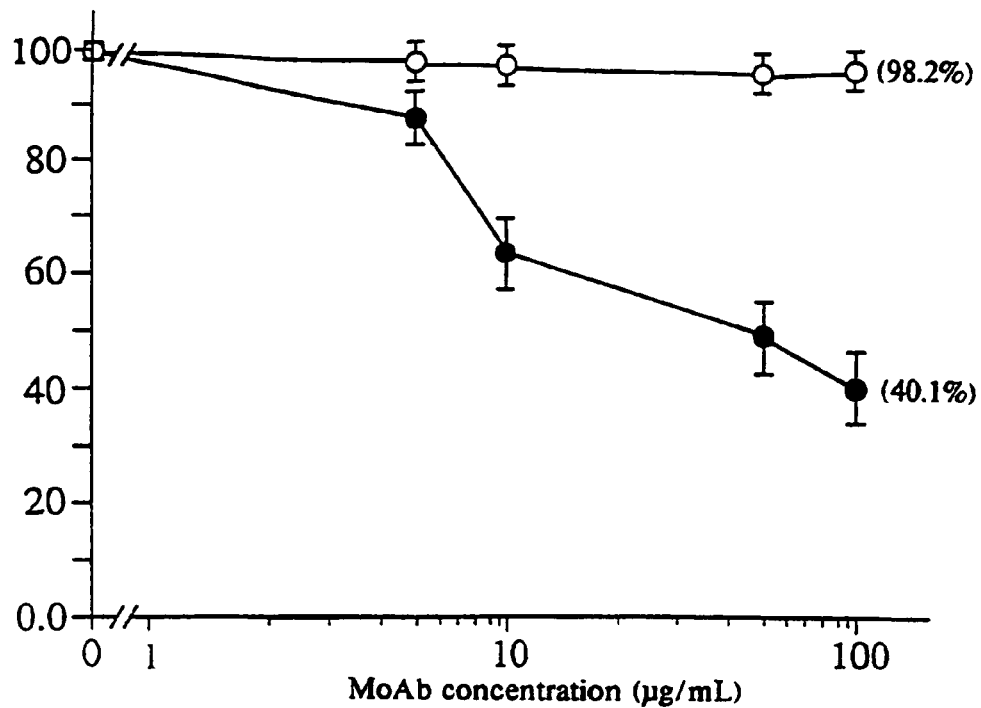
FIGS. 16A, 16B, 16C and 16D: A representative human tumor cell line, MCF-7, was used to show the growth effects, cAMP activity and receptor binding by AM under serumfree, hormone-free conditions.
Figure 16B:
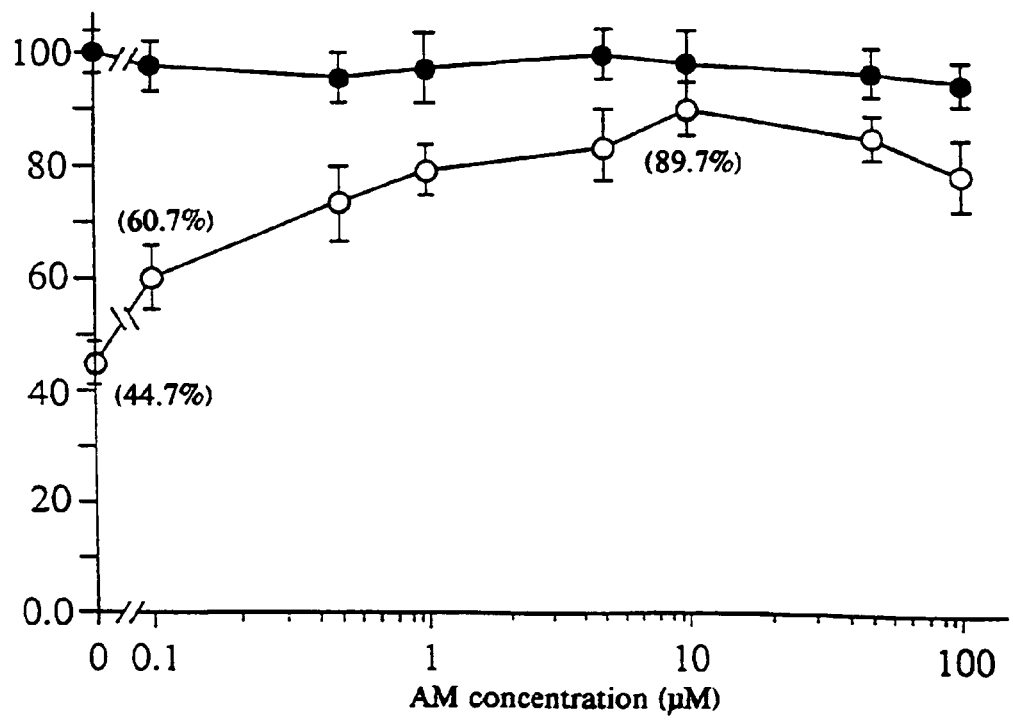
Figure 16C:
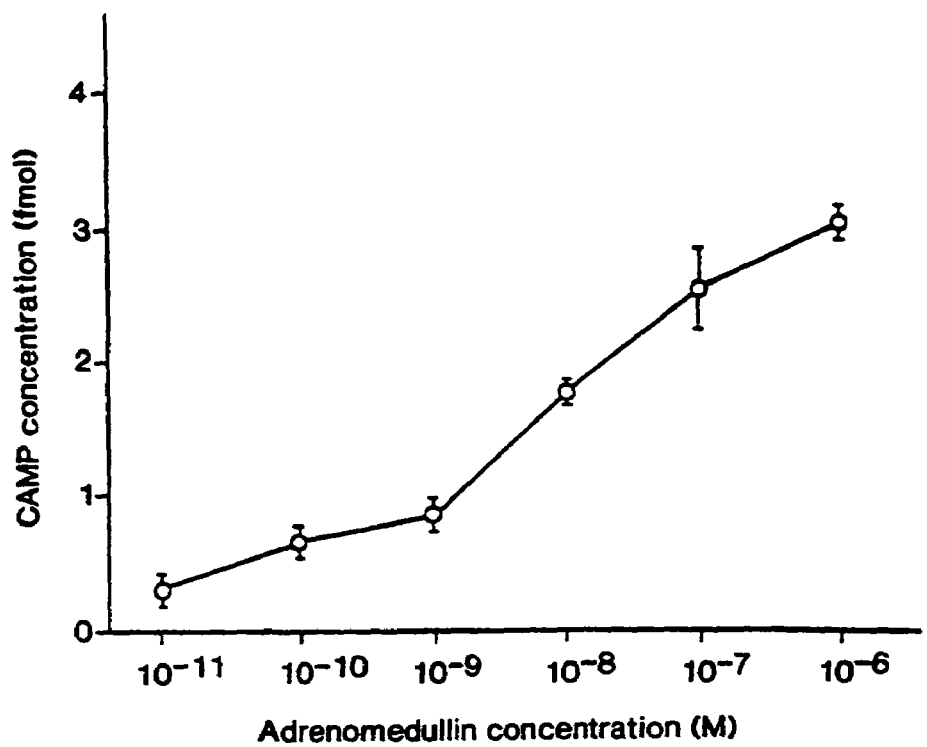
Figure 16D:
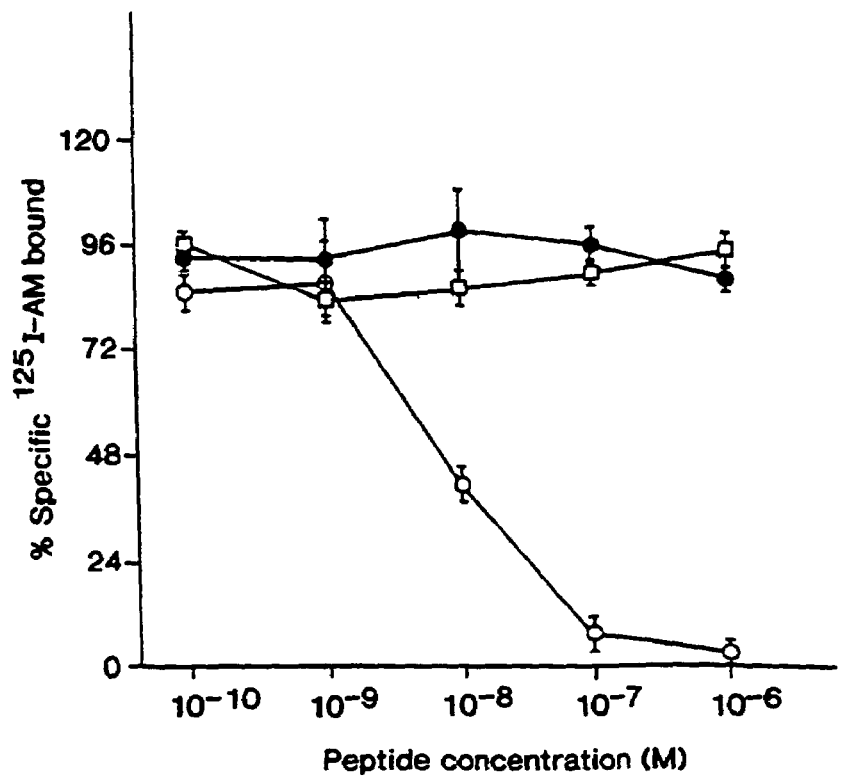

Molecular weight species of 18, 14 and 6 kDA were identified and presumably represent AM precursor, processed intermediates, and the authentic peptide, respectively. There is also a 22 kDa immunoreactive species in two cancer cell lines, H720 and MCF-7. The specificity of the immune-detection assay was confirmed by an antibody absorption control, which eliminated the specific bands (FIG. 26D). To further corroborate the expression of authentic ASM by tumor cells, HPLC fractions were analyzed of ROCM from the lung carcinoid cell line NCI-H720. Column retintate contained AM-like immunoreactivity having an elution time consistent with the synthetic peptide (≈89 min) (FIGS. 15A-15B). In addition, immunoblot analysis of consecutive HPLC fractions within the 88 to 92 min region revealed a major 6 kDa immunoreactive band, while the 124 to 129 min fractions expressed both the 18 and 14 kDa entity (FIG. 15C). Additional immunoreactive peaks were identified at 26.4 min., 53.6 min., and 135.6 min., but they were not further characterized (FIG. 15).

(4) AM Regulates Human Tumor Cell Proliferation

Figure 27A:
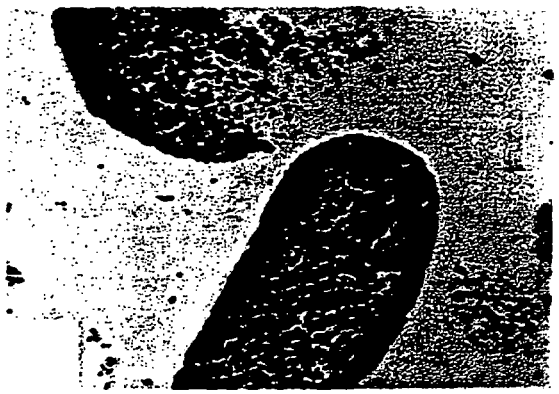
FIGS. 27A-27D.
Figure 27B:
Figure 27C:
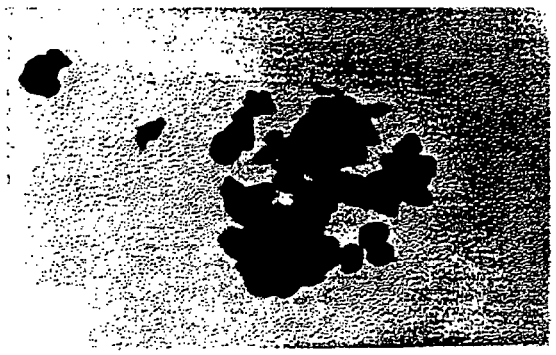
Figure 27D:
Figure 28A:
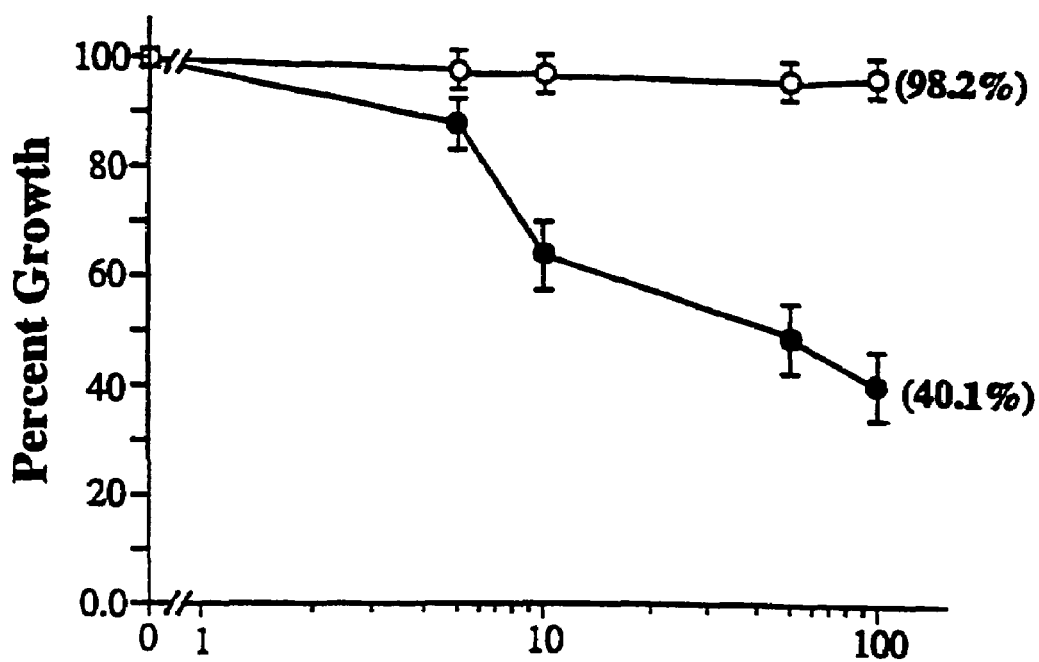
FIGS. 28A and 28B.
Figure 28B:
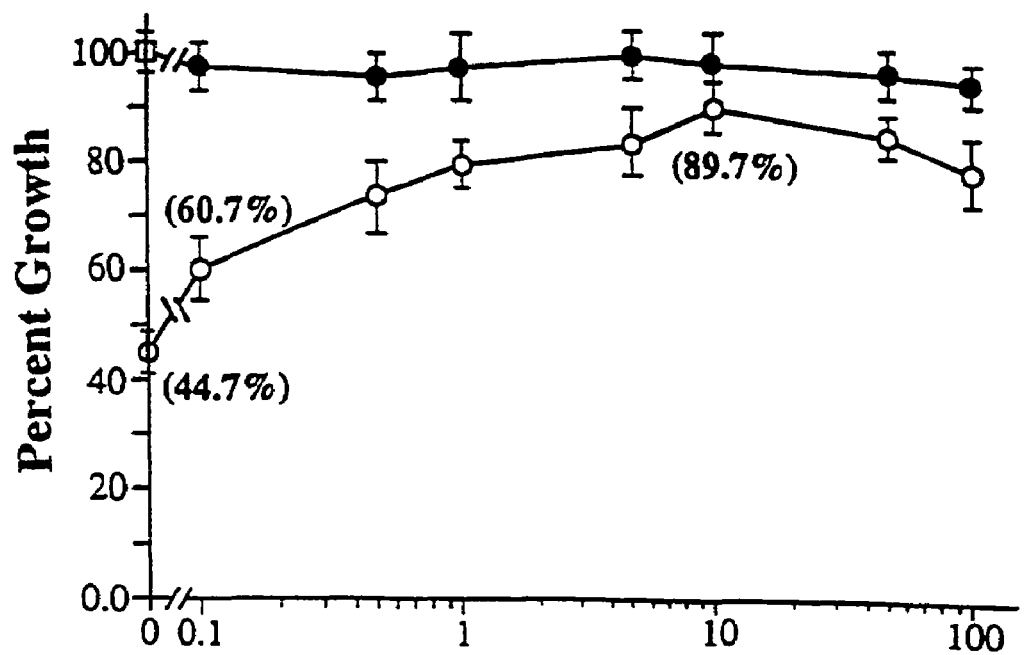

Results obtained by immunohistochemical (IHC) and in situ RT-PCR examination of paraffin-embedded RO-adapted cell lines were consistent with previously reported data on normal lung and pathological lung specimens (Martinez, A., et al., *Endocrinology* 136:4099-4105 (1995)). Human tumor cell lines evaluated show AM expression by IHC and in situ RT-PCR, as shown in FIG. 27. It is interesting to note that AM expression in SCLC H774 demonstrates the highest intensity of staining in the outer layers (proliferative zones) of individual colonies, a finding that could implicate AM in growth regulation (FIG. 27A). Consistent with this idea was the fact that AM had been shown to elevate cAMP, a signal transduction pathway known to modulate cellular growth (Ishiyama, Y., et al., *Eur. J. Pharmacol.* 241:271-273 (1993)). To further investigate this suspected phenomenon, MTT assay techniques were used to examine the effects of AM on the growth of several diverse tumor cell lines (lung, colon, breast, brain, and ovary). Exogenous addition of AM (with a final concentration range between 0.1 µM to 100 µM) to RO-grown cell cultures was ineffective in stimulating growth, although there was some non-specific toxicity at the higher range. Since the test cells were known to produce authentic AM peptide, we assumed that this inability to stimulate growth with extrinsic ligand could possibly mean that the cells has already achieved maximal proliferative effects using their own AM.

Figure 12A:
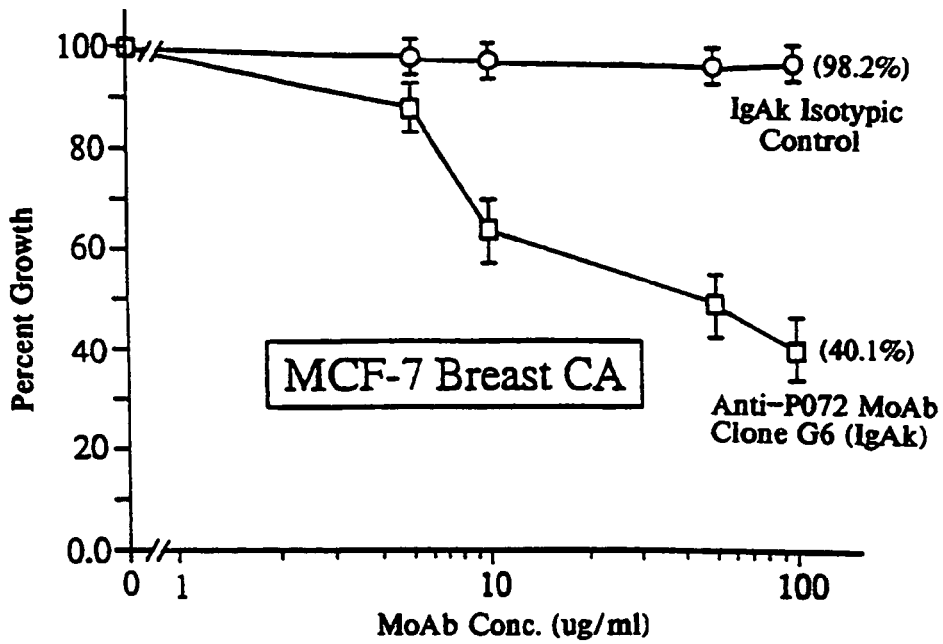
FIGS. 12A and 12B.
Figure 12B:
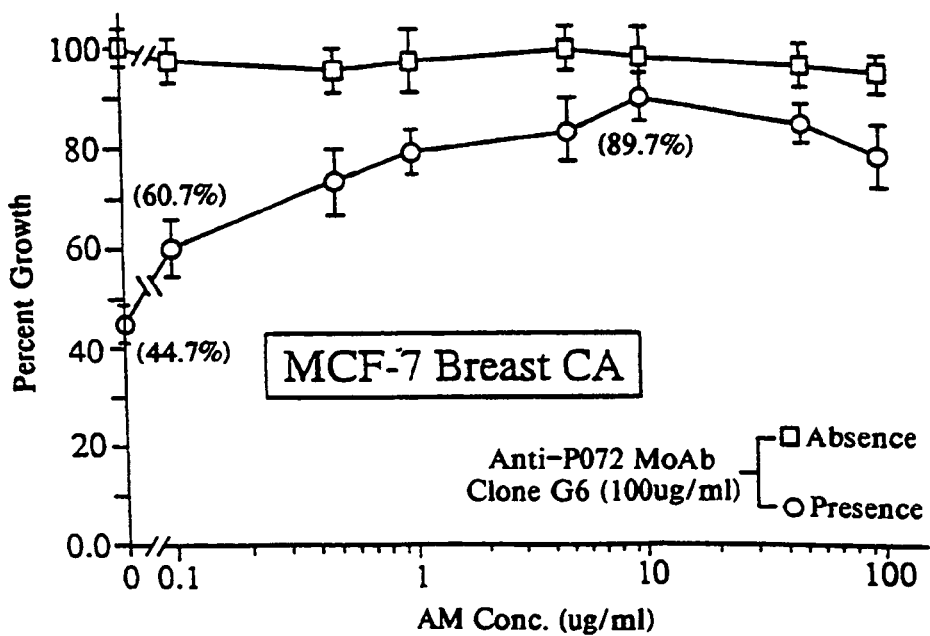
Figure 13:
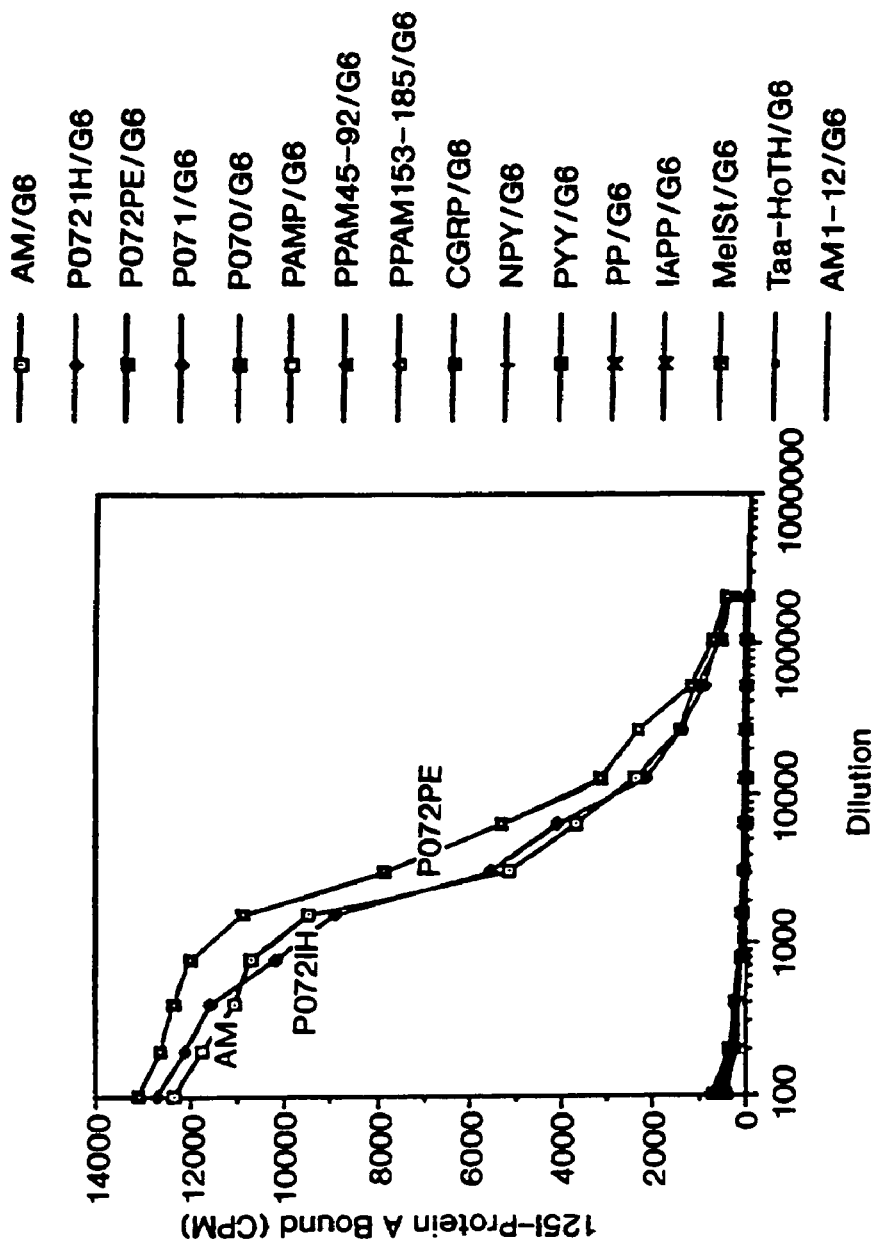
FIG. 13.

To verify this hypothesis, MoAb-G6 was used to block the biological activity of endogenous AM. During the characterization of MoAb-G6, it was demonstrated that it did not cross-react with other known tyrosine amide peptides or with the structurally related CGRP and amylin (FIG. 13). The MTT assay was used to evaluate MoAb-G6 for its effect on the growth of 5 human tumor cell lines (NC1—H157, NC1—H720, MCF-7, NIH:OVCAR-3 and SNUC-1), and a dose dependent suppression was observed in 4 out of them (see Table 5). At the highest concentration of MoAb-G6 used (100 µg/ml), a consistent 25-6% growth suppression was observed among cancer cell lines examined with the exception of SNUC-1. In the colon cancer cell line, SNUC-1, AM-R expression is undetectable by RT-PCR (FIG. 26B), which may be the reason MoAb-G6 had very little effect on its growth. Representative data for MCF-7 are depicted in FIG. 12A, which shows that an isotypic control mouse myeloma protein (TEPC 15, IgA$_K$ Sigma) was ineffective in blocking growth over the same dose range. MoAb-G6 induced inhibition of tumor cell growth was abolished by exogenous addition of AM, with maximal recovery at 10 µM, thus verifying the specificity of growth suppression by the neutralizing antibody (FIG. 12B).

(5) AM Receptors are Present in Human Tumor cell Lines and AM Increases Intracellular cAMP In addition to the RT-PCR analysis of the AM-R mRNA (FIG. 26B), the cAMP response to synthetic AM and $^{125}$I-AM binding was determined to demonstrate the presence of functional AM receptors in responding tumor cell lines. Several cancer lines demonstrated selective binding of $^{125}$I-AM, which was not competitively blocked by the synthetic homolog PO072 or the gene-related peptide PAMP, as shown by representative data for breast cancer cell line MCF-7 (not shown). The data shows that specific binding is inhibited by AM in a dose-dependent manner with an $IC_{50}$ of 10 nM. As illustrated for MCF-7, AM binding to this receptor induced a rapid increase in cellular cAMP over a dose range of 10 μM to 1 μM (not shown). In contrast, PO72 and PAMP had no effect on cAMP.

(6) The Role of Adrenomedullin as an Autocrine Growth Factor for Human Breast Epithelial Cells During Development and Carcinogenesis AM mRNA expression was identified in 4/4 normal and 6/6 normal malignant breast cells using RT-PCR. Immunohistochemical and in situ PCR analysis of paraffin-embedded tissue localized AM expression preferentially to the apical areas of epithelial cells in 11/11 normal specimens. Similar analysis on malignant tissue demonstrated AM in 10/12 breast CA. To further identify the potential role of AM in breast CA, the tumor cell line MCF-7 was analyzed, which was adapted to grow in serum-free/hormone-free medium. When evaluated by SDS-PAGE/immuno blot, these cells were shown to express immunoreactive AM-like species of 18 kiloDaltons (kDa), 14 kDa, 9 kDa, and 6 kDa. These various molecular weight entities are thought to represent the precursor, authentic peptide, and process intermediates of AM. In addition, the inventors have shown that MCF-7 expresses high affinity receptors for this ligand (Kd≈2 nM) and response to exogenous AM by increasing intracellular cAMP resulting in elevated clonal growth in soft agar assays. The anti-AM monoclonal antibody MoAb-G6 was shown to induce a dose-dependent inhibition of MCF-7 growth in liquid culture. An isotopic control mouse myeloma protein (IgAK) was ineffective over the same dose range. Mo-Ab-G6 growth inhibition was abrogated by exogenous AM. The collective data implicates AM as a potential autocrine growth factor involved in normal breast development and carcinogenesis.

(7) Modulation of Adrenomedullin in Severe Preeclampsia

AM is a potent long-acting hypotensive peptide that is present in human plasma at considerable concentrations and is proposed to be a new circulating hormone participating in blood pressure control. Specifically, AM is thought to have a role in preeclampsia. Preeclampsia is a condition associated with high blood pressure and spontaneous abortion. Hypertension complicates 7% of pregnancies and preeclampsia is responsible for 70% of all hypertension in pregnancies. Currently, there are no diagnostic tools available to identify women who may be likely candidates for developing preeclampsia. Accordingly, specific diagnostic tools and treatments are required.

To further understand the etiopathogenesis of preeclampsia and the associated hypertension, the cellular localization of AM in sections of formalin-fixed paraffin embedded placentas of normal and preeclamptic patients was evaluated. Established immunohistochemical techniques were used with a well characterized rabbit polyclonal antibody specific to AM and a streptavadin-peroxidase detection system (Vector laboratories). Significantly decreased immunoreactive AM was found in the placentas of patients with severe preeclampsia in comparison to the immunostaining exhibited by the placentas of normal patients. These results suggest that AM may play a role in the regulation of placental perfusion and the cardiovascular system during pregnancy and that dysregulation may be associated with preeclampsia.

The present invention provides for novel AM peptides which are useful in the diagnosis and treatment of preeclampsia, thereby overcoming the inadequacies of the current state of the art. Furthermore, the novel AM peptides and antibodies of the present invention allow for early detection of a predisposition of a subject to a particular disease state.

(8) Stinulation of Adrenomedullin Protein Levels During Estrogen-Induced Growth of the Uterus and Vagina Increasing evidence suggests that estrogen mediates its effects on the growth and differentiation of the reproductive tract in part due to the regulation of autocrine/paracrine factors. Occurring within minutes after estrogen treatment is the induction of hyperemia, increased vascular permeability, and edema, which is followed later by synchronized growth of the uterine epithelium. Despite the dramatic nature of these physiological changes, relatively little is known concerning the mechanism by which estrogen brings them about. In light of the known vascular effects of AM, the cell-specific and temporal regulation of AM protein levels following a single treatment with a physiological dose of estrogen using established immunohistochemical techniques.

Estrogen treatment induced in a time-dependent manner distinctive epithelial cell-specific localization of AM protein in both the uterus and vagina (evident at the earliest timepoint investigated, 12 hrs). The induction of AM in the uterine epithelium was transient and fell to control levels within 24 hours after estrogen exposure; whereas, marked vaginal expression was maintained in the epithelium for up to 48 hours post-treatment. Smooth muscle cells in both organs showed considerable immunoreactivity that did not seem to fluctuate with estrogen treatment. These results indicate that estrogen stimulates AM protein levels in the epithelium of the uterus and vagina in a time-dependent and organ-specific manner. The induction of AM occurs prior to the initiation of DNA synthesis; thus AM may play a role in the estrogen action by increasing vascular permeability and perfusion to the uterus and vagina that is necessary to provide conditions favorable for synchronized growth.

(9) The Role of Adrenomedullin in Ovarian Function.

Dynamic changes in blood vessel growth and vascular flow occurs in the ovary during the periovulatory and luteal phases. The initiation of neovascularization in selected follicles has been shown to parallel the appearance of various differentiation markers such as aromatase, LH receptor, and inhibin subunits. In addition, the new capillaries that develop during the formation of the corpus luteum are known to be highly permeable, which facilitates the delivery of large protein molecules such as low density lipoproteins that transport cholesterol required for progesterone biosynthesis. In light of the known role of AM in regulation of vascular flow, the specific aim of the studies herein was to examine the cell and stage-specific expression of AM protein in the rat ovary by immunohistochemistry. The ovary demonstrated prominent AM protein expression. AM was immunolocalized to capillary endothelial cells, smooth muscle cells of major vessels, germinal epithelium, thecal cells, in scattered granulosa cells within the cumulus oophorus of mature antral follicles, and to many cells within the corposa lutea. The most striking immunoreactivity for AM in the ovary was exhibited by the corpus lutea where the more mature corpus lutea demonstrated the greatest number of positive staining cells. In addition, intense localization of AM was found associated with the apical surface of the oviductal epithelium. The prominent expression of AM in the corpus lutea, in the mature follicles, and the oviduct, implicates AM as a potential contributor to ovarian steroidogenesis, ovulation, and possibly to providing an environment within the oviduct conducive for implantation, fertilization and early development. The presence of AM protein in different reproductive tissues under the influence of steroid and gonadotrophin hormones suggests that AM may play a pivotal role in reproduction possibly by ensuring the acquisition of an adequate blood supply need to maintain rapid growth and/or differentiated function.

(10) The Role of Adrenomedullin in Neurotransmission

The presence of AM in the neurons of the pulmonary intrinsic nervous system points to a possible involvement in neurotransmission. A similar function has been assigned to CGRP, a molecule with which AM shares some structural homology (Kitamura, et al., *Biochem Biophys Res Commun* 192:553-560 (1993)) and which is particularly abundant in the lung (Springall, et al., *J Auton Nerv Syst* 20:155-166 (1987)). Recently, some effects on blood pressure regulation were described after injection of AM in the rat central nervous system (Takahashi, et al., *Am J Hypertens* 7:478-482 (1994)).

(11) The Role of Adrenomedullin and its Gene-Related Peptide, Proadrenamedullin Peptide-20 (PAMP-20), in the Induction of IgE Independent Degranulation of Mast Cells Mast cells are intimately involved in allergic responses. They contain granules which in turn release histamines when degranulation occurs. Mast cells stained and observed immunohistochemically show the presence of AM in the granules and murine mast cell lines produce mRNA for AM. The ability of the mast cell to produce their own degranulation agent allows for autocrine degranulation or recruitment. Thus, the release of AM by a mast cell which has been primed (expresses IgE for an antigen) and then activated due to presentation of the antigen (i.e. degranulation occurs) results in the release of AM into the system with AM being able to cause the degranulation of mast cells which have not been primed (increases the allergic response).

AM and PAMP-20 are basic peptide amides with respective isoelectric points of $pI_{AM}$=10.2 and $pI_{PAMP}$=10.1. It has previously been demonstrated that certain basic peptides (substance P, VIP, somatostatin, magainin-2, gastrin, melittin and Nal-arg-LHRH analog) are capable of inducing IgE independent release of histamine from rat mast cells. A similar analysis of AM and PAMP-20 has shown these peptides to be potent degranulators of rat mast cells with a respective $EC_{50}$ of 7.9±3.9 µM and 0.47±0.23 µM. AM was effective as magainin-2 in inducing histamine release, while PAMP-20 was twenty times more potent with bioactivity analogous to Nal-arg-LHRH. Immunohistochemical examination of rat skin and respiratory tract has identified AM expression in mast tissue cells. Furthermore, 2/4 mouse mast cell lines (MC/9, 10P2, 10P12, and 11PO-1) have been shown to express AM message when analyzed by RT-PCR. The collective data implicates AM/PAMP-20 as new vasodilators which could contribute to the fluid infiltrative process of allergic edema. In addition, these peptides have been shown to induce rat mast cell degranulation through an IgE independent mechanism and may define a previously unknown pathway of the normal immune response whereby adjacent mast cells are recruited in the absence of allergen.

Further, the monoclonal antibodies to AM of the present invention (see Example 4) are useful as therapeutics to block the allergic reaction induced by mast cell degranulation.

(12) Investigation of the Protective Action of AM/PAMP

It was previously demonstrated that AM is apically expressed in normal human bronchial epithelium and in resident pulmonary macrophages (Martinez, et al., *Endocrinology* 136:4099 (1995)) implicating a possible protective action similar to that of magainins and tracheal antimicrobial peptide (Diamond, et al., *Proc. Natl. Acad. Sci.* USA 90:4596 (1993); Diamond, et al., *Proc. Natl. Acad. Sci.* USA 88:3952 (1991); Schonwetter, et al., *Science* 267:1645 (1995); Zasloff, M., *Proc. Natl. Acad. Sci.* USA, 84:5449 (1987).

This possibility was further investigated by examining the expression of AM in a variety of epithelial surfaces, such as integument, respiratory, alimentary and genitourinary tracts, from different species including rats, mice, rabbits, guinea-pigs, hamsters, cats, dogs, pigs, and the toad *Xenopus laevis* using previously described methods of immunohistochemistry and in situ RT-PCR (Martinez, et al., Endocrinology 136: 4099 (1995)) (see also FIG. 21). Immunohistochemical studies demonstrate that AM is expressed in high levels within mammalian epithelial cells of the respiratory, alimentary, and urinary tracts, as well as within pulmonary alveolar macrophages. In the respiratory tracts of the species studied, all the ciliated and Clara cells were strongly positive for both the mRNA (FIG. 21A) and the peptide (FIG. 21B, 21C). In the case of the peptide, it was always accumulated in the apical region, suggesting an active secretion of AM to the pulmonary lumen.

Figure 21A:
FIGS. 21A-21I.
Figure 21B:
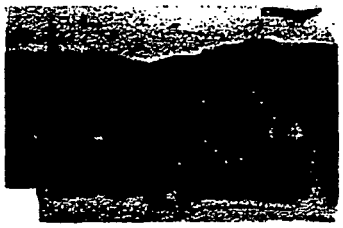
Figure 21C:
Figure 21D:
Figure 21E:
Figure 21F:
Figure 21G:
Figure 21H:

When the skin was subjected to immunocytochemical study, an intense staining was also observed. In the amphibian epidermis, most keratinocytes had a mild staining, but the strongest immunoreactivity to AM was located in the unicellular glands of the skin (FIG. 21D). The other glands, so characteristic of the amphibian integument, were devoid of staining. In mammals, the AM-like material was homogeneously distributed throughout the epidermis of both adults and the last stages of developing embryos (FIG. 21E).

The genitourinary tract was also found to be positive for AM. Most of the tubules in the kidney, such as the collector tubules, and the epithelium lining the ureter were immunoreactive, together with the fallopian tubes, the uterus (FIG. 21F) and the vagina, in all the species studied.

Figure 21I:

The digestive tube had previously been shown as one of the main sources for antimicrobial peptides (Schonwetter, et al., Science 267:1645 (1995)), and indeed AM was also expressed in this system. The immunoreactivity was mainly found in salivary glands (FIG. 21G), the epithelium of the hepatic bile ducts and the gallbladder, the Brunner's glands in the duodenum (FIG. 21H), the lumenal epithelium of the colon and some bottle shaped endocrine cells on the same organ (FIG. 21I).

Some other immunoreactive cell types included the ciliated cells lining the frog esophagus, the ductal system of the guinea-pig pancreas and the ependyma of the third ventricle in the rat brain.

The wide distribution of AM in epithelial cells, the apical cellular localization of AM along muco-cutaneous surfaces, and its localization to the Brunner's glands in the intestinal epithelium suggest a role in mucosal host defenses. Such a distribution is consistent with that of other antimicrobial peptides involved in antimicrobial protection (Zasloff, M., *Proc. Natl. Acad. Sci.* USA 84:5449 (1987)).

(13) Assessment of the Antimicrobial Activity of AM and its Gene-Related Peptides (PAMP) Against Bacterial and Fungal Pathogens.

In order to assess the antimicrobial activity of AM and its gene related peptides, both microdilution and macrodilution assays were performed against *Escherichia coli* (*E. coli*), *Staphylococcus aureus* (*S. aureus*), *Pseudomonas aeruginosa* (*P. aeruginosa*) and *Candida albicans* (*C. albicans*). A germination assay was also performed in order to further assess anti-candidal activity (Ghannoum, M. A. and Radwan, S. S., *Candida Adherence to Epithelial Cells*. CRC Press; Boca Raton, Fla. 1990 pp. 72-104).

Initial experiments using conventional techniques (National Committee for Clinical Laboratory Standards. Villanova, Pa. M7-A3, M27-P (1993)) for determination of minimum inhibitory concentrations (MICs) assessed by turbidity at 24 hours did not reveal significant differences in MCIs between AM or AM gene-related peptides and controls. In order to assess the presence of subtle antimicrobial activity of AM and gene-related peptides not detectable by routine turbidimetric tests, more sensitive quantitative methods were performed as modifications of bacterial and fungal timed kill assays that would evaluate growth inhibition over time (Walsh, et al., *Antimicrob. Chemother.* 17:75 (1986); Roilides, et al., *J. Infect. Dis.* 163:579 (1991); Roilides, et al., *J. Leukocyte Biol.* 57:651 (1995)).

AM and PAMP were found to have activity after 6 hours of incubation against *E. coli*, *P. aeruginosa*, and *C. albicans* but were ineffective against *S. aureus*. Several peptide fragments (Martinez, et al. *Endocrinology* 136:4099 (1995) representing the carboxy-terminal portion of AM (PO71 and PO72) and of PAMP (PO70) had little or no activity against these pathogens. However, preliminary findings suggest that the amino-terminal homologue of AM (AM1-12) exerted antimicrobial effects similar to those of intact AM in the microdilutional assay implicating that this fragment of AM could be responsible for the antimicrobial activity. AM and PAMP at 6 hours incubation showed higher growth inhibitory activity than albumin (negative control), PO70, PO71 and PO72 ($p=0.03$) and PAMP (0.0009). Am was five fold more active in the microdilution assay against *P. aeruginosa* than equimolar of human albumin controls ($p=0.0666$).

Figure 23A:
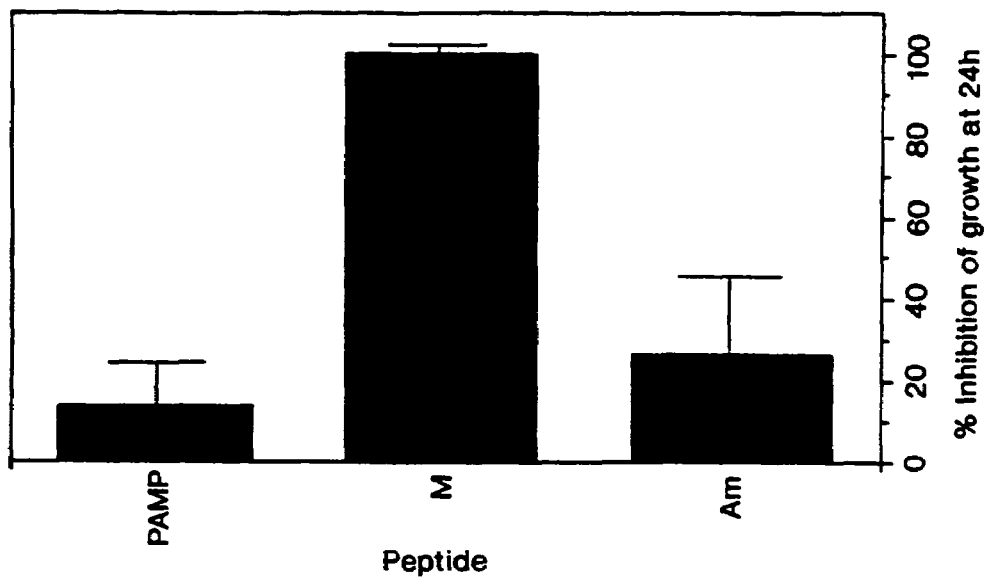
FIGS. 23A and 23B.
Figure 23B:
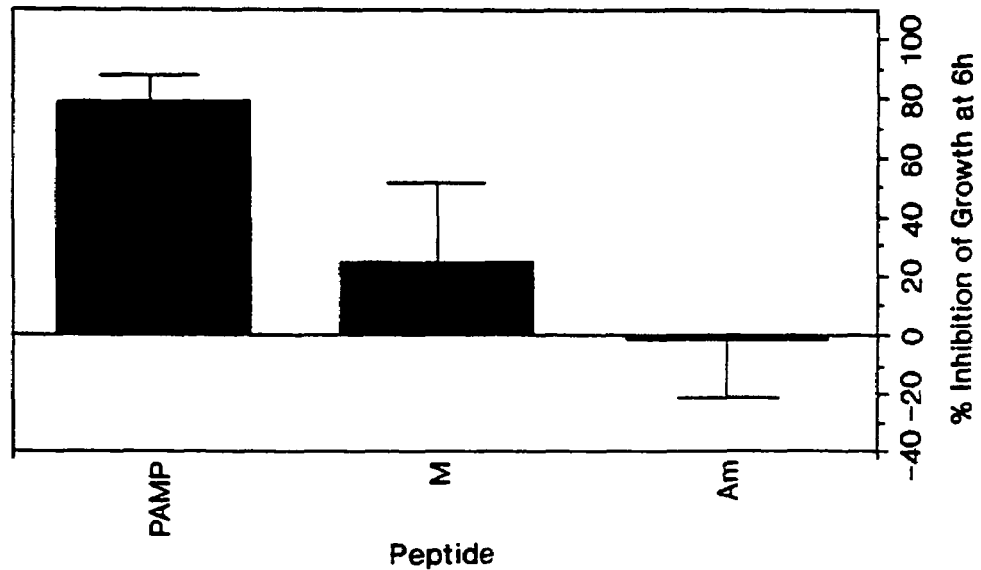

Antimicrobial activity was then evaluated in the macrodilution assay. There was initially no activity observed for AM at 6 hours, moderate activity for magainin, and even greater activity generated by PAMP (FIG. 23A). As of 24 hours incubation, however, the macrodilution pattern resembled that of the microdilutional assay with AM being somewhat more active than PAMP and magainin being significantly greater in antimicrobial activity than either AM or PAMP (FIG. 23B). Magainin was the only peptide that resulted in an optically clear suspension of bacteria. There was greater antimicrobial activity of AM and PAMP against *P. aeruginosa* at 24 hours exposure than at 6 hours incubation ($p=0.061$).

There was no apparent growth suppressive activity for AM, AM1-12, PAMP or the carboxypeptides against *S. aureus* in either microdilutional or macrodilutional assays. This may reflect a natural resistance which this pathogen has for the peptide which in turn could relate to surface charge repulsion phenomenology, proteolytic degradation of the peptide, or the lack of appropriate peptide/host interaction mediated by polysaccharide barrier of the bacterium.

(14) The Antimicrobial Effect of AM and Gene-Related Peptides (PAMP) Against *C. albicans*

The antimicrobial effect of AM and gene-related peptides was evaluated by macrodilutional and microdilutional assays against *C. albicans*, the common mucosal fungal pathogen of humans. The trends of antitrophic activity were less than those observed against *E. coli* and *P. aeruainosa*, particularly when compared with the albumin standard. However, there was a highly significant structure/function relationship found between the antimicrobial effect of AM (73%±8.1) or PAMP (79.7%±2.4) versus the carboxy-terminal portion of the peptide (46.8%±11.1, $p<=0.004$). While the overall activity of AM and PAMP was reduced in the macrodilutional assay, the relative patterns of antimicrobial activity were similar. Consistent with patterns observed for bacteria, magainin was more potent than AM and PAMP against *C. albicans*.

Germination is an important step in the pathogenesis of attachment and invasion of *C. albicans* to mucosal surfaces (Ghannoum, M. A. and Radwan, S. S., *Candida* Adherence to Epithelial Cells, CRC Press; Boca Raton, Fla., pp 72-104). The effects of AM and PAMP on germination of *C. albicans* were then studied as another indicator of antifungal activity. There was a significant inhibition of germination of *C. albicans* by increasing concentrations of AM at 4 hours incubation (FIG. 24) ($p=0.048$, ANOVA). There was a non-significant trend in the suppression of germination after 2 hours incubation.

The growth inhibitory properties of AM and PAMP were more active against the aerobic gram-negative bacteria, *E. coli* and *P. aeruginosa*, than against *C. albicans* and *S. aureus*. Such differential antimicrobial activity is also observed for the defensins and cecropins (Maloy, W. L. and Kari, U. P., *Biopolymers* (Peptide Science) 37:105 (1995); Lehrer, et al., *Cell*, 64:229 (1991)). For example, depending upon the amino acid sequences of cecropin peptides, which are found within porcine intestine, there are profound differences in antimicrobial activity against aerobic gram-negative bacilli (*E. coli* and *P. aeruginosa*) and gram-positive cocci (*Micrococcus luteus*). While there was minimum growth inhibitory activity of AM-related peptides against *C. albicans*, AM exerted a time-dependent inhibitory effect upon germination in cell culture media.

The concentrations at which these antimicrobial properties are achieved are generally 10 to 100 times greater than those of magainins and cecropins. However, if the tissue levels of these AM-related peptides are highly concentrated in the microenvironment, then the reported in vitro antimicrobial activity may also be active along epithelial cell surfaces. The antimicrobial effect was best observed at low inoculum concentrations, suggesting that organisms may degrade these AM-related peptides or that their cell targets may require a higher molar concentration for microbial effect. The antimicrobial mechanisms of the AM-related peptides remain to be further elucidated. Many of the antimicrobial peptides share in common highly basic properties and amphipathic activity with target cell membranes. Both AM and PAMP are highly charged moieties with isoelectric points of 9.7 and 11.1, respectively. Their amino acid structures contain extensive alpha/beta amphipathic regions which may simulate the membrane intercalation capabilities of magainin 1 and 2 (Oppenheim, et al., J. Biol. Chem., 263:7472 (1988)). FIG. 25 gives the amphipathic distribution and theoretical helical wheel symmetry of both peptides as calculated by DNASTAR software.

The antimicrobial properties of these AM-related peptides are dependent upon the assay used to measure their activity. For example, the activity of AM and PAMP appeared to be greater in the microdilutional assay than in the macrodilutional assay, suggesting that there may be interaction between the peptides and the glass or plastic surfaces. The kinetics of growth inhibition of those peptides, as well as other antimicrobial peptides, may differ substantially. As a case in point, the microbial activity of magainins became increasingly apparent at 24 hours by macrodilution, while adrenomedullin appeared to lose activity, possibly due to proteolytic cleavage. In a similar way, the class of salivary peptides known as histatins exert potent but transient activity lasting only for one to two hours before proteolysis inactivates activity (Oppenheim, et al., *J. Biol. Chem.*, 263:7472 (1988)).

Consistent with a potential role of AM in host defense are the recent observations of Shoji, et al., *Biochemical and Biophysical Research,* 215:531 (1995), demonstrating the highest level of increased expression of AM in lung, liver, and spleen in rats challenged intravenously with lipopolysaccharide. These findings suggest an upregulation of this antimicrobial peptide in the reticuloendothelial system that may mediate host response to bacterial and fungal pathogens. The diverse endocrinologic and hemodynamic properties of AM and its genetically related peptides leads to the suggestion that perhaps other antimicrobial peptides may have a wider range of non-antimicrobial physiological activities than heretofore appreciated.

Accordingly, the present invention provides for novel adrenomedullin peptides for use as antibacterial and antifungal agents. Specifically, AM peptides are useful for the treatment of vaginal yeast infections, athlete's foot, and thrush, a yeast infection which typically causes fatal pneumonia in cancer patients.

The AM peptides of the present invention may also be used to relieve discomfort and prevent bacterial and fungi infections of skin disorders. For example, the AM peptides may be applied topically to surgical incisions to prevent infections. Further, the AM peptides may be applied topically to chaffed skin, rashes, and skin lesions to prevent infection and promote healing.

(15) Adrenomedullin as a Regulator of Insulin Secretion

AM has been implicated in the regulation of insulin production. AM elevates cAMP in the target cells and regulates secretion of certain hormones. To determine if AM mediates any functional role in the rat endocrine pancreas a multiple analytical approach was utilized. Immunocytochemistry using a well characterized antibody showed that AM is present in the periphery of the islets of Langerhans. Double immunostaining and immunoelectron microscopy demonstrated that AM is stored in the D (delta), somatostatin-producing cells. In situ RT-PCR technology was used to confirm AM mRNA expression in the islets. Using isolated islets, it was shown that AM inhibits insulin secretion in a dose-dependent manner. In addition, the MoAb G6 (anti-AM) increased insulin secretion 6 fold by suppressing endogenous AM activity (see FIG. 18A). Elevating levels of cAMP, as shown by RIA, followed addition of AM. In conclusion, AM is expressed in the D-cells of the pancreas and reduces insulin secretion.

Because AM is secreted in insulin and urine, a diagnostic tool for the detection of levels of insulin in serum and urine as predictive of the disease state would be extremely useful. Accordingly, the novel AM peptides of the present invention are useful in the determination and diagnosis of various disease states. Specifically, the peptides and antibodies of the present invention are useful in the diagnosis, treatment, and prevention of type II diabetes.

(16) The Distribution of AM in the Pancreas

Pancreata from different species were examined by immunocytochemistry using a well-characterized polyclonal antibody (Martinez, et al., Endocrinology 136, 4099 (1995)). In humans, rats, and hamsters, the islets of Langerhans were immunoreactive for AM in all cells. However, specific cells in the periphery presented a stronger positivity than others (FIGS. 17A and 17B). In addition, a few strongly stained cells were found scattered through the pancreatic parenchyma or among the ductal epithelial cells. In the guinea pig, cat, and dog pancreata, the staining pattern was different: Most of the AM-like cells were scattered in the parenchyma and only occasional immunoreactive cells were found in the periphery of the islets. In these cases, no immunoreactivity was evident in the .beta.-cells (FIG. 17C). In addition, low intensity staining was consistently found in the ductal epithelia of the guinea pig pancreas (FIG. 17D). The presence of AM in the ductal pancreatic cells is consistent with the identification of AM in numerous epithelia, where the peptide is associated with notable antimicrobial activity (not shown).

To further characterize the nature of the cells containing the AM-like material, serial sections were stained with antibodies against AM and the major pancreatic hormones. Where weak immunoreactivity for AM was noted throughout the islet, colocalization with all the other hormones was evident, but the cells strongly positive for AM colocalized only with pancreatic polypeptide (FIGS. 17E and 17F). This result differs from a previous report (H. Washimine et al., Histochemistry 103, 251 (1995)), which suggested a colocalization with somatostatin based on the peripheral distribution of AM immunoreactivity. Double immunogold staining at the electron microscopic level confirmed the colocalization of AM with pancreatic polypeptide in peripheral cells of rat pancreas (FIG. 17G). Consistent with the light immunohistochemical data, few immunogold particles detecting AM were found in other endocrine cell types by electron microscopy (FIG. 17H).

AM has some structural similarities to calcitonin gene-related peptide (CGRP) and amylin (K. Kitamura, K. Kangawa, H. Matsuo, T. Eto, *Drugs* 49, 485 (1995)), both of which are involved in pancreatic physiology. Nevertheless, the distribution of these three peptides in the pancreas varies: Amylin is mainly located in the β-cells, colocalizing with insulin (Mulder, et al., *Cell Tissue Res.* 274, 467 (1993)), and CGRP is present in pancreatic nerves as well as in peripheral cells of the islets (B. Ahren and F. Sundler, *Cell Tissue Res.* 269, 315 (1992)). The differential distribution of the immunoreactivities, together with the absorption controls, excludes a possible cross-reactivity of the AM antibody with amylin or CGRP.

(17) Physiological Effects of AM In Endocrine Pancreas Regulation

To identify the potential biological role of AM in the secretion of pancreatic hormones, three experimental models were used: isolated islets of Langerhans from rat, β-cell lines in culture, and oral glucose tolerance tests in rats.

Figure 18B:
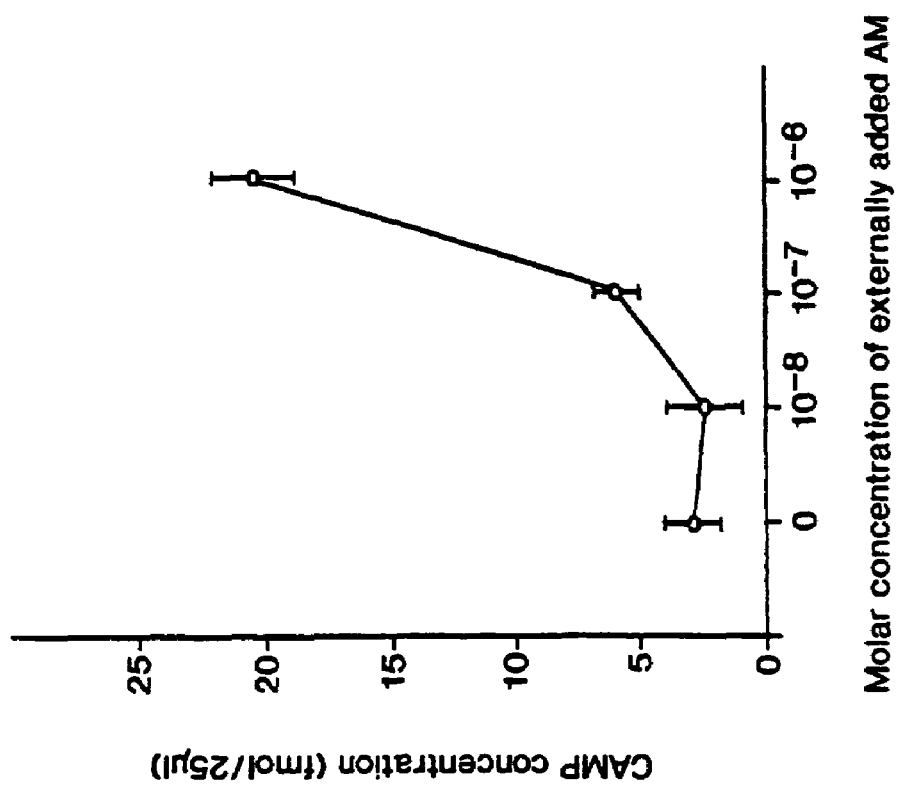
FIGS. 18A and 18B: Effects of AM and MoAb-G6 (α-AM) on the release of insulin from rat isolated islets.
Figure 18A:
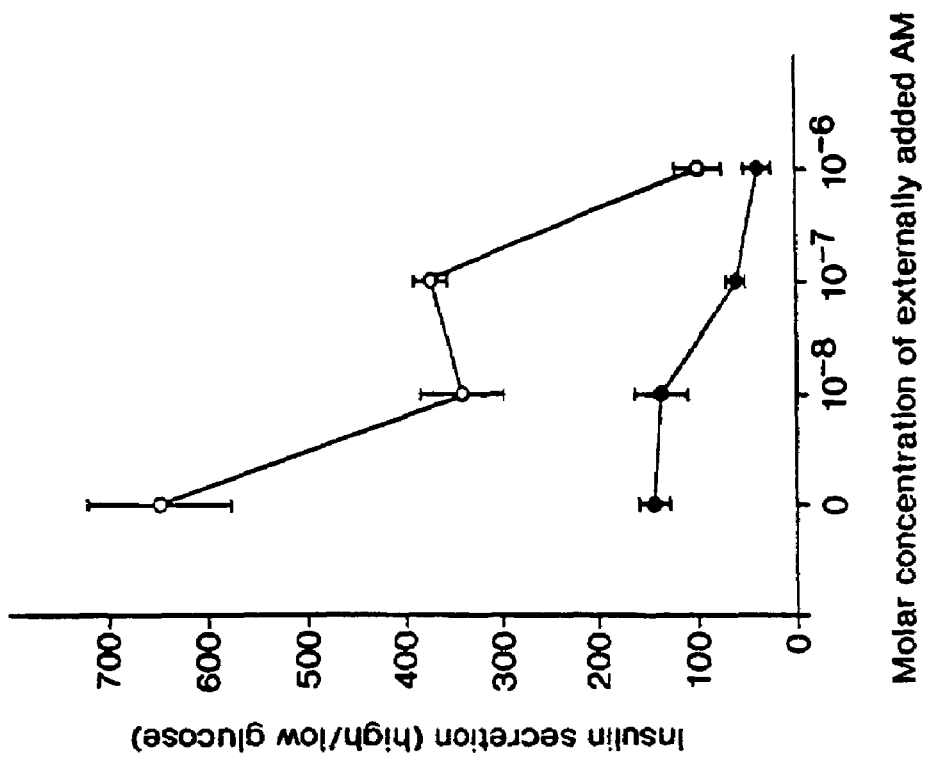

The addition of AM to freshly isolated islets resulted in a dose-dependent reduction of insulin secretion (FIG. 18A). This inhibition reaches 78% for an AM concentration of 1 μM. Using MoAb-G6, a monoclonal antibody that neutralizes AM (not shown), a fivefold increase of insulin secretion was observed in the absence of extrinsic AM (FIG. 18A). Evidently, this striking effect was caused by neutralization of endogenous AM produced by the islets. The addition of extrinsic AM again resulted in a dose-dependent competitive inhibition (FIG. 18A). Consistent with this observation, cAMP levels increased in the islets when AM was added (FIG. 18B).

To investigate AM's effect on β-cells, the influence of AM in six well-characterized, insulin-producing cell lines was studied: RINm, N289, TR4, CRL 2057, CRL 1777, CRL 2055 (American Type Culture Collection, Rockyille, Md.). Although these cell lines expressed AM mRNA, as shown by reverse transcription-polymerase chain reaction (RT-PCR) (FIG. 19), no change in insulin secretion rate was observed after administration of either AM or the monoclonal antibody (results not shown). These results suggest that β-cells, at least in culture, do not express AM receptors and apparently more complex interactions occur in the islets. To confirm this hypothesis, binding of $^{125}$I-AM (0.2 nM per 5×10$^5$ cells) was investigated in RINm cells and in NCI-H1264, a lung adenocarcinoma used as a positive control. No binding (25 cpm) was observed in the RINm cells, but strong radioactivity (2265 cpm) was found in NCI-H1264. Possibly AM modulates a different cell type that, in turn, inhibits insulin secretion through endocrine or paracrine pathways. A similar mechanism has been described for amylin (R. A. Pittner et al., J. Cell. Biochem. 55S, 19 (1994)). Nevertheless, the existence of AM receptors in β-cells in vivo cannot be ruled out, although it has been shown that receptor systems that act in the β-cell through an increase in cAMP and Ca$^{2+}$ induce rather than inhibit secretion of insulin (Holz, et al., J. Biol. Chem. 270, 17749 (1995)). On the other hand, the possibility that AM acts through other receptors cannot be excluded. There is evidence that AM binds to CGRP receptors with lower affinity (Eguchi, et al., Endocrinology 135, 2454 (1994); Hall, et al., Brit. J. Pharmacol. 114, 592 (1995); Zimmermann, et al., Peptides 16, 421 (1995)) and could bind the amylin receptors similarly, since the three peptides are structurally related (K. Kitamura, et al., Drugs 49, 485 (1995)).

In a third experiment, the influence of AM in oral glucose tolerance testing of nonanesthetized rats was measured (protocol No. 95-062, NCI). AM dramatically (p=0.003) blocks insulin secretion for at least 20 mm after intravenous injection, so the levels of circulating glucose were significantly higher (p=0.006) than in the control animals (FIG. 20A).

The collective data of the present invention implicates AM as a new diabetogenic peptide capable of modulating insulin secretion and blood glucose metabolism. Although the exact mechanism remains to be elucidated, isolated islet studies and analysis of cultured β-cell lines indicate that an unidentified secondary mediator is involved. It should be noted that insulin-producing cell lines express AM message and are faintly immunoreactive for the peptide, but their ability to secrete insulin is not directly affected by either exogenous AM or MoAb-G6. Thus AM regulation of insulin secretion in isolated islet experiments and rat physiology involves more complex interactions than initially surmised. Since the expression of AM (at least in cardiovascular systems, is affected by levels of tumor necrosis factor-α, interleukin-1, lipopolysaccharide, interferon-γ, endothelin-1, angiotensin II, substance P, bradykinin, thrombin, and vasoactive intestinal peptide (S. Sugo, et al., *FEBS Lett.* 369, 311 (1995)), any combination of these bioactive substances may be involved with AM in regulating insulin secretion. In fact, some reports link different forms of diabetes with these substances (G. S. Hotamisligil and B. M. Spiegelman, *Diabetes* 43, 1271 (1994); T. H. Jones, *Clin. Endocrinol.* 40, 703 (1994)).

It has also been observed that AM's physiological effects are somehow connected with those produced by nitric oxide (C. J. Feng, et al., *Life Sci.* 55, 433 (1994)). This relationship may be due to the cross talk in the target cell between the signal transduction pathways for AM, which increases cAMP, and nitric oxide, which increases cGMP (Fiscus, et al., *Neuropeptides* 26, 133 (1994)). Since nitric oxide synthase is present in the islets of Langerhans and nitric oxide regulates insulin secretion (Schmidt, et al., *Science* 255, 721 (1992); Worl, et al., *Histochemistry* 102, 353 (1994)), it would be interesting to investigate the interactions between these two regulatory systems.

The well-known vasodilatory effect of AM may also influence the insulin secretion rate by increasing pancreatic perfusion. Although this cannot be the main mechanism, as demonstrated in the islet experiments where blood flux is irrelevant, it merits further evaluation.

A better understanding of AM interactions in normal pancreatic physiology and in different pathological states, such as diabetes and obesity, may help define new areas of therapeutic intervention to obviate these metabolic disorders.

(18) The Role of cAMP as a Growth Regulator

The role of cAMP as a growth regulator has been previously established in a variety of human tumor cell lines (T. W. Moody, et al., *Proc. Natl. Acad. Sci* U.S.A. 90, 4345 (1993); Cho-Chung, et al., *Life Sci.* 48, 1123 (1991); Ishizuka, et al., *Cancer Res.* 54, 2129 (1994); Hoosein, et al., *Regul. Pent.* 24, 15 (1989); Yu, et al., *Endocrinology* 131, 1188 (1992)). This secondary signal transducer has been reported to have a biphasic effect on tumor proliferation whereby in certain instances it can mediate growth promotion while in others it functions as a growth inhibitor (Cho-Chung, et al., *Life Sci.* 48, 1123 (1991); Ishizuka, et al., *Cancer Res.* 54, 2129 (1994); Yu, et al., *Endocrinology* 131, 1188 (1992)). This dual function has been shown to depend on the relative amounts of two distinct cAMP-dependent protein kinase isoforms, RI and RII (Ishizuka, et al., *Cancer Res.* 54, 2129 (1994)). RI/RII isoforms are inversely expressed during embryogenesis, cell differentiation, and malignant transformation (S. M. Lohmann and U. Walter, in *Advances in Cyclin Nucleotide and Protein Phosphorylation Research*, P. Greengard, et al., Eds. (Raven Press, New York, 1984), vol. 18, pp. 63-117). Elevation of the RI isoform correlates with cell growth and transformation, while increases in the RII type correlate with growth inhibition and differentiation ((S. M. Lohmann and U. Walter, in *Advances in Cyclin Nucleotide and Protein Phosphorylation Research*, P. Greengard, et al., Eds. (Raven Press, New York, 1984), vol. 18, pp. 63-117)). Thus, depending on the relative amounts of these isoforms, cAMP induces either growth-promotion or growth-suppression effects.

Several reagents that regulate the expression of AM have been identified. These include enhancing factors such as interleukin-1α/β (IL-1α/β), tumor necrosis factor-α/-β (TNF-α/-β), lipopolysaccharide (LPS), certain adrenocortical steroids, angiotensin II, endothelin-1, bradykinin, substance P, and adrenaline and suppressor factors such as forskolin, 8-bromo-cAMP, thrombin, vasoactive intestinal polypeptide, and interferon-γ (S. Sugo, et al., *Biochem. Biophys. Res. Commun.* 203, 719 (1994); Sugo, S., et al., *Biochem. Biophys. Res. Commun.* 207, 25 (1995); N. Minamino, et al., *Biochem. Biophys. Res. Commun.* 211, 686 (1995); S. Sugo, et al., *FEBS Lett.* 369, 311 (1995)). Many of these factors help activate the immune system during an inflammatory response. A recent review on the causes and prevention of cancer made two interesting points: i) Increased cell division gives rise to increased risk of cancer, which can be driven by increased levels of particular hormones, and ii) Chronic infection or inflammation contribute to one-third of the world's cancers (Ames, et al., *Proc. Natl. Acad. Sci.* U.S.A. 92, 5258 (1995)). Given that IL-1α/β, TNF-α/-β, and LPS are agents of immune inflammation that are known to increase the expression of AM and that AM can mediate trophic effects on tumor cell lines, these findings indirectly implicate AM as a potential risk factor for malignant conversion. Since most of the tumor cell lines examined expressed this peptide, it may represent a generic target for intervention strategies to disrupt neoplastic transformation.

The present invention demonstrates that AM is expressed in most of the human tumor cell lines tested and that it can function as an autocrine growth factor capable of driving a self-perpetuating state in malignant disorders. Responding tumor cell lines were shown to express AM receptors and showed peptide-mediated increases in intracellular cAMP.

These findings, together with reports that AM is found in tumor tissue from pathological specimens (Martínez, et al., *Endocrinology* 136, 4099 (1995); Martínez, et al., *J. Histochem. Cytochem.* 43, 739 (1995)), point towards the need for additional investigative studies to determine the precise role of AM in carcinogenesis.

Additionally, given the similar amino acid sequence of AM between species and its implicated action on cell growth, the present invention provides for methods of evaluating the relationships of this peptide with other sites of rapid cellular proliferation (e.g., embryogenesis, wound repair, and gastrointestinal turnover) and the way these relationships track down evolutionary lines.

EXAMPLES

The examples herein are meant to exemplify the various aspects of carrying out the invention and are not intended to limit the invention in any way.

Example 1

Cell Culture

Ten normal lung specimens from patients who died without pulmonary involvement were provided by the Department of Pharmacology, University of Pittsburgh (protocol ML1259). Twenty additional formalin-fixed paraffin-embedded blocks containing representative cases of lung tumors (Table 1) were obtained from the files of the NCI-Navy Medical Oncology Branch, National Medical Center (Bethesda, Md.; protocol 83-15). Five lung tumor cell lines were used in this study: NCI-H146, H345 (small cell lung carcinomas), H676 (adenocarcinoma), H720 (carcinoid), and H820 (bronchioalveolar carcinoma). Cells were grown in serum-free hormone-free medium, as previously described (Siegfried, et al., *J Biol Chem* 269:8596-8603 (1994)). Pellets of approximately $5 \times 10^6$ cells were fixed in 4% paraformaldehyde, washed in PBS, resuspended in 1 ml 2% low melting point agarose (NuSieve, FMC BioProducts, Rockland, Me.), allowed to solidify, and embedded in paraffin after routine histopathology techniques. mRNA was extracted from fresh cell pellets using the isothiocyanate-cesium chloride method of Glisin, et al. (Glisin, et al., *Biochemistry* 13:2633-2637 (1974)). Polyadenylated RNA from normal human lung and adrenals were purchased from Clontech Laboratories (Palo Alto, Calif.).

TABLE 1

Comparison between the results obtained using immunocytochemistry and in situ RT-PCR in surgical specimens representing the different major neoplasias of the lung

| Tumor type | Immunocytochemistry | In situ PT-PCR |
| --- | --- | --- |
| SCLC | 0/5 | 2/5 |
| Carcinoids | 1/2 | 1/2 |
| Large cell carcinomas | 2/4 | 3/4 |
| Adenocarcinomas | 3/4 | 3/4 |
| Squamous carcinomas | 4/5 | 3/5 |
| Total | 10/20 | 12/20 |

SCLC, Small cell lung carcinomas. The numerator represents the number of positive cases, and the denominator indicates the total number of studied cases.

Example 2

Standard Reverse Transcriptase (RT)-Polymerase Chain Reaction (PCR)

Three oligonucleotides (Table 2) were made in a MilliGen/Biosearch 8700 DNA synthesizer (Millipore, Marlborough, Mass.) and used as primers and probes for PCR and Southern blot experiments, with an expected PCR product of 410 base pairs (bp). The primers were designed to bridge the third intron of the AM gene (see FIG. 1) to distinguish possible genomic amplification by the presence of a longer product (644 bp).

Reverse transcription was performed using the Superscript Preamplification System (GIBCO-BRL, Gaithersburg, Md.). A Perkin-Elmer 9600 Thermocycler (Perkin-Elmer, Norwalk, Conn.) was used to amplify the samples. All buffers, enzymes, and nucleotides used were obtained from Applied Biosystems (Perkin-Elmer/Cetus). PCR products were analyzed electrophoretically using 1% agarose gels, and the ethidium bromide staining was observed under UV light, followed by Southern analysis.

TABLE 2

Sequences of the peptides and oligonucleotides synthesized:

| | |
| --- | --- |
| PO70 (YY-PreproAM$_{34-41}$) | Y-Y-W-N-K-W-A-L-S-R-NH$_2$ (SEQ. ID. NO: 1) |
| PO71 (YGG-PreproAM$_{122-131}$) | Y-G-G-H-Q-I-Y-Q-F-T-D-K-D-NH$_2$ (SEQ. ID. NO: 2) |
| PO72 (PreproAM$_{116-146}$) | T-V-Q-K-L-A-H-Q-I-Y-Q-F-T-D-K-D-K-D-N-V-A-P-R-S-K-I-S-P-Q-G-Y-NH$_2$ (SEQ. ID. NO: 3) |
| Sense primer (AM 94-114) | 5'-AAG-AAG-TGG-AAT-AAG-TGG GCT-3' (SEQ. ID. NO: 4) |
| Antisense primer) (AM 444-464) | 5'-TGG-CTT-AGA-AGA-CAC-CAG-AGT-3' (SEQ. ID. NO: 5) |
| Antisense probe (AM 289-309) | 5'-CTG-GAA-GTT-GTT-CAT-GCT-CTG-3' (SEQ. ID. NO: 6) |
| Proadrenomedullin N-terminal 20 peptide (PAMP-20) | A-R-L-D-V-A-S-E-F-R-K-K-W-N-K-W-A-L-S-R-NH$_2$ (SEQ. ID. NO: 7) |

Example 3

Southern Blot Analysis

Gels were denatured in 1.5M NaCl-0.6M NaOH and 1.5M NaCl-2M Tris and blotted onto a 0.2-µm nitrocellulose filter in 20×SSC by capillary flow transfer overnight. The filter was cross-linked at 80° C. under vacuum and incubated in hybridization buffer. The antisensenested probe was $^{32}$P end labeled using standard procedures. Hybridization with the probe was performed overnight at 42° C. Room temperature stringency washing was performed in 5×SSC-0.1% sodium dodecyl sulfate and 1×SSC-0.1 sodium dodecyl sulfate. Filters were air dried and autoradiographed on Kodak XAR5 film (Eastman Kodak, Rochester, N.Y.).

Example 4

Antibody Production and Characterization

Three fragments of the AM prohormone (see Table 2 and FIG. 1) were synthesized in a MilliGen/Biosearch 9050 peptide synthesizer using FMOC chemistry, purified by preparative high performance liquid chromatography (HPLC) RP-$C_{18}$ on a Beckman System Gold (Beckman Instruments, Fullerton, Calif.), and the molecular weight of the peptide, designated PO72, was confirmed by mass spectrometry (Perkin-Elmer Sciex API III Plus, Foster Cit, Calif.). Peptide PO72 was coupled to keyhole limpet hemocyanin (Calbiochem-Behring, La Jolla, Calif.) via glutaraldehyde cross-linkage, and the conjugate was used to hyperimmunize New Zealand White rabbits, as previously described (Cuttitta, et al., *J Clin Endocrinol Metab* 67:576-583 (1988)). Resulting antisera were characterized for binding specificity and respective titers using a solid phase (radioimmune assay) RIA with [$^{125}$I] protein A as the detector (Cuttitta, et al., *J Clin Endocrinol Metab* 67:576-583 (1988)). In brief, test peptides were passively absorbed to individual wells (50 ng/well; overnight at 4° C.) of a 96-well polyvinylchloride microtiter plate (Dynatech Laboratories, Chantily, Va.), after which the plate was coated with 1% bovine serum albumin (BSA) in phosphate buffered saline (PBS) to minimize nonspecific bonding. Test peptides included PO70, PO71, and PO72 (in-house synthesis), AM, gastrin, cholecystokinin, gastrin-releasing peptide, glucagon-like peptide 1,8-arginine vasopressin, vasoactive intestinal peptide, oxytocin, GRF, calcitonin, CGRP, neuropeptide Y (NPY), αMSH (Peninsula Laboratories, Belmont, Calif.), and BSA (Sigma Chemical Co., St. Louis, Mo.) as a negative control. The titration screen covered a range from 1:100 to 1:204,800 (2-fold dilutions). The antiserum with the highest titer for AM and minimal cross-reactivity to related peptides was selected for all immunohistochemical studies.

Example 5

Western Blotting

Whole cell lysates of tumor cell line NCI-H720 were generated following a protocol slightly modified from the previously reported (Cuttitta, et al., *J Clin Endocrinol Metab* 67:576-583 (1988)). In summary, cells were harvested 48 hours after their last feeding, washed three times in PBS, and pelleted by centrifugation (2000 rpm for 10 min at 4° C.). The pellet (~5×10$^7$ cells) was resuspended in 1 ml PBS containing a 1-mM final concentration of each of the following protease inhibitors: Pefabloc (Centerchem, Stanford, Conn.), and bestatin and phosphoramidon (Sigma). The cell suspension was then homogenized, sonicated, and clarified by ultracentrifugation, and the final protein concentration was determined (Bio-Rad Laboratories, Richmond, Calif.).

Cell lysates were electrophoretically fractionated on a 10-20% Tricine gel (Novex, San Diego, Calif.) at 100 V for 2 hours under nonreducing conditions. Two nanograms of peptide PO72 and AM were added to separate wells as positive control standards. Transfer blotting was accomplished in the same apparatus equipped with a titanium plate electrode insert, and proteins were affixed to a polyvinyldifluoride membrane (Immobilon PVDF, Millipore) at 30 V for 2 hours. The membrane was blocked overnight in 1% BSA-PBS, incubated for 1 hr in a 1:1000 dilution of rabbit anti-PO72 (bleed 2343), washed three time in PBS, exposed to 1×10$^6$ cpm [$^{125}$I] protein A for 1 hour at 28° C., washed six times in PBS, dried, and autoradiographed overnight at −80° C. on Kodak XAR5 film. The specificity control consisted of a duplicate membrane incubated in antigen-preabsorbed (10 nmol/ml PO72) antiserum.

Example 6

Immunocytochemisty

The avidin-biotin histochemical staining procedure (Hsu, et al., *J Histochem Cytochem* 29:577-580 (1981)) was used to localize AM in normal lung, cell lines and tumors. All reagents were obtained from the Vectastain ABC kit (Vector Laboratories, Burlingame, Calif.). Titration of the antibody in paraffin sections showed that a concentration of 1:1000 was appropriate for immunocytochemical analysis. Rat adrenals were used as positive controls. Negative controls included (1) substitution of the primary antibody by a prebleed serum and (2) preabsorption of the antibody with 10 nmol/ml of the synthetic peptide PO72. As the antibody showed a slight cross-reactivity with NPY (see FIG. 2), preabsorptions with this peptide were also performed.

Example 7

In Situ RT-PCR

To localize the expression sites for AM, a direct method for in situ amplification of mRNA (Martínez, et al., *J Histochem Cytochem,* 43:739 (1995)) in a Hybaid OmniSlide System thermocycler (National Labnet Co., Woodbridge, N.J.) was used. After dewaxing, the sections were subjected to permeabilization with 10 μg/ml proteinase K (Sigma) for 15 min at 37° C. RT was performed during the SuperScript Preamplification system (GIBCO-BRL) before the PCR reaction. The Taq polymerase was blocked with a specific monoclonal antibody (TagStart, Clontech) before being added to the PCR mixture to obtain a synchronous "hot start" for all slides. The PCR mixture contained 2.5 mM MgCl$_2$, 200 μM deoxy-NTPs, 100 μM digoxigenin-deoxy-UTP (Boehringer Mannheim, Indianapolis, Ind.), 1 ng/μl primers, 50 mM KCl, and 10 mM Tris-HCl, pH 8.3. Twenty cycles with an annealing temperature of 55° C. were performed, and the PCR products were located using the Digoxigenin Detection Kit (Boehringer Mannheim) following the manufacturer's instructions. Controls included (1) omission of reverse transcriptase, and (2) substitution of the primers by water in the PCR mixture.

Example 8

Antibody Characterization

Antiserum from bleed 2343 was determined to have the highest titer to AM, with a resulting EC$_{50}$ of 1:1×10$^4$, showing less than 1.0% (calculated 0.77%) cross-reactivity with NPY at this dilution and less than 0.1% binding with other test peptides (FIG. 2). Binding differences between peptide PO72 (original immunogen) and AM presumably reflect stearic interference generated during passive absorption to polyvinylchloride matrix. The larger AM peptide, which contains the PO72 antigen as an internal fragment, had a selective advantage of epitope availability when absorbed to the plastic support. Alternatively, binding differences between these two peptide targets could reflect variation in adherence during passive absorption to the plate.

Example 9

Western Blot

Figure 3:
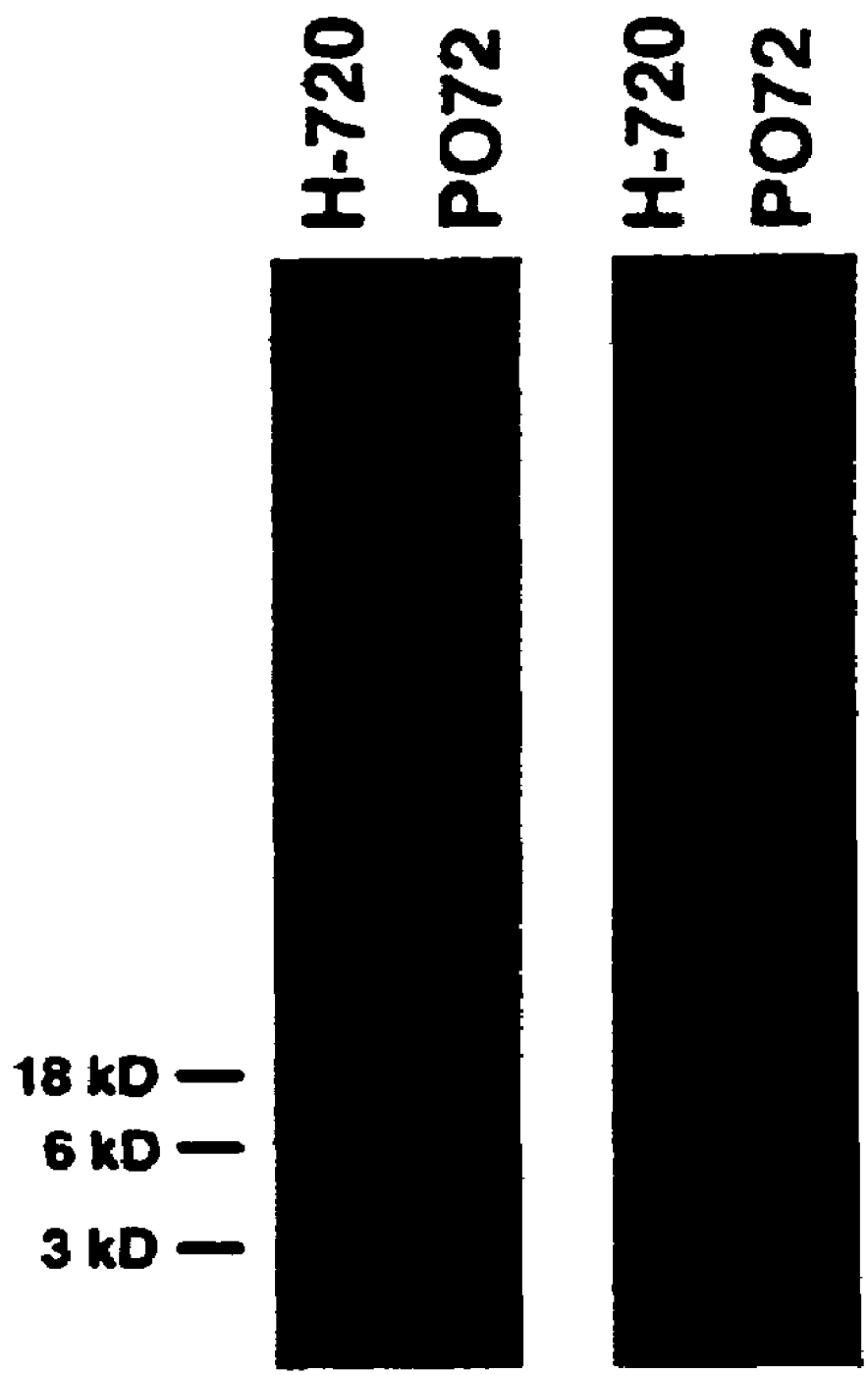
FIG. 3: Detection of AM-like immunoreactive species in the whole cell lysate of a human lung carcinoid cell line, NCI-H720. The right lane contains 2 ng synthetic PO72 (molecular weight, 3576). The specificity of detection is demonstrated by antigen absorption of anti-PO72 antiserum (right panel).
Figure 5A:
FIGS. 5A, 5B, 5C, and 5D.
Figure 5B:

Electrophoretic fractionation of NCI-H720 cell lysate proteins revealed two immunoreactive AM-like species with molecular weight of approximately 18,000 and 6,000 (FIG. 3). Presumably, these bands represent the AM precursor (185 amino acids) and the authentic peptide (52 amino acids). Immunostaining of these bands and the positive control was eliminated after antigen preabsorption of the antiserum, demonstrating specificity of detection.

Example 10

Normal Lung

Figure 4A:
FIGS. 4A, 4B, 4C, and 4D.
Figure 4B:
Figure 4C:
Figure 5C:
Figure 4D:
Figure 5D:
Figure 6A:
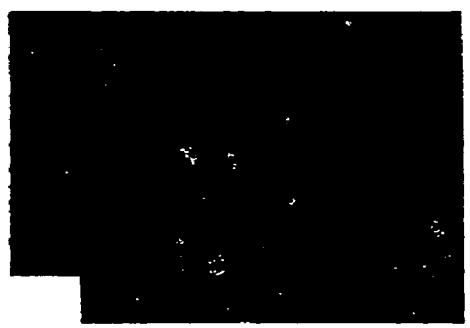
FIGS. 6A and 6B.
Figure 6B:
Figure 7A:
FIGS. 7A and 7B.
Figure 7B:
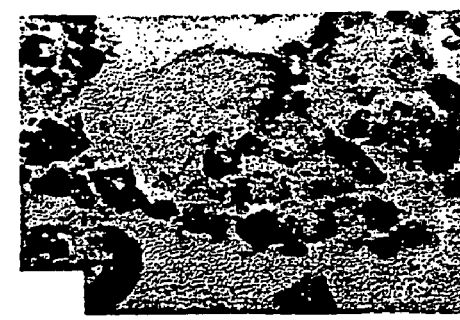

In the normal human lung, immunoreactivity of AM was found in the columnar cells of bronchi and bronchioli (FIGS. 4A-4D), in some of the serous cells of the bronchial glands, in the perikaryon of parasympathetic neurons (FIGS. 5A-5D), in the endothelium of blood vessels (FIG. 5C), in select chondrocytes (FIGS. 6A and 6B), in alveolar macrophages (FIG. 7A), and in smooth muscle cells. When the chondrocytes were stained, only the more mature cells in the center of the cartilage plates showed immunoreactivity, whereas the chondroblastic cells in the periphery were negative. The in situ RT-PCR approach showed that all cells demonstrating AM immunoreactivity also express the mRNA for AM (FIGS. 4C, 5C, and 7A). Negative controls for both immunocytochemistry and in situ RT-PCR demonstrated staining specificity (FIGS. 4B, 4D, 5B, 5D, 6B, and 7B). Preabsorption with NPY did not affect staining (data not shown).

Example 11

Expression of AM in Tumor Cells

Figure 8A:
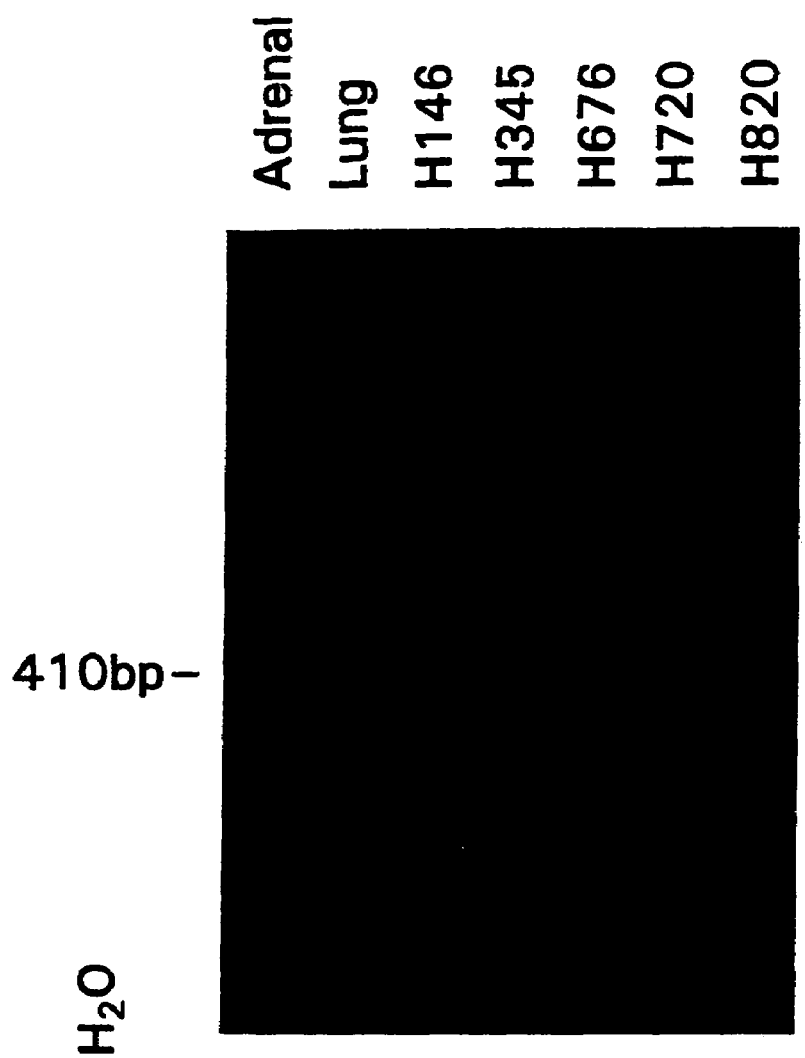
FIG. 8: Characterization of AM by RT-PCR in mRNA from normal tissues and pulmonary tumor cell lines. The PCR products had the proper size following electrophoretic fractionation (410 bp) when visualized with UV light (FIG. 8B), and they hybridized with the specific probe after Southern blot (FIG. 8A). H146 and H345 are small cell carcinomas, H676 is an adenocarcinoma, H720 is a carcinoid, and H820 is a bronchioalveolar carcinoma. H146 was the only cell line that tested negative for AM.
Figure 8B:
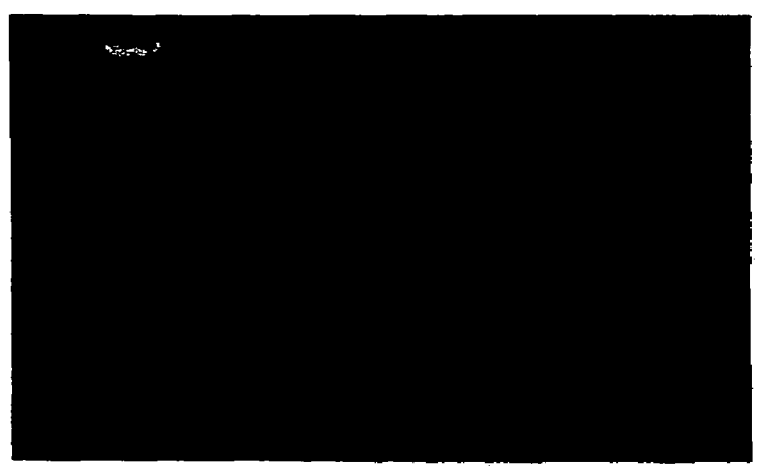
Figure 10A:
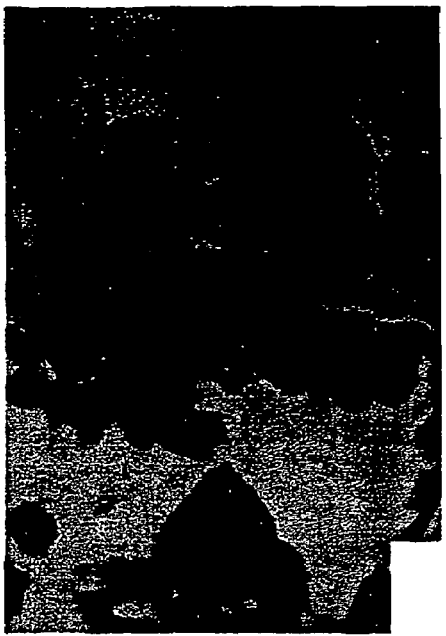
FIGS. 10A and 10B.
Figure 10B:
Figure 9A:
FIGS. 9A and 9B.
Figure 9B:
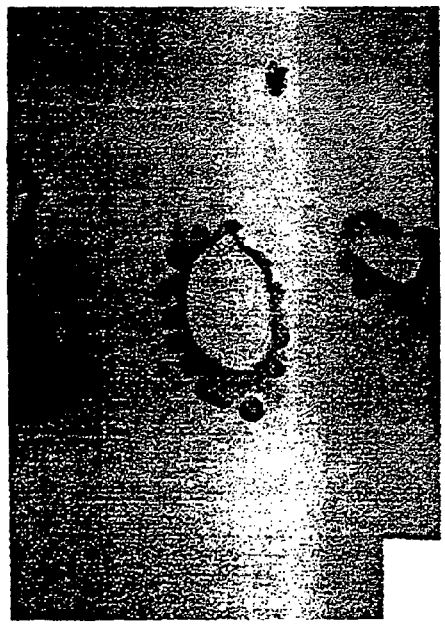

To determine whether tumor cells of pulmonary origin express AM, five cell lines were analyzed by RT-PCR (FIG. 8); four of them (one small and three non-small lung carcinomas) produced AM mRNA, whereas H-146, a small cell lung carcinoma, was negative. Immunocytochemical and in situ RT-PCR methods also detected AM in these cell lines following the same pattern (FIGS. 9A and 9B). To examine the production of AM by tumors in vivo and to ensure that the expression of AM was not an artifact of the culture procedure, 20 paraffin blocks of pulmonary malignancies with different diagnoses were analyzed (Table 3). All small cell lung carcinomas were negative by immunocytochemistry, whereas 10 of 15 of the non-small lung carcinomas were positive. The in situ RT-PCR technique revealed that 2 of 5 of the small cell carcinomas expressed AM mRNA (FIGS. 10A and 10B), suggesting that the amount of AM peptide in these tumors was below the immunocytochemical detection limit.

Example 12

Expression of AM mRNA in Normal Human Tissue and Tumor Cell Lines a. Cell Lines and Normal Tissue: Table 3 sets forth a summary of all tumor cell lines evaluated for AM mRNA by RTPCR analysis showing widespread expression (95%). The tumor cell lines evaluated were as follows: Small Cell Lung Carcinoma (SCLC): H60, H69c, H82, H146, H187, H209, H345, H446, N417, H510, N592, H735, H774, H889, H1092, and Non-small Lung Cell Carcinomas (NSCLC): H23, H157, H460, H676, H720, H727, H820, H1264, H1385, H1404, H2087, H2228, A549, UMCll. Breast: SK-BR-3, ZR75-1, MCF-7, BT-20, MDA-MD231, BT-474, H2380. Colon: H630, SNUC-1. Nervous system: T98G (glioblastoma), C6 (glioma), and TC106, CHP100, TC17, PNET, Peii, SYSY, AS, LAN-1, KCNR-C, KCNR-DRA (neuroblastomas of the peripheral nervous system). Ovarian: NIH:OVCAR-3, SKOV3, OVT2, A2780, CP70. Prostate: DU-145. Adrenal: H295. Chondrosarcoma: SW578. Chronic monocytic leukemia: U937. All lung, adrenal, colon, and H2380 tumor cell lines were obtained from the NCI-Navy Medical Oncology Branch. Brain tumors were from the NCI, Pediatric Branch. The remaining cell lines came from ATCC, Rockville, Md. RNA extraction, cDNA amplification and RTPCR were performed as previously described (T. A. Murphy and W. K. Samson, *Endocrinology* 136, 2459 (1995)). Cells were maintained under serum-free/hormone-free conditions in RPMI 1640 without phenol red (Life Technologies, Gaithersburg, Md.) containing $3 \times 10^{-8}$ M sodium selenite ($R_O$) at 37° C. in 5% $CO_2$. (Siegfried, et al., *J. Biol. Chem.* 269:8596-8603 (1994)).

b. Antibodies: A previously characterized polyclonal antibody against PO72($H_2$N-TVQKLAHQIYQFTDKDKDN-VAPRSKISPQGY-CONH$_2$), a fragment of AM (Martinez, A., et al., *Endocrinology* 136:4099-4105 (1995)), was used for Western blot analysis.

A monoclonal antibody, designated as MoAb-G6, was developed against the PO72 peptide of AM following a modified procedure to previously published methodology (Cuttitta, F., et al., *Nature* 316:823-826 (1985)). Balb/c mice were hyperimmunized with PO72 peptide conjugated to keyhole limpet hemocyanin via glutaraldehyde cross-linkage (1 mg/1 mg coupling ratio). Splenic lymphocytes were fused to mouse myeloma cell line RNS1 following standard protocols. Resulting hybrids were screened for anti-PO72 MoAb production using a solid phase ELISA technique. Responding hybridomas were subcloned twice, expanded in mass culture, and utilized as the seed stock for ascites generation. MoAb-G6 (IgAκ isotype) represented the highest titer antibody and was purified from ascites fluid by affinity chromatography on a solid phase PO72 coupled resin (BioRad Affi-Prep 10, Richmond, Calif., coupling efficiency 10 mmoles peptide/ml resin). The antibody was characterized for binding specificity using a solid phase RIA with $^{125}$I-Protein A as the detector (Cuttitta, F., *J. Clin. Endocrinol. Metab.* 67:576-583 (1988) (see FIG. 13). In brief, test peptides were passively absorbed onto individual wells (50 ng/well; overnight at 4° C.) of a 96-well polyvinylchloride microtiter plate (Dynatech Labs., Chantilly, Va.) after which the plate was coated with 1% BSA in PBS to minimize nonspecific binding. Test peptides (Peninsula Labs., Belmont, Calif.) included AM, PO72, calcitonin gene-related peptide (CGRP), gastrin releasing peptide (GRP), glucagon-like peptide 1 (GLP 1), vasoactive intestinal peptide (VIP), arginine vasopressin (AVP), growth hormone releasing factor (GRF), cholecystokinin (CCK), amylin, gastrin, oxytocin, calcitonin, α-melanocyte stimulating hormone (αMSH), pancreatic polypeptide, peptide tyrosine-tyrosine (PYY), Tabanus atratus hypotrehalosemic hormone, and BSA (Sigma Chemical Co., St. Louis, Mo.) as a negative control. These test peptides were chosen because they have a C-terminal tyrosine amide region or are structurally similar to AM. The antibody was tested at serial 2-fold dilutions ranging from 1:100 to 1:204,800.

c. mRNA Extraction, RT-PCR and Cloning: The oligonucleotide primers were synthesized using a MilliGen/Biosearch 8700 DNA synthesizer (Millipore, Marlborough, Mass.) Primer sets for AM detection were as follows: sense, $AM_{250-270}$, 5'-AAGAAGTGGAATAAGTGGGCT-3' (SEQ. ID. NO. 8); antisense, $AM_{640-660}$, 5'-TGGCTTAGAAGACACCAGAGT-3' (SEQ. ID. NO. 9); and nested probe antisense, $AM_{541-561}$, 5'-GACGTTGTCCTTGTCCTTATC-3' (SEQ. ID. NO. 10), with a predicted product of 410 bp. For AM-R amplification, the following primers were used: sense, $AM-R_{476-497}$, 5'-AGCGCCACCAGCACCGAATACG-3' (SEQ. ID. NO. 11); antisense, $AM-R_{923-946}$, 5'-AGAGGATGGGGTTGGCGACACAGT-3' (SEQ. ID. NO. 12); antisense probe, $AM-R_{788-811}$, 5'-GGTAGGGCAGCCAGCAGATGACAA-3' (SEQ. ID. NO. 13), yielding a 471 bp product. Procedures for RT-PCR, Southern and Western blotting have been described previously (Martínez, et al., *Endocrinology* 136, 4099 (1995)). In brief, reverse transcription was performed using the SuperScript Preamplification System (Life Technologies). A Perkin-Elmer 9600 Thermocycler was used to amplify the samples for 35 cycles with annealing temperatures of 55° C. and 61° C., respectively, for the ligand and its receptor. All buffers, enzymes and nucleotides used were obtained from Applied Biosystems (Perkin-Elmer Cetus, Norwalk, Conn.). PCR products were analyzed electrophoretically using 1% agarose gels, and the ethidium bromide staining was observed under UV light, followed by Southern analysis with $^{32}P$ end-labeled probes.

TABLE 3

| Tumor type | Expression of AM mRNA | Expression of AM-R mRNA |
|---|---|---|
| Small cell lung cancer | 14/15 | 10/13 |
| Non-small lung cancer | 12/14 | 12/16 |
| Breast cancer | 7/7 | 3/3 |
| Colon cancer | 2/2 | 0/1 |
| Nervous system tumors | 11/11 | nd |
| Ovarian cancer | 5/5 | 2/3 |
| Prostate cancer | 1/1 | nd |
| Adrenal cancer | 1/1 | nd |
| Chondrosarcoma | 1/1 | nd |
| Chronic monocytic leukemia | 1/1 | nd |
| Total for all cancers | 55/58 (95%) | 27/36 (75%) |

Table 3 sets forth a summary of tumor cell lines evaluated for AM and AM-R mRNA by RT-PCR analysis showing a widespread expression. The tumor cell lines evaluated come from diverse tissue types that express AM mRNA in 55/58 (95%) and AM-R mRNA in 27/36 (75%) as evaluated by RT-PCR, followed by southern blot analysis. nd=not done.

The fact that certain tissues do not express AM by Northern blot analysis does not preclude its presence (see Table 4). For example, a heterogenous tissue, such as whole brain, showed AM expression by RT-PCR, but not by Northern blot analysis. Table 4 sets forth a summary of normal tissue evaluated for AM mRNA by RT-PCR analysis. Many tissues express AM in addition to those reported previously by Northern blot analysis (Kitamura, K., et al., *Biochem. Biophys. Res. Commun.* 194, 720 (1993)). All normal human tissue polyA+ RNA was acquired through Clontech (California) and the primary epithelial cells were obtained from Clonetics (California).

Table 4 sets forth a summary of normal tissue evaluated for AM mRNA by RT-PCR analysis. A comparison of the results obtained by Kitamura, et al. using Northern blot analysis and this evaluation by RT-PCR. Some tissues, which were undetectable by Northern blot analysis were positive after amplification. nd=not done.

TABLE 4

| Tissue | | Northern | RT-PCR |
|---|---|---|---|
| Lung: | Adult | + | + |
| | Fetal | nd | + |
| Heart | | + | + |
| Liver: | Adult | − | + |
| | Fetal | nd | + |
| Skeletal muscle | | nd | + |
| Testis | | nd | + |
| Adrenal gland | | + | + |
| Kidney | | + | + |
| Uterus | | nd | + |
| Mammary gland | | nd | + |
| Prostate | | nd | + |
| Thyroid | | nd | − |
| Retina | | nd | + |
| Placenta | | nd | + |
| Thymus | | nd | − |
| Spleen | | − | − |
| Trachea | | nd | + |
| Primary bronchial epithelial cells | | nd | + |
| Brain: | Adult | − | + |
| | Fetal | nd | − | d. Southern Blot Analysis: Gels were denatured in 1.5 M NaCl/0.6M NaOH (30 min.×2), neutralized in 1.5 M NaCl/2 M Tris (30 min.×2) and blotted onto a 0.2 μm nitrocellulose filter in 20×SSC by capillary flow transfer overnight. The filter was crosslinked at 80° C. under vacuum, then incubated in prehybridization buffer. The antisense nested probe was $^{32}P$-end-labeled by standard procedures using T4 kinase. Hybridization with the labeled probe ($1\times10^6$ cpm/ml) wad one overnight at 42° C. Room temperature stringency washing was in 5×SSC/0.1% SDS (30 min.) and 1×SSC/0.1% SDS (30 min.). Filters were air dried and autoradiographed on Kodak XAR5 film.

e. Western Blotting: Whole cell lysates were generated following a modified protocol that was previously reported (Cuttitta, et al., *Nature* 316:823-826 (1995)). In summary, cells were harvested 48 hours after their last feeding, washed three times in cold PBS and pelleted by centrifugation (2,000 rpm for 10 minutes at 4° C.). The pellet ($\approx 5\times 10^7$ cells) was resuspended in 1 ml of PBS containing 1 μM final concentration of each of the following protease inhibitors: pefabloc (Centerchem Inc., Stamford, Conn.), bestatin and phosphoramidon (Sigma). The cell suspension was then homogenized, sonicated, clarified by ultracentrifugation, and the final protein concentration determined (BCA kit, BioRad Laboratories, Richmond, Calif.). Cell lysates were diluted in 2× Tricine sample buffer to an approximate protein concentration of 35 μg/50 μl, heated to 95° C. for 3 minutes, and loaded into the sample well.

Cell lysates were electrophoretically fractionated on 10-20% Tricine gels (NOVEX, San Diego, Calif.) at 100 volts for 2 hours under non-reducing conditions, 2 ng of peptide PO72 and AM were added to separate wells as positive control standards. Transfer blotting was accomplished in the same apparatus equipped with a titanium plate electrode and transferred to a polyvinyldifluoride membrane (Immobilon PVDF, Millipore) at 30 volts for 3 hours. The membrane was blocked overnight in 1% BSA-PBS, incubated for 1 hour in 1:1,000 dilution of rabbit anti-PO72 (bleed #2343), washed three times in PBS, exposed to $1\times10^6$ cpm $^{125}$I-Protein A for 30 minutes at 4° C., washed 6 times in PBS, dried and autoradiographed overnight at −80° C. on Kodak XAR5 film. Specificity control consisted of a duplicate membrane incubated in antigen-preadsorbed (10 mmols/ml PO72) antiserum.

f. HPLC Characterization: The lung carcinoid cell line, H720, was acclimated to grow in RPMI-1640 under a serum-free/hormone-free environment (RO) and the resulting conditioned medium (ROCM) was subjected to HPLC fractionation (Siegfried, J. M., et al. *J. Biol. Chem.* 269:8596-8603; and Reeves, J. R., *J. Biol. Chem.* 263:1928-1932 (1989)). Protease inhibitors were added, as described for whole cell lysates, to consecutive 1 liter harvests of ROCM and stored at 4° C. until further processed. Pooled ROCM (10 liters) was freeze-dried (Freezemobile 12EL, Virtis, Gardiner, N.Y.), reconstituted to 500 ml with distilled water, centrifuged and filter sterilized (0.45 um) to remove particulate matter. The resulting filtrate was loaded onto a semipreparative C18 column (DeltaPak, Millipore, 30×300 mm) using an auxillary rotary pump (Ranin, Wobern, Mass.) with a flow rate of 15 ml/min. Column reternate was selectively eluted over 150 min. using a 5 to 60% acetonitrile gradient containing 0.1% TFA and monitored at 210 and 280 nm (Beckman System Gold HPLC, San Ramon, Calif.). Twelve ml/min. fractions were collected, freeze-dried and stored at −80° C. until further analysis. Stored fractions were resuspended in 2× Tricine sample buffer and subject to Western blot analysis described above.

g. Immunohistochemistry: Cell pellets from tumor cell lines grown in RO were fixed in either 4% paraformaldehyde of Bouin's for 2 hours, embedded in 1k low melting point agarose, and further embedded in paraffin. Sections were stained using the avidin-biotin complex (ABC) method. Briefly, after an overnight incubation with rabbit anti-human PO72 antibody (1:1000), the cells were incubated with biotinylated goat anti-rabbit immunoglobin (1:200, Vectastain, Burlingame, Calif.) and then with avidin-biotin peroxidase complex (1:100, Vectastain). Pre-incubation of the antiserum with 10 nmols/ml of human PO72 was used as the absorption control. The bound antibodies were visualized using diaminobenzidine (Sigma) and $H_2O_2$. Sections were lightly counterstained with hematoxylin.

h. In situ RT-PCR: Analysis was performed on cell lines and tissues using a direct method as previously described (Martinez, A., et al., *J. Histochem. Cytochem.* 43:739-747 (1995). In brief, sections were mounted on silanated slides, dewaxed, permeabilized with proteinase K (10 μg/ml, 15 min. at 37° C.) and reverse transcription performed (Superscript II, Life Technologies). PCR was completed after 20 cycles in an Omnislide thermocycler (Hybaid, Holbrook, N.Y.). Composition of the PCR mixture was similar to the solution used for standard PCR with the addition of digoxigenin-11-dUTP to label the products. Digoxigenin tagged amplicons were visualized with a digoxigenin detection kit (Boehringer Mannheim, Indianapolis, Ind.). Omission of the RT step or of the specific primers in the PCR mix were used as negative controls.

i. Growth Assays: MTT techniques were performed as previously described (Nakanishi, Y. F., et al., *Exper. Cell Biol.* 56:74-85 (1988)). In brief, a single cell suspension of $2\times10^5$ cells/ml (50 μl/well) is seeded into 96-well PVC plates and an appropriate concentration of MoAb-G6 and AM was added in a volume of 50 μl. The assay is performed in TIS medium (RMPI 1640 plus 10 μg/ml transferrin, 10 μg/ml insulin and $3\times10^8$M sodium selenite). After 5 days growth at 37° C., 5% $CO_2$, in a humid incubator, the dye and solubilization solutions were added from the Promega Proliferation Assay (Madison, Wis.), which is a variation of the MTT assay (Carmichael, Y. F., et al., *Cancer Res.* 47:943-946 (1987)). The Biorad Microplate Manager plate reader and software was used to determine the change in number of viable cells from dye reduction measured by absorbance at 570 nm.

TABLE 5

| Cell Line | Tumor Type | % Growth ± s.d. | |
|---|---|---|---|
| | | MoAb-G6 (100 μg/ml) | MoAb-G6 + AM (10 μM) |
| H157 | adenosquamous | 68.6% ± 7.4 | 91.8% ± 8.4 |
| H720 | lung carcinoid | 64.3% ± 18.3 | 100.0% ± 14.0 |
| MCF-7 | breast adenoCA | 44.7% ± 4.3 | 89.7% ± 5.8 |
| OVCAR-3 | ovarian adenoCA | 64.3% ± 9.9 | 98.0% ± 13.5 |
| SNUC-1 | colon adenoCA | 96.8% ± 4.5 | 100.0% ± 10.2 |

Table 5 sets forth a summary of the inhibitory effects caused by MoAb-G6 and recovery with the addition of AM. Growth inhibition ranges between 25-60% in the tested cell lines as compared to control, that is, without the addition of MoAb-G6. Furthermore, specificity is demonstrated by reversing the effects of MoAb-G6 with the addition of synthetic AM. Colon cancer cell line, SNUC-1 did not respond to MoAb-G6. Values are the mean of 24 wells in three different experiments and their standard deviations (s.d.). CA=carcinoma.

j. Receptor Binding: Receptor binding analysis were performed as previously described (Moody, T. W., et al., *Proc. Natl. Acad. Sci.* U.S.A. 90:4345-4349 (1993)). Briefly, cells ($5\times10^4$) were placed in 24-well plates coated with fibronectin (20 μg). When a monolayer is formed, the cells were washed 4 times in TIS buffer followed by incubation with receptor binding medium (TIS plus 1% BSA and 1 mg/ml bacitracin). The cells were incubated with $^{125}$I-AM (Phoenix Pharmaceuticals) for 30 mins at 37° C. After washing the cells 4 times in receptor binding buffer at 4° C., they were dissolved in 0.2 N NaOH and counted on a gamma counter.

k. cAMP Assays: Cyclic AMP was assayed by RIA using a kit obtained from New England Nuclear (Boston, Mass.). Cells in 24-well plates were resuspended in TIS medium containing 1% BSA, 1 mg/ml bacitracin and 100 μM isobutyl-methyl-xanthine. AM was added ranging from 0.1 pM-10 μM, and after 5 minutes, the reaction was terminated by adding an equal volume of ethanol. The supernatants were tested for cAMP using the RIA kit following the manufacturer's instructions.

Example 13

Demonstration of Secretion of AM by Human Tumor Cell Lines

Figure 14C:
Figure 14D:

Select cancer cell lines were adapted to grow in serum-free, hormone-free medium (RO), and the resulting whole cell lysates from such tumor cell lines and normal tissue extracts were then examined by Western blot analysis using a previously characterized rabbit antiserum to AM (Martínez, et al., *Endocrinology* 136, 4099 (1995)). FIG. 14C illustrates the electrophoretic profile of the AM-like immunoreactive peptides identified. Molecular weight species of 18, 14, and 6 kDa were identified and represent AM precursor, processed intermediates, and the authentic peptide, respectively. Not all of the tumor cell lines demonstrated the presence of the 6 kDa entity, which represents the authentic peptide. The specificity of the immune-detection assay was confirmed by an antibody absorption control, which eliminated specific autoradiographic band formation (see FIG. 14D).

To further corroborate the expression of authentic AM by tumor cells, HPLC fractionation of R0-conditioned medium was analyzed from the lung carcinoid cell line NCIH720. Briefly, H720 cells were mass cultured in approximately 5 L of hormone-free medium and freeze dried at 10× concentration. The H720 conditioned medium (CM) was then filter sterilized using a 0.45 µm filter. In preparation for HPLC chromatography, the following protease inhibitors were added to the CM: pefabloc 1 µM, bestatin 1 µM, and phosphoramidon 1 µM. The CM was loaded onto a semipreparative C18 column (30×120 mm) attached to a Beclunan System Gold HPLC using an acetonitrile gradient from 5 to 60% (with 0.1% trifluouroacetic acid) over a time course of 150 min; 12 fractions were collected, freeze-dried and resuspended in the appropriate volume of buffer. FIG. 15A illustrates the fractionation of 5 L of H720 CM concentrated to 500 mL before injection, compared with the elution time of synthetic AM at 89.4 min (arrow). FIGS. 15B and 15C show that AM immunoreactivity occurs at approximately 88.8 min. in the H720 CM by either solid phase (see FIG. 15B) or Western blot analysis (FIG. 15C). The Western analysis demonstrates that the fractions at 88 to 92 min contain the 6 kDa entity, and those at 124 to 129 min contain the 14 and 18 kDa entities.

The cell line NCIH720 contained AM-like immunoreactivity with a column elution time consistent with synthetic peptide ($\approx$89 min) (FIGS. 15A and 15B). In addition, immunoblot analysis of consecutive HPLC fractions within the 88 to 92 min region revealed a major 6 kDa immunoreactive band, while the 122 to 129 min fractions expressed both the 18 and 14 kDa entity (see FIG. 15C). Thus, R0 adapted human tumor cell lines were shown to express authentic AM by two separate biochemical techniques.

Example 14

The Regulation of Human Tumor Cell Proliferation by AM

Consistent results were observed by immunohistochemical and in situ RT-PCR (Martínez, et al., *J. Histochem. Cytochem.* 43, 739 (1995)) examination of paraffin-embedded R0-adapted cell lines. Heterogeneous expression of AM was observed with the highest intensity of staining confined to the outer cell layers (proliferative zones) of individual colonies, a finding that implicates AM in growth regulation. To further evaluate this hypothesis, MTT assay techniques were used (D. N. Carney, et al., *Proc. Natl. Acad Sci.* U.S.A. 79, 3185 (1981)) to examine the effects of AM on the growth of several diverse tumor cell lines, specifically, lung, colon, breast, brain, and ovarian cell lines. Exogenous addition of AM (0.1 nM to 100 nM) to R0-grown cell cultures was ineffective in stimulating growth, although there was some nonspecific toxicity at the higher range. Since the test cell lines were known to produce authentic AM peptide, it was assumed that this inability to stimulate growth with extrinsic ligand meant that it had already achieved maximal proliferative effects using its own AM-producing mechanism.

In a parallel setting, MoAb-G6 was used to block endogenous AM biological activity. This monoclonal antibody was generated against a synthetic homolog of AM (PO72) and structurally represents two-thirds of the intact peptide (TVQKLAHQIYQFTDKDKDNVAPRSKISPQGY-NH$_2$ (SEQ. ID. NO. 14)). Immunization, fusion, and hybridoma screening strategies were completed as previously described (Cuttitta, et al., Nature 316, 823 (1985)). MoAb-G6, an IgA subtype, did not cross-react with other known tyrosine amide peptides or with the structurally related CGRP and amylin (see FIG. 13). Before its use in vitro, the MoAb-G6 was affinity-purified from ascites fluid using a solid-phase antigen column and eluted at 60 mm with 0.1M citric acid (pH 3.0). The addition of synthetic AM alone induced a slight suppression ($\approx$10%) at higher ranges (10 µM) (FIG. 12B). The MTT assay was used to evaluate MoAb-G6 for its effect on the growth of several human tumor cell lines (NCI-H157, NCI-H720, MCF-7, SNUC1 and NIH:OVCAR-3), and in every case (5 out of 5) a dose-dependent suppression was observed. Maximal growth inhibition ranged from 20 to 55% for the cell lines tested. Representative data for MCF-7 are depicted in FIG. 12A, which shows that an isotypic control mouse myeloma protein (TEPC 15, IgA$_K$, Sigma) was ineffective in blocking growth over the same dose range. MoAb-G6 induced inhibition of tumor cell growth was abolished by exogenous addition of AM, with maximal recovery at 10 µM, thus verifying the specificity of the immune suppressive growth (FIG. 12B).

Example 15

Determination of the Distribution of AM in the Pancreas by Immunocytochemistry

Pancreata from rats, hamsters, guinea pigs, cats, and dogs were fixed in Bouin's fluid (Sigma, St. Louis, Mo.) and embedded in paraffin. The avidin-biotin-peroxidase complex method (Hsu, et al., *J Histochem Cytochem* 29:577-580 (1981)) was performed using a polyclonal antibody to AM previously characterized (Martínez, et al., *Endocrinology* 136, 4099 (1995)) and commercially available antibodies against insulin, glucagon, somatostatin, and pancreatic polypeptide (Accurate Chemical & Scientific Corp., Westbury, N.Y.). Negative controls included substitution of the primary antibody by preimmune serum from the same rabbit and preabsorption of the antibody with 10 nmols/mL of the synthetic peptide (AM or CGRP). For immunoelectron microscopy three rats were perfused with a mixture of 2.5% paraformaldehyde +2.0% glutaraldehyde in cacodylate buffer. Small pieces of pancreas were dehydrated and embedded in resin. Ultrathin sections were mounted in nickel grids and the double immunogold method was performed as previously described (Martínez, et al., *J. Histochem. Cytochem.* 43, 739 (1995)).

FIG. 17A shows a rat pancreas with mild immunoreactivity throughout the entire islet of Langerhans and strongly stained cells in the periphery. No counterstaining was applied to this section. FIG. 17B sets forth Hamster pancreas which displays a similar pattern. FIG. 17C set forth dog pancreas containing numerous immunoreactive cells scattered throughout the parenchyma. FIG. 17D depicts the immunoreactivity in ductal systems of guinea pig pancreas. Note that endocrine cells are more intensely stained than duct cells. FIG. 17E shows serial sections of hamster pancreas immunostained for AM and FIG. 17F shows pancreatic polypeptide show colocalization of both immunoreactivities (arrows). FIG. 17G sets forth double immunogold staining by electron microscopy showing colocalization of AM (small gold particles, 10 nm) and pancreatic polypeptide (large gold particles, 20 nm) in the cell situated to the left. A small fragment of a negative α-cell can be observed to the right. Inset shows two secretory granules containing both immunoreactivities at higher magnification. FIG. 17H shows detail of a D-cell showing some immunoreactivity for AM (large particles) in the somatostatin-containing (small particles) secretory granules.

Example 16

AM Increases cAMP and AM Receptors are Present in Human Tumor Cell Lines

Figure 19A:
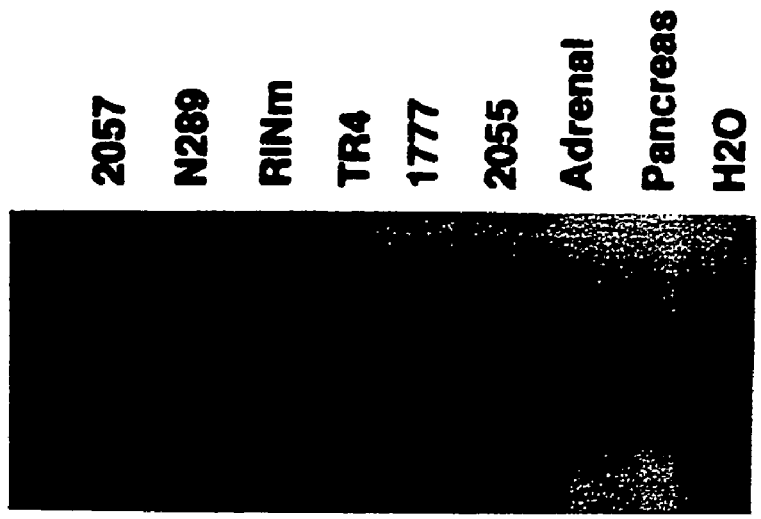
FIGS. 19A and 19B.
Figure 19B:

Following previously established protocols (T. W. Moody, et al., *Proc. Natl. Acad. Sci* U.S.A. 90, 4345 (1993)) iodinated ligand (Phoenix Pharmaceuticals) and cAMP response to synthetic AM was used to analyze the presence of AM receptor in responding tumor cell lines. Several cancer lines demonstrated selective binding of $^{125}$I-AM, which was not competitively blocked by the synthetic homolog PO72 or the gene-related peptide PAMP (FIG. 19A-*check*). The data show that specific binding is inhibited by AM in a dose-dependent manner with an $IC_{50}$ of 10 nM. In addition, AM binding to this receptor system induced a rapid linear increase in cellular cAMP over a dose range of 10 pM to 1 μM ($ED_{50}$ 5 nM), thereby resulting in a maximum elevation three times that of the normal control (FIG. 19B). In contrast, PO72 and PAMP had no effect on cAMP.

Example 17

Determination of the Effects AM and MoAb-G6 on the Release of Insulin From Rat Isolated Islets Dose-dependent increase of intracellular cAMP in the islets following addition of AM. Islets from six rats were isolated following well-established protocols (Gray, et al., *Diabetes* 33, 1055 (1984)). Assays were performed in 24-well plates (90 islets per well). After a 45 min incubation in RPMI-1690 medium containing 5.6 mM glucose, a second incubation in RPMI containing 20.6 mM glucose and the proper concentration of AM and/or the antibody was performed. Supernatants from both incubations were tested by radioimmunoassay (RIA) for insulin (Amersham, Arlington Heights, Ill.). The ratio between the insulin concentration found in the high glucose supernatant and the insulin measured in the low glucose solution is represented in ordinates. After collecting the medium, the islets from the same experiments were saved for analysis of cAMP contents (Korman, et al., *Cancer Res.* 46, 1214 (1986)). Islets were extracted in 50% ethanol and centrifuged, and the supernatants were tested for cAMP using a RIA kit (New England Nuclear, Boston, Mass.) following manufacturer's instructions. The experiments were repeated three times and a representative example shown. Data are means±standard deviations of two wells.

Example 18

Southern Blot

The mRNA used for Southern blotting was either purchased (Clontech, Palo Alto, Calif.) in the case of the normal tissues, or extracted from the cell lines using the MicroFast Track kit (Invitrogen, San Diego, Calif.). Reverse transcription (RT), polymerase chain reaction (PCR), and Southern blot were carried out as previously described (Martínez, et al., *Endocrinology* 136, 4099 (1995)). A set of primers that recognizes the most conserved regions of the AM gene were designed and used. The primer sequences are Sense (AM 250-270) 5'-AAG-AAG-TGG-AAT-AAG-TGG-GCT-3' (SEQ. ID. NO. 15); Antisense (AM 523-542) 5'-TGT-GAA-CTG-GTA-GAT-CTG-GT-3' (SEQ. ID. NO. 16). The probe used for Southern was AM (430-450) 5'-TCT-GGC-GGT-AGC-GCT-TGA-CTC-3' (SEQ. ID. NO. 17). These primers produce 292 bp products. Base sequence analysis of isolated bands confirmed identity of the RT-PCR product.

Example 19

Glucose Tolerance Tests

Glucose tolerance tests were performed on Sprague-Dawley rats (250 to 300 g) in the presence (○) or absence (●) of AM. (FIG. 20A) Significant differences (p<0.01) in insulin levels can be observed 20 mm after intravenous injection of AM. (FIG. 20B) Difference in levels of circulating glucose was also highly significant (p<0.01) 1 h after injection. Glucose tolerance methods have been published previously (Brown, et al., Proc. Soc. Exp. Biol. Med. 150, 557 (1975)). Six rats were administered a glucose solution (400 mg/100 g body weight) via gastric intubation. Ocular blood samples were collected at intervals following glucose loading, and glucose concentration was determined by a calorimetric assay (Sigma). Blood insulin levels were determined on the same samples by radioimmunoas say (Amersham). Three days later, the same rats received 1 μL of AM (60 μM) per g body weight through intravenous injection and tolerance tests were repeated. Data are means±standard deviations for the six animals. Two-tailed Student's test was performed to determine statistical significance. (*) indicates statistical significance (p<0.01).

Example 20

The Localization of AM mRNA and Immunoreactivity in Various Organs of Different Species In situ RT-PCR and immunohistochemistry were performed as described in Martinez, et al., *Endocrinology* 136: 4099 (1995). Briefly, the tissues used for in situ RT-PCR were fixed in 4% paraformaldehyde, whereas the tissues for immunohistochemistry were fixed in Bouin's fluid (Sigma Chemical Co.). Controls for in situ RT-PCR included omission of the reverse transcriptase step of substitution of the specific primers by water. Negative controls for immunohistochemistry consisted in preabsorption of the antibody with 10 nmols/ml of synthetic AM or substitution of the primary antibody by preimmune serum.

Example 21

Effect of AMP and PAMP on the Inhibition of Growth of *E. coli*

Figure 22:
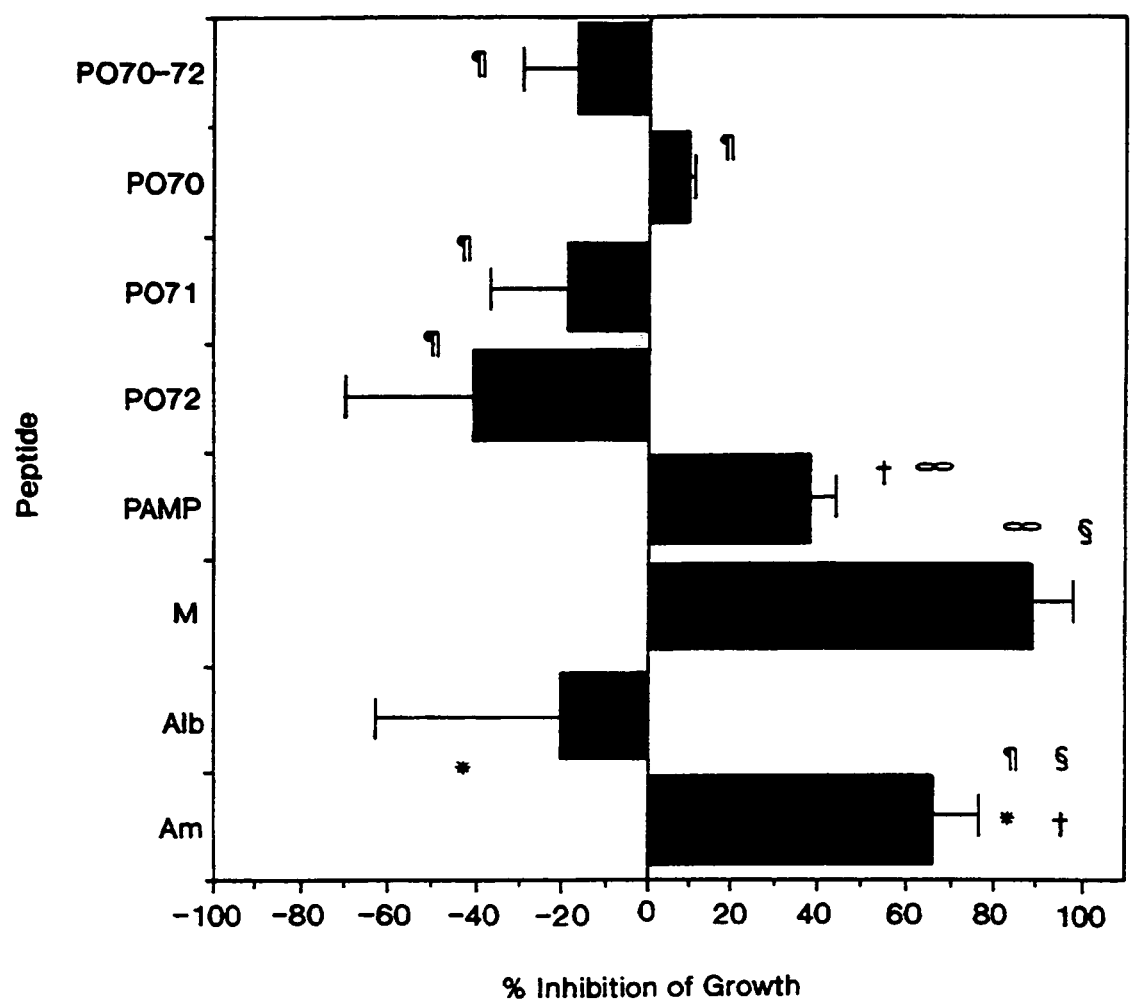
FIG. 22.

Inhibition of growth of *E. coli* was assessed in a microdilutional timed kill assay. (See FIG. 22) Bacteria and *Candida albicans* were grown overnight on trypticase soy agar (TSA) and Sobouraud dextrose agar (SDA) plates, respectively, were suspended into RPMI-1640 medium (Bio-Whittaker) and adjusted to a final concentration of $8 \times 10^3$ cfu/ml in 200 μM in plastic microdilution trays. AM-related peptides, magainins, and albumin were added in equimolar concentrations ranging from 8 µM to 300 µM. Plates were incubated at 37° C. with gentle agitation over 24 hours. At 6 hr and 24 hr time points, 10 to 50 µM aliquots from each well were quantitatively cultured by serial 100-fold dilutions onto TSA and SDA plates.

Example 22

Antimicrobial Activity of AM and PAMP

The antimicrobial activity of AM and PAMP was determined in a macrodilution assay after 6 hours of incubation of *E. coli.* (See FIG. 23A) There was initially no activity observed for AM at 6 hours, moderate activity for magainin, and greater activity generated by PAMP. As of the 24 hour incubation (see FIG. 23B) AM was slightly more active than PAMP in growth inhibition, while magainin (M) was more potent than either AM (p=0.006) or PAMP (p=0.004). Data were compiled from six experiments. Macrodilution assays were performed in 12×75 mm borosilicate glass tubes. Organisms were grown and harvested, as described in Roilides, E., et al., J Infect Dis. 163:579 (1991), and adjusted to a final inoculum concentration of $8 \times 10^3$ cfu/ml in 400 µl. AM-related peptides, magainins, and albumin were added in equimolar concentrations ranging from 8 µM to 300 µM. Tubes were incubated at 37° C. with gentle agitation over 24 hours. At 6 and 24 hour time points, 100 µl aliquots from each tube were quantitatively cultured by serial 100-fold dilutions onto TSA and SDA plates.

Example 23

The Effect of AM on the Termination of *C. albicans*

Figure 24:
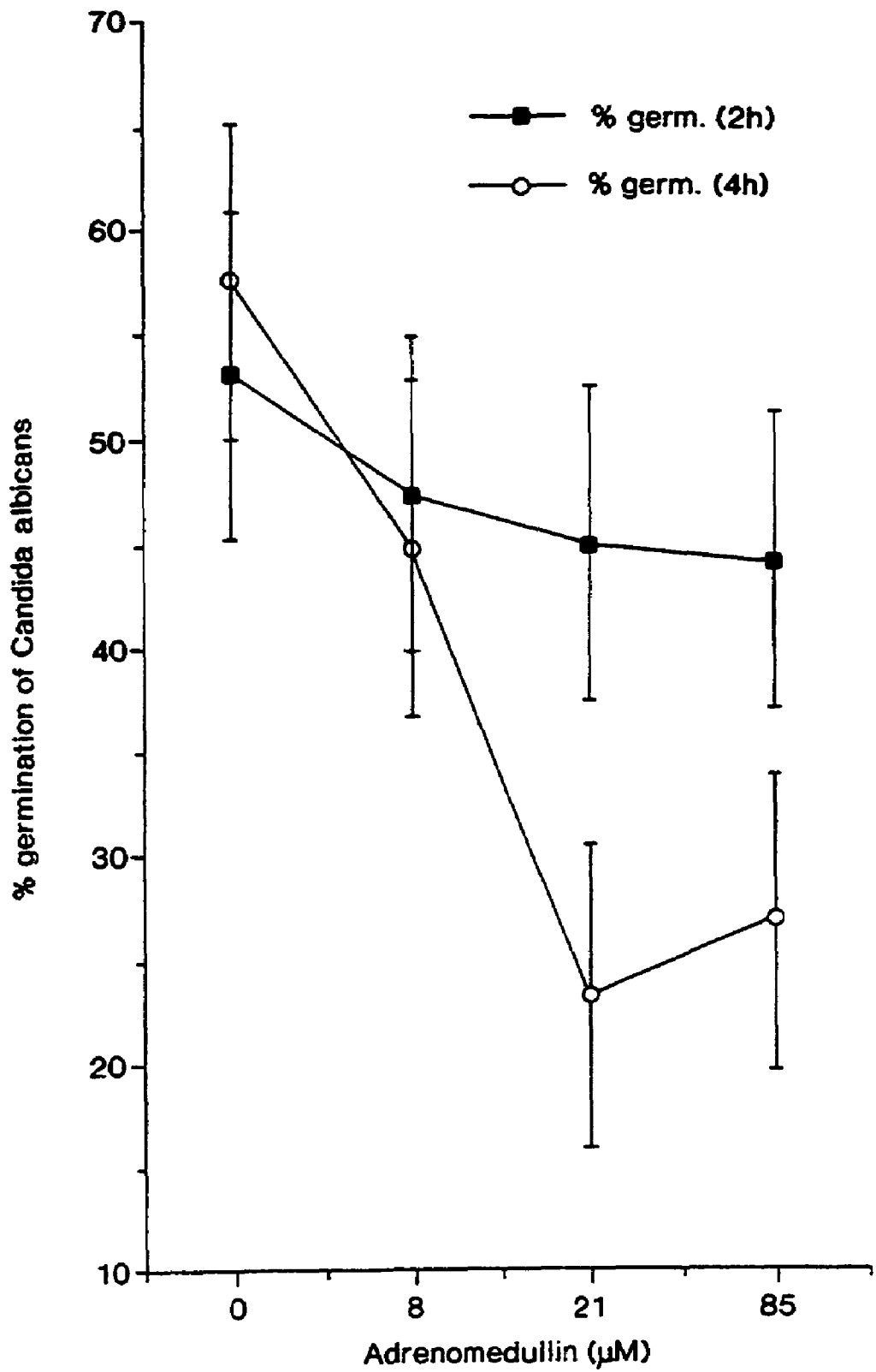
FIG. 24.

There was a significant inhibition of germination of *C. albicans* by increasing concentrations of AM at 4 hours incubation (p=0.048, ANOVA) (see FIG. 24). The trend in suppression of germination after 2 hours incubation was not significant. Data were compiled from 11 experiments. Germination was determined by incubating colonies of *C. albicans* that were harvested from an overnight growth on SDA and suspended on RPMI-1640 containing concentrations of AM from 8 to 85 µM. Organisms were incubated at 37° C. and germination was measured at 2 h and 4 h by reading 100 to 200 organisms per concentration per time point in each experiment. Percent germination was assessed as the proportion of blastoconidia of *C. albicans* bearing the characteristic parallel-walled tubular element to the total number of blastoconidia.

REFERENCES

1. Kitamura K., et al., *Biochem Biophys Res Commun* 192: 553-560 (1993).
2. Eguchi S., et al., *Endocrinology* 135:2454-2458 (1994).
3. Kitamura K., et al., *Biochem Biophys Res Commun* 194: 720-725 (1993).
4. Ishimitsu T., et al., *Biochem Biophys Res Commun* 203: 631-639 (1994).
5. Kitamura K., et al., *FEBS Lett* 338:306-310 (1994).
6. Sakata J., et al., *Biochem Biophys Res Commun* 195:921-927 (1993).
7. Nuki C., et al., *Biochem Biophys Res Commun* 196:245-251 (1993).
8. Ishiyama Y., et al., *Eur J Pharmacol* 241:271-273 (1993).
9. Perret M., et al., *Life Sci* 53:PL377-PL379 (1993).
10. Lippton H., et al., *Life Sci* 54:PL409-PL412 (1994).
11. Santiago J. A., et al., *Eur. J. Pharmacol* 272:115-118 (1995).
12. Lippton H., et al., *J Appl Physiol* 76:2154-2156 (1994).
13. Sugo S., et al., *Biochem Biophys Res Commun* 201:1160-1166 (1994).
14. Eguchi S., et al., *FEBS Lett* 340:226-230 (1994).
15. Ishizaka Y., et al., *Biochem Biophys Res Commun* 200: 642-646 (1994).
16. Kawada N., et al., *FEBS Lett* 356:109-113 (1994).
17. Ebara T., et al., *Eur J. Pharmacol* 263:69-73 (1994).
18. Nossaman B. D., et al., *Life Sci* 56:PL63-PL66 (1995).
19. Kanazawa H., et al., *Biochem Biophys Res Commun* 205: 251-254 (1994).
20. Kitamura K., et al., *FEBS Lett* 341:288-290 (1994).
21. Siegfried J. M., et al., *J Biol Chem* 269:8596-8603 (1994).
22. Glisin V., et al., *Biochemistry* 13:2633-2637 (1974).
23. Cuttitta F., et al., *J Clin Endocrinol Metab* 67:576-583 (1988).
24. Hsu S. M., et al., *J Histochem Cytochem* 29:577-580 (1981).
25. Martínez A., et al., *J Histochem Cytochem,* 43, 739 (1995).
26. Sugo S., et al., *Biochem Biophys Res Commun* 203:719-726 (1994).
27. Springall D. R., et al., *J Auton Nerv Syst* 20:155-166 (1987).
28. Takahashi H., et al., *Am J Hypertens* 7:478-482 (1994).
29. Giaid A., et al., *Am J Respir Cell Mol Biol* 4:50-56 (1990).
30. Diamond G., et al., *Proc Natl Acad Sci* USA 90:4596-4600 (19-93).
31. Diamond G., et al., *Proc Natl Acad Sci* USA 88:3952-3956 (1991).
32. Saldise L., et al., 8th National Congress of Histology, Jaen, Spain, 1993, pp 195-196 (Abstract).
33. Ishizuka J., et al., *Cancer Res* 54:2129-2135 (1994).
34. Moody T. W., et al., *Proc Natl Acad Sci* USA 90:4345-4349 (1993).
35. Weinstat-Saslow D., Steeg P. S., *FASEB* 8:401-407 (1994).
36. Bloom S. R., Polak J. M., *Adv Clin Chem* 21:177-244 (1980).
37. Vane J. R., Botting R. M., *J Physiol Pharmacol* 43:195-207 (1992).
38. Kitamura, K., et al., *Biochem. Biophys. Res. Commun.* 194, 720 (1993).
40. Shimosawa, T., et al., *J. Clin. Invest.* 96, 1672 (1995).
41. Ishizaka, Y., et al., *Biochem. Biophys. Res. Commun.* 200, 642 (1994).
42. Santago, J. A., et al., *Life Sci.* 55, 85 (1994).
43. cheng, D. Y., et al., *Life Sci.* 55, 251 (1994).
44. Shimekake, Y., et al., *J. Biol. Chem.* 270,4412 (1995).
45. Ebara, T., et al., *Eur. J. Pharmacol.* 263, 69 (1994).
46. Jougasaki, M., et al., *Amer. J. Physiol.* 37, F657 (1995).
47. Murphy, T. A. and W. K. Samson, *Endocrinology* 136, 2459 (1995).
48. Yamaguchi, T., et al., *Life Sci.* 56, 379 (1995).
49. Samson, W. K., et al., *Endocrinology* 136, 2349 (1995).
50. Satoh, F., et al., *J. Clin. Endocrinol. Metabol.* 80, 1750 (1995).
51. Martínez, A., et al., *Endocrinology* 136, 4099 (1995).
52. Carney, D. N., et al., *Proc. Natl. Acad Sci.* U.S.A. 79, 3185 (1981).
53. Cuttitta, F., et al., *Nature* 316, 823 (1985).
54. Cho-Chung, Y. S., et al., *Life Sci.* 48, 1123 (1991).
55. Hoosein, N. M., *Regul. Pent.* 24, 15 (1989).
56. Yu, D., et al., *Endocrinology* 131, 1188 (1992).

57. Lohmann, S. M. and U. Walter, in *Advances in Cyclin Nucleotide and Protein Phosphorylation Research*, P. Greengard, et al., Eds. (Raven Press, New York, 1984), vol. 18, pp. 63-117.
58. Ally, S., et al., *Proc. Natl. Acad. Sci. U.S.A.* 85, 6322 (1988).
59. Sugo, S., et al., *Biochem. Biophys. Res. Commun.* 207, 25 (1995).
60. Minamino, N., et al., *Biochem. Biophys. Res. Commun.* 211, 686 (1995).
61. Sugo, S., et al., *FEBS Lett.* 369, 311 (1995).
62. Ames, B. N., et al., *Proc. Natl. Acad. Sci. U.S.A.* 92, 5258 (1995).
63. Hao, Q., et al., *Life Sci.* 54, 265 (1994).
64. Feng, C. J., et al., *Life Sci.,* 55,433 (1994).
65. Korman, Y., et al., *Diabetes* 34, 717 (1985).
66. Wollheim, C. B., et al., *Diabetes* 29, 74 (1980).
67. Kato, F., et al., *J. Neurochem.* 64, 459 (1995).
68. Martínez, A., et al., *Endocrinology* 136, 4099 (1995).
69. Walsh, T., et al., *Science* (under editorial consideration).
70. Washimine, H., et al., *Histochemistry* 103, 251 (1995).
71. Kitamura, K., et al., *Drugs* 49, 485 (1995).
72. Mulder, H., et al., *Cell Tissue Res.* 274, 467 (1993).
73. Ahren, B. and F. Sundler, *Cell Tissue Res.* 269, 315 (1992).
74. Miller, M. J., et al., *Science* (under editorial consideration).
75. Pittner, R. A., et al., *J. Cell. Biochem.* 55S, 19 (1994).
76. Holz, G. G., et al., *J. Biol. Chem.* 270, 17749 (1995).
77. Hall, J. M., et al., *Brit. J. Pharmacol.* 114, 592 (1995).
78. Zimmermann, U., et al., *Peptides* 16, 421 (1995).
79. Hotamisligil, G. S. and B. M. Spiegelman, *Diabetes* 43, 1271 (1994).
80. Jones, T. H., Clin. *Endocrinol.* 40, 703 (1994).
81. Feng, C. J., et al., *Life Sci.* 55, 433 (1994).
82. Fiscus, R. R., et al., *Neuropeptides* 26, 133 (1994).
83. Schmidt, H. H. H. W., et al., *Science* 255, 721 (1992).
84. Worl, J., et al., *Histochemistry* 102, 353 (1994).
85. Hsu, S. M., *J. Histochem. Cytochem.* 29, 577 (1981).
86. Martínez, M., et al., *J. Histochem. Cytochem.* 41, 375 (1993).
87. Gray, D. W. R., *Diabetes* 33, 1055 (1984).
88. Korman, L. Y., *Cancer Res.* 46, 1214 (1986).
89. Brown, E. D., *Proc. Soc. Exp. Biol. Med.* 150, 557 (1975).
90. Ishiyama, et al. *Clin. Exper. Pharmacol. Physiol.* 22:614 (1995).
91. Allen, M. A., et al., *Proc. Soc. Neurosci.* (Abstract) 21:889 (1995)
92. Schonwetter, B. S., et al., *Science* 267:1645 (1995).
93. Zasloff, M., *Proc. Natl. Acad. Sci.* USA 84:5449 (1987).
94. Ghannoum, M. A., et al., *Candida Adherence to Epithelial Cells.* CRC Press; Boca Raton, Fla. 1990; pp.72-104.
95. Walsh, T. J., et al., *Antimicrob Chemother.* 17:75 (1986).
96. Roilides, E., et al., *J Infect Dis.* 163:579 (1991)
97. Roilides, E., et al., *J Leukocyte Biol.* 57:651 (1995).
98. Maloy, W. L. and Kari, U. P., *Biopolymers* (Peptide Science) 37:105 (1995).
99. Lehrer, R. I., et al., *Cell* 64:229 (1991).
100. Tytler, E. M., et al., *Biochemistry* 34:4394 (1995).
101. Oppenheim, F. G., et al., *J Biol Chem* 263:7472 (1988).
102. Shoji, H., et al., *Biochemical and Biophysical Research*, 215:531 (1995).

What is claimed is:

1. A method of treating a cell proliferation disease or condition in a subject, the method comprising administering to the subject an effective amount of PO72 (SEQ ID NO: 3), thereby treating the cell proliferation disease or condition in the subject.

2. The method of claim 1, wherein the condition is related to aberrant fetoplacental growth.

3. A method of regulating neuronal activity in a subject, the method comprising administering to the subject an effective amount of PO72 (SEQ ID NO: 3), thereby regulating the neuronal activity in the subject.

4. The method of claim 1, wherein the disease is a tumor or cancer.

5. The method of claim 4, wherein the tumor or cancer cell is selected from the group consisting of adrenal, nervous system, lung, colon, ovarian, prostate, bone, pancreas, and breast.

* * * * *

UNITED STATES PATENT AND TRADEMARK OFFICE
CERTIFICATE OF CORRECTION

PATENT NO. : 7,622,272 B2  Page 1 of 1
APPLICATION NO. : 11/517599
DATED : November 24, 2009
INVENTOR(S) : Cuttitta et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 155 days.

Signed and Sealed this

Twenty-sixth Day of October, 2010

David J. Kappos
*Director of the United States Patent and Trademark Office*

UNITED STATES PATENT AND TRADEMARK OFFICE
CERTIFICATE OF CORRECTION

PATENT NO. : 7,622,272 B2  
APPLICATION NO. : 11/517599  
DATED : November 24, 2009  
INVENTOR(S) : Cuttitta et al.

Page 1 of 1

It is certified that error appears in the above-identified patent and that said Letters Patent is hereby corrected as shown below:

On the Title Page, Section (56) FOREIGN PATENT DOCUMENTS:

Page 1, left column, "07-196693" should read --H7-196693--.

In the Specification:

Column 2, line 9, "CGRP8-37" should read --$CGRP_{8-37}$--.

Column 2, lines 32-33, "in vitro" should read --*in vitro*--.

Column 4, line 56, "in situ" should read --*in situ*--.

Column 5, line 3, "in situ" should read --*in situ*--.

Column 5, line 9, "in situ" should read --*in situ*--.

Column 6, line 28, "in situ" should read --*in situ*--.

Column 12, line 9, "Stinulation" should read --Stimulation--.

Column 14, line 7, "(1987)." should read --(1987)).--.

Column 15, line 22, "(1995)" should read --(1995))--.

Column 15, line 32, "Am" should read --AM--.

Column 28, lines 40-41, "wad one" should read --was done--.

Column 33, line 33, "Effects AM" should read --Effects of AM--.

Column 33, line 37, "following" should read --followed--.

Column 34, line 29, "radioimmunoas say" should read --radioimmunoassay--.

Signed and Sealed this  
Seventh Day of February, 2012

David J. Kappos  
*Director of the United States Patent and Trademark Office*